United States Patent
Ries et al.

(10) Patent No.: US 6,248,770 B1
(45) Date of Patent: *Jun. 19, 2001

(54) BENZIMIDAZOLES HAVING ANTITHROMBOTIC ACTIVITY

(75) Inventors: Uwe Ries; Iris Kauffmann, both of Biberach; Norbert Hauel, Schemmerhofen; Henning Priepke, Warthausen; Herbert Nar, Mittelbiberach; Jean Marie Stassen, Warthausen; Wolfgang Wienen, Biberach, all of (DE)

(73) Assignee: Boehringer Ingelheim Pharma KG, Ingelheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 28 days.

(21) Appl. No.: 09/338,970

(22) Filed: Jun. 24, 1999

Related U.S. Application Data

(60) Provisional application No. 60/092,215, filed on Jul. 9, 1998.

(51) Int. Cl.[7] .................. A61K 31/415; A61K 31/395; C07D 235/04; C07D 461/06; C07D 239/02
(52) U.S. Cl. .............. 514/394; 514/210.21; 514/234.5; 514/252.06; 514/269; 514/274; 514/332; 514/338; 514/369; 514/370; 514/394; 544/116; 544/238; 544/298; 544/315; 544/316; 544/317; 544/318; 544/319; 544/320; 544/370; 546/199; 546/256; 546/273.4; 548/143; 548/245; 548/253; 548/304.4; 548/304.7; 548/309.7; 548/310.1
(58) Field of Search ................ 514/310, 234.5, 514/252, 269, 274, 322, 338, 369, 370, 394, 210.21, 252.06; 544/116, 238, 298, 315, 316, 317, 318, 319, 320, 370; 546/199, 256, 273.4; 548/143, 305.7, 304.7, 304.4, 309.7, 245, 253, 310.1

(56) References Cited

U.S. PATENT DOCUMENTS

| | | |
|---|---|---|
| 4,634,783 | 1/1987 | Fujii et al. .................. 549/475 |
| 5,972,968 * | 10/1999 | De Nanteuil et al. ........... 514/338 |

FOREIGN PATENT DOCUMENTS

| | | |
|---|---|---|
| 198 29 964 * | 3/1999 | (DE) . |
| 198 57 202 * | 3/1999 | (DE) . |
| 11-100368 * | 4/1999 | (JP) . |
| 199 12 690 * | 4/1999 | (DE) . |
| WO9408962 | 4/1994 | (WO) . |
| WO9721437 | 6/1997 | (WO) . |
| WO9801428 | 1/1998 | (WO) . |
| WO9837075 | 8/1998 | (WO) . |

OTHER PUBLICATIONS

Takayasu Nagahara, et al; "Dibasic (Amidinoaryl) propanoic Acid Derivatives as Novel Blood Coagulation Factor Xa Inhibitors"; J. Med. Chem., Bd 37, 1994, pp. 1200–1207.

* cited by examiner

Primary Examiner—Mukund J. Shah
Assistant Examiner—Ben Schroeder
(74) Attorney, Agent, or Firm—R. P. Raymond; T. X. Witkowski; A. R. Stempel

(57) ABSTRACT

The present invention relates to new benzimidazoles of general formula

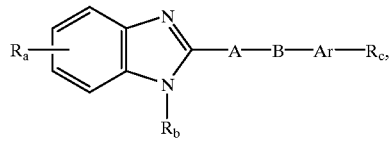

(I)

wherein $R_a$ to $R_c$, A, Ar and B are defined as in claim 1, the tautomers, the stereoisomers, the mixtures thereof the prodrugs, the derivatives thereof which contain a group which is negatively charged under physiological conditions, instead of a carboxy group, and the salts thereof, particularly the physiologically acceptable salts thereof with inorganic or organic acids or bases, which have valuable properties.

The compounds of the above general formula I wherein $R_c$ denotes a cyano group are valuable intermediates for preparing the other compounds of general formula I, and the compounds of the above general formula I wherein $R_c$ denotes one of the amidino groups mentioned in claim 1 which have valuable pharmacological properties, particularly an antithrombotic activity.

11 Claims, No Drawings

BENZIMIDAZOLES HAVING ANTITHROMBOTIC ACTIVITY

RELATED APPLICATIONS

Benefit of prior U.S. provisional application Ser. No. 60/092,215, filed Jul. 9, 1998, is hereby claimed.

DESCRIPTION OF THE INVENTION

The present invention relates to benzimidazoles of general formula

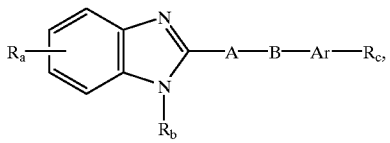

(I)

their tautomers, their stereoisomers, the mixtures thereof, their prodrugs, the derivatives thereof which contain a group which is negatively charged under physiological conditions instead of a carboxy group, and the salts thereof, particularly the physiologically acceptable salts thereof with inorganic or organic acids or bases which have valuable properties.

The compounds of the above general formula I wherein $R_c$ denotes a cyano group are valuable intermediates for preparing the other compounds of general formula I, and the compounds of the above general formula I wherein $R_c$ denotes one of the following amidino groups, as well as their tautomers, their stereoisomers, the mixtures thereof, their prodrugs, the derivatives thereof which contain a group which is negatively charged under physiological conditions instead of a carboxy group, and their salts, particularly the physiologically acceptable salts thereof with The present application thus relates to the new compounds of the above general formula I as well as the preparation thereof, the pharmaceutical compositions containing the pharmacologically active compounds, the preparation and use thereof.

In the above general formula

Ar denotes a phenylene or naphthylene group optionally substituted by a fluorine, chlorine or bromine atom, by a trifluoromethyl, $C_{1-3}$-alkyl or $C_{1-3}$-alkoxy group, a thienylene, thiazolylene, pyridinylene, pyrimidinylene, pyrazinylene or pyridazinylene group optionally substituted in the carbon skeleton by a $C_{1-3}$-alkyl group, A denotes a $C_{1-3}$-alkylene group, B denotes an oxygen or sulphur atom, a methylene, carbonyl, sulphinyl or sulphonyl group, an imino group optionally substituted by a $C_{1-3}$-alkyl group wherein the alkyl moiety may be mono- or disubstituted by a carboxy group, $R_a$ denotes an $R_1$—CO—$C_{3-5}$-cycloalkyl group wherein $R_1$ denotes a $C_{1-3}$-alkoxy, amino, $C_{1-4}$-alkylamino or di-($C_{1-4}$-alkyl)-amino group wherein each alkyl moiety may be substituted by a carboxy group, a 4- to 7-memberecl cycloalkyleneimino or cycloalkenyleneimino group which may be substituted by a hydroxy group or by one or two $C_{1-3}$-alkyl groups, whilst an alkyl substituent may simultaneously be substituted by a hydroxy, $C_{1-3}$-alkoxy, carboxy, carboxy-$C_{1-3}$-alkoxy, carboxy-$C_{1-3}$-alkylamino, N-($C_{1-3}$-alkyl)-N-(carboxy-$C_{1-3}$-allyl)-amino, carboxy-$C_{1-3}$-alkylaminocarbonyl, N-($C_{1-3}$-alkyl)-N-(carboxy-$C_{1-3}$-alkyl)-aminocarbonyl, carboxy-$C_{1-3}$-alkylaminocarbonylamino, 1-($C_{1-3}$-alkyl)-3-(carboxy-$C_{1-3}$-alkyl)-aminocarbonylamino, 3-($C_{1-3}$-alkyl)-3-(carboxy-$C_{1-3}$-alkyl)-aminocarbonylamino or 1,3-di-($C_{1-3}$-alkyl)-3-(carboxy-$C_{1-3}$-alkyl)-aminocarbonylamino group, a 4- to 7-membered cycloalkenyleneimino group substituted by a hydroxy group, a 5- to 7-membered cycloalkyleneimino group optionally substituted by a $C_{1-3}$-alkyl group, to which a phenyl ring is fused via two adjacent carbon atoms, a morpholino, piperazino, N-($C_{1-3}$-alkyl)-piperazino, pyrrolino, 3,4-dehydro-piperidino or pyrrol-1-yl group, an $R_2$-CX-$C_{3-5}$-cycloalkyl group wherein
$R_2$ denotes a phenyl, naphthyl or monocyclic 5- or 6-membered heteroaryl group optionally substituted by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group and an oxygen or sulphur atom or one or two nitrogen atoms and the abovementioned alkyl substituent may be substituted by a carboxy, carboxy-$C_{1-3}$-alkoxy, carboxy-$C_{1-3}$-alkylamino or N-($C_{1-3}$-alkyl)-carboxy-$C_{1-3}$-alkylamino group, and
X denotes an oxygen atom, a $C_{1-3}$-alkylimino, $C_{1-3}$-alkoxyimino, $C_{1-3}$-alkylhydrazino, di-($C_{1-3}$-alkyl)-hydrazino, $C_{2-4}$-alkanoyl-hydrazino, N-($C_{1-3}$-alkyl)-$C_{2-4}$-alkanoylhydrazino or $C_{1-3}$-alkylidene group each of which may be substituted in the alkyl or alkanoyl moiety or in the alkyl and alkanoyl moieties by a carboxy group, a $C_{1-3}$-alkyl or $C_{3-5}$-cycloalkyl group substituted by an imidazole or imidazolone group wherein
the imidazole ring may be substituted by a phenyl or carboxy group and by one or two $C_{1-3}$-alkyl groups or by one, two or three $C_{1-3}$-alkyl groups, wherein the substituents may be identical or different and one of the abovementioned alkyl substituents may simultaneously be substituted by a carboxy group or may be substituted in the 2 or 3 position by an amino, $C_{2-4}$-alkanoylamino, $C_{1-3}$-alkylamino, N-($C_{2-4}$-alkanoyl)-$C_{1-3}$-alkylamino or di-($C_{1-3}$-alkyl)-amino group, and
the imidazolone ring may be substituted by a $C_{1-3}$-alkyl group, whilst the alkyl substituent may be substituted by a carboxy group or in the 2 or 3 position by an amino, $C_{2-4}$-alkanoylamino, $C_{1-3}$-alkylamino, N-($C_{2-4}$-alkanoyl)-$C_{1-3}$-alkylamino or di-($C_{1-3}$-alkyl)-amino group, and
additionally a phenyl or pyridine ring may be fused to the abovementioned imidazole or imidazolone rings via two adjacent carbon atoms, an imidazolidine-2,4-dion-5-yl group which may be substituted by one or two $C_{1-3}$-alkyl groups, whilst at the same time an alkyl substituent may be substituted by a carboxy group, a $C_{1-4}$-alkyl group which is substituted
by a $C_{1-3}$-alkyl-$Y_1$-$C_{1-3}$-alkyl, HOOC-$C_{1-3}$-alkyl-$Y_1$-$C_{1-3}$-alkyl, tetrazolyl-$C_{1-3}$-alkyl-$Y_2$, $R_3NR_4$— or $R_3NR_4$-$C_{1-3}$-alkyl group and
by an isoxazolidinylcarbonyl group optionally substituted by a $C_{1-3}$-alkyl group, by a pyrrolino-carbonyl, 3,4- dehydropiperidinocarbonyl, pyrrol-1-yl-carbonyl, carboxy, aminocarbonyl, $C_{1-3}$-alkylaminocarbonyl, di-$(C_{1-3}$-alkyl)-aminocarbonyl or 4- to 7-membered cycloalkyleneiminocarbonyl group, whilst in the abovementioned groups the cycloalkyleneimino moiety may be substituted by one or two $C_{1-3}$-alkyl groups and at the same time each alkyl moiety or alkyl substituent in the abovementioned $C_{1-3}$-alkylaminocarbonyl, di-$(C_{1-3}$-alkyl)-aminocarbonyl or cycloalkyleneiminocarbonyl groups may be substituted by a carboxy group, and the remaining hydrogen atoms of the $C_{1-4}$-alkyl group may be wholly or partially replaced by fluorine atoms wherein $R_3$ denotes a hydrogen atom or a $C_{1-3}$-alkyl group optionally substituted by a carboxy group and $R_4$ denotes a hydrogen atom, a $C_{1-3}$-alkyl-$Y_1$-$C_{1-3}$-alkyl-$Y_2$, carboxy-$C_{1-3}$-alkyl-$Y_1$-$C_{1-3}$-alkyl-$Y_2$, $C_{1-3}$-alkyl-$Y_2$ or carboxy-$C_{1-3}$-alkyl-$Y_2$ group or $R_3$ and $R_4$ together with the nitrogen atom between them denote an 4- to 7-membered cycloalkyleneimino group optionally substituted by a carboxy, $C_{1-3}$-alkyl or carboxy-$C_{1-3}$-alkyl group wherein $Y_1$ denotes a carbon—carbon bond, an oxygen atom, a sulphenyl, sulphinyl, sulphonyl, —NH—, —NH—CO— or —NH—CO—NH— group and $Y_2$ denotes a carbon—nitrogen bond or a carbonyl, sulphonyl, imino or —NH—CO— group, wherein the carbonyl group of the —NH—CO— group is linked to the nitrogen atom of the $R_3NR_4$-group, and the imino groups occurring in the definition of the groups $Y_1$ and $Y_2$ may each additionally be substituted by a $C_{1-3}$-alkyl or carboxy-$C_{1-3}$-alkyl group, a $C_{1-3}$-alkyl or $C_{3-5}$-cycloalkyl group substituted by a $R_5NR_6$-group wherein $R_5$ denotes a hydrogen atom, a $C_{1-3}$-alkyl, $C_{5-7}$-cycloalkyl, phenylcarbonyl, phenylsulphonyl or pyridinyl group and $R_6$ denotes a $C_{1-3}$-alkyl, carboxy-$C_{1-3}$-alkyl or carboxy-$C_{1-3}$-alkylcarbonyl group, a $C_{1-3}$-alkyl group which is substituted by a $C_{2-4}$-alkanoyl or $C_{5-7}$-cycloalkanoyl group and by a $C_{1-3}$-alkyl group substituted by a chlorine, bromine or iodine atom, $R_b$ denotes a hydrogen atom or a $C_{1-3}$-alkyl group and $R_c$ denotes a cyano group or an amidino group optionally substituted by one or two $C_{1-3}$-alkyl groups.

The carboxy groups mentioned in the definitions of the abovementioned groups may also be replaced by a group which can be converted in vivo into a carboxy group or by a group which is negatively charged under physiological conditions, or the amino and imino groups mentioned in the definitions of the abovementioned groups may also be substituted by a group which can be cleaved in vivo. Groups of this kind are described, for example, in WO 98/46576 and by N. M. Nielson et al. in International Journal of Pharmaceutics 39, 75–85 (1987).

A group which can be converted in vivo into a carboxy group may be, for example, a hydroxymethyl group, a carboxy group esterified with an alcohol, wherein the alcoholic moiety is preferably a $C_{1-6}$-alkanol, a phenyl-$C_{1-3}$-alkanol, a $C_{3-9}$-cycloalkanol, whilst a $C_{5-8}$-cycloalkanol may additionally be substituted by one or two $C_{1-3}$-alkyl groups, a $C_{5-8}$-cycloalkanol wherein a methylene group in the 3- or 4-position is replaced by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-cycloalkyl-$C_{1-3}$-alkanol, a bicycloalkanol with a total of 8 to 10 carbon atoms, which may additionally be substituted in the bicycloalkyl moiety by one or two $C_{1-3}$-alkyl groups, a 1,3-dihydro-3-oxo-1-isobenzofuranol or an alcohol of formula

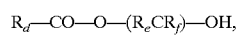

$$R_d-CO-O-(R_eCR_f)-OH,$$

wherein $R_d$ denotes a $C_{1-8}$-alkyl, $C_{5-7}$-cycloalkyl, phenyl or phenyl-$C_{1-3}$-alkyl group, $R_e$ denotes a hydrogen atom, a $C_{1-3}$-alkyl, $C_{5-7}$-cycloalkyl or phenyl group and $R_f$ denotes a hydrogen atom or a $C_{1-3}$-alkyl group, a group which is negatively charged under physiological conditions may be a tetrazol-5-yl, phenylcarbonylamino-carbonyl, trifluormethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and a group which can be cleaved in vivo from an imino or amino group may be, for example, a hydroxy group, an acyl group such as a benzoyl group optionally mono- or disubstituted by fluorine, chlorine, bromine or iodine atoms, by $C_{1-3}$-alkyl or $C_{1-3}$-alkoxy groups, wherein the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$-alkoxycarbonyl or $C_{1-16}$-alkylcarbonyloxy group wherein hydrogen atoms may be wholly or partially replaced by fluorine or chlorine atoms, such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkoxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl, $R_d$—CO—O—$(R_dCR_f)$—O—CO—, $C_{1-6}$-alkyl-CO—NH—$(R_gCR_h)$—O—CO— or $C_{1-6}$-alkyl-CO—O—$(R_gCR_h)$—$(R_gCR_h)$—O—CO— group wherein $R_d$ to $R_f$ are as hereinbefore defined, $R_g$ and $R_h$, which may be identical or different, denote hydrogen atoms or $C_{1-3}$-alkyl groups.

Moreover, the saturated alkyl and alkoxy moieties which contain more than 2 carbon atoms mentioned in the above definitions also include the branched isomers thereof, such as, for example, the isopropyl, tert.butyl, isobutyl group etc.

Preferred compounds are those of general formula

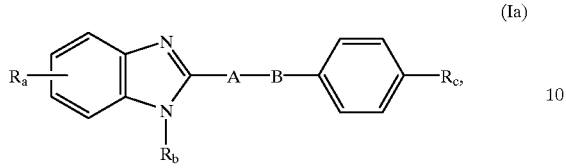

(Ia)

wherein

A denotes a $C_{1-3}$-alkylene group,

B denotes an oxygen or sulphur atom, a methylene, carbonyl, sulphinyl or sulphonyl group, an imino group optionally substituted by a $C_{1-3}$-alkyl group wherein the alkyl moiety may be mono- or disubstituted by a carboxy group, $R_a$ denotes an $R_1$—CO-$C_{3-5}$-cycloalkyl group wherein
  $R_1$ denotes a $C_{1-3}$-alkoxy, amino, $C_{1-4}$-alkylamino or di-($C_{1-4}$-alkyl)-amino group wherein each alkyl moiety may be substituted by a carboxy group,
  a 4- to 7-membered cycloalkyleneimino or cycloalkenyleneimino group which may be substituted by one or two $C_{1-3}$-alkyl groups, whilst an alkyl substituent may be simultaneously substituted by a hydroxy, $C_{1-3}$-alkoxy, carboxy, carboxy-$C_{1-3}$-alkoxy, carboxy-$C_{1-3}$-alkylamino, N-($C_{1-3}$-alkyl)-N-(carboxy-$C_{1-3}$-alkyl)-amino, carboxy-$C_{1-3}$-alkylaminocarbonyl, N-($C_{1-3}$-alkyl)-N-(carboxy-$C_{1-3}$-alkyl)-aminocarbonyl, carboxy-$C_{1-3}$-alkylaminocarbonylamino, 1-($C_{1-3}$-alkyl)-3-(carboxy-$C_{1-3}$-alkyl)-aminocarbonylamino, 3-($C_{1-3}$-alkyl)-3-(carboxy-$C_{1-3}$-alkyl)-aminocarbonylamino or 1,3-di-($C_{1-3}$-alkyl)-3-(carboxy-$C_{3}$-alkyl)-aminocarbonylamino group,
  a 4- to 7-membered cycloalkenyleneimino group substituted by a hydroxy group,
  a 5- to 7-membered cycloalkyleneimino group optionally substituted by a $C_{1-3}$-alkyl group, to which a phenyl ring is fused via two adjacent carbon atoms,
  a morpholino, piperazino, N-($C_{1-3}$-alkyl)-piperazino, pyrrolino, 3,4-dehydro-piperidino or pyrrol-1-yl group, an $R_2$—CX-$C_{3-5}$-cycloalkyl group wherein
  $R_2$ denotes a phenyl, naphthyl or monocyclic 5- or 6-membered heteroaryl group optionally substituted by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group and an oxygen or sulphur atom or one or two nitrogen atoms and the abovementioned alkyl substituent may be substituted by a carboxy, carboxy-$C_{1-3}$-alkoxy, carboxy-$C_{1-3}$-alkylamino or N-($C_{1-3}$-alkyl)-carboxy-$C_{1-3}$-alkylamino group, and
  X denotes an oxygen atom, a $C_{1-3}$-alkylimino, $C_{1-3}$-alkoxyimino, $C_{1-3}$-alkylhydrazino, di-($C_{1-3}$-alkyl)-hydrazino, $C_{2-4}$-alkanoylhydrazino, N-($C_{1-3}$-alkyl)-$C_{2-4}$-alkanoylhydrazino or $C_{1-3}$-alkylidene group each of which may be substituted in the alkyl or alkanoyl moiety or in the alkyl and alkanoyl moieties by a carboxy group, a $C_{1-3}$-alkyl or $C_{3-5}$-cycloalkyl group substituted by an imidazole or imidazolone group wherein
  the imidazole ring may be substituted by a phenyl or carboxy group and by one or two $C_{1-3}$-alkyl groups or by one, two or three $C_{1-3}$-alkyl groups, wherein the substituents may be identical or different and one of the abovementioned alkyl substituents may simultaneously be substituted by a carboxy group or may be substituted in the 2 or 3 position by an amino, $C_{2-4}$-alkanoylamino, $C_{1-3}$-alkylamino, N-($C_{2-4}$-alkanoyl)-$C_{1-3}$-alkylamino or di-($C_{1-3}$-alkyl)-amino group, and
  the imidazolone ring may be substituted by a $C_{1-3}$-alkyl group, whilst the alkyl substituent may be substituted by a carboxy group or in the 2 or 3 position by an amino, $C_{2-4}$-alkanoylamino, $C_{1-3}$-alkylamino, N-($C_{2-4}$-alkanoyl)-$C_{1-3}$-alkylamino or di-($C_{1-3}$-alkyl)-amino group, and
  additionally a phenyl or pyridine ring may be fused to the abovementioned imidazole or imidazolone rings via two adjacent carbon atoms, an imidazolidine-2,4-dion-5-yl group which may be substituted by one or two $C_{1-3}$-alkyl groups, whilst at the same time an alkyl substituent may be substituted by a carboxy group, a $C_{1-4}$-alkyl group which is substituted
  by a $C_{1-3}$-alkyl-$Y_1$-$C_{1-3}$-alkyl, HOOC-$C_{1-3}$-alkyl-$Y_1$-$C_{1-3}$-alkyl, tetrazolyl-$C_{1-3}$-alkyl-$Y_2$, $R_3NR_4$— or $R_3NR_4$-$C_{1-3}$-alkyl group and
  by an isoxazolidinylcarbonyl group optionally substituted by a $C_{1-3}$-alkyl group, by a pyrrolinocarbonyl, 3,4-dehydro-piperidinocarbonyl, pyrrol-1-yl-carbonyl, carboxy, aminocarbonyl, $C_{1-3}$-alkylaminocarbonyl, di-($C_{1-3}$-alkyl)-aminocarbonyl or 4- to 7-membered cycloalkyleneiminocarbonyl group, whilst in the abovementioned groups the cycloalkyleneimino moiety may be substituted by one or two $C_{1-3}$-alkyl groups and at the same time each alkyl moiety or alkyl substituent in the abovementioned $C_{1-3}$-alkylaminocarbonyl, di-($C_{1-3}$-alkyl)-aminocarbonyl or cycloalkyleneiminocarbonyl groups may be substituted by a carboxy group, and the remaining hydrogen atoms of the $C_{1-4}$-alkyl group may be wholly or partially replaced by fluorine atoms wherein
    $R_3$ denotes a hydrogen atom or a $C_{1-3}$-alkyl group optionally substituted by a carboxy group and
    $R_4$ denotes a hydrogen atom, a $C_{1-3}$-alkyl-$Y_1$-$C_{1-3}$-alkyl-$Y_2$, carboxy-$C_{1-3}$-alkyl-$Y_1$-$C_{1-3}$-alkyl-$Y_2$, $C_{1-3}$-alkyl-$Y_2$ or carboxy-$C_{1-3}$-alkyl-$Y_2$ group or
    $R_3$ and $R_4$ together with the nitrogen atom between them denote an 4- to 7-membered cycloalkyleneimino group optionally substituted by a carboxy, $C_{1-3}$-alkyl or carboxy-$C_{1-3}$-alkyl group wherein
  $Y_1$ denotes a carbon—carbon bond, an oxygen atom, a sulphenyl, sulphinyl, sulphonyl, —NH—, —NH—CO— or —NH—CO—NH— group and $Y_2$ denotes a carbon—nitrogen bond or a carbonyl, sulphonyl, imino or —NH—CO— group, wherein the carbonyl group of the —NH—CO— group is linked to the nitrogen atom of the $R_3NR_4$— group, and the imino groups occurring in the definition of the groups $Y_1$ and $Y_2$ may each additionally be substituted by a $C_{1-3}$-alkyl or carboxy-$C_{1-3}$-alkyl group, a $C_{1-3}$-alkyl or $C_{3-5}$-cycloalkyl group substituted by a $R_5NR_6$— group wherein
  $R_5$ denotes a hydrogen atom, a $C_{1-3}$-alkyl, $C_{5-7}$-cycloalkyl, phenylcarbonyl, phenylsulphonyl or pyridinyl group and $R_6$ denotes a $C_{1-3}$-alkyl, carboxy-$C_{1-3}$-alkyl or carboxy-$C_{1-3}$-alkylcarbonyl group, a $C_{1-3}$-alkyl group which is substituted by a $C_{2-4}$-alkanoyl or $C_{5-7}$-cycloalkanoyl group and by a $C_{1-3}$-alkyl group substituted by a chlorine, bromine or iodine atom, $R_b$ denotes a hydrogen atom or a $C_{1-3}$-alkyl group and $R_c$ denotes a cyano group or an amidino group which may be substituted by a hydroxy group, by one or two $C_{1-3}$-alkyl groups, or by one or two $C_{1-8}$-alkoxycarbonyl groups, wherein the carboxy, amino and imino groups mentioned in the definition of the abovementioned groups may also be substituted by a group which can be cleaved in vivo, the tautomers, stereoisomers and salts thereof.

Particularly preferred compounds of the above general formula Ia are those wherein A denotes a $C_{1-3}$-alkylene group, B denotes an oxygen atom, a methylene, imino or N-($C_{1-3}$-alkyl)-imino group wherein the alkyl moiety may be substituted by a carboxy group, $R_a$ denotes an $C_{3-5}$-cycloalkyl group substituted by the $R_1$—CO group in the 1 position wherein $R_1$ denotes a $C_{1-3}$-alkoxy, amino, $C_{1-4}$-alkylamino or di-($C_{1-4}$-alkyl)-amino group wherein each alkyl moiety may be substituted by a carboxy group, a 4- to 7-membered cycloalkyleneimino group which may be substituted by a hydroxy group or by one or two $C_{1-3}$-alkyl groups, whilst an alkyl substituent may simultaneously be substituted by a hydroxy, $C_{1-3}$-alkoxy, carboxy, carboxy-$C_{1-3}$-alkoxy, carboxy-$C_{1-3}$-alkylamino, N-($C_{1-3}$-alkyl)-N-(carboxy-$C_{1-3}$-alkyl)-amino, carboxy-$C_{1-3}$-alkylaminocarbonyl, N-($C_{1-3}$-alkyl)-N-(carboxy-$C_{1-3}$-alkyl)-aminocarbonyl, carboxy-$C_{1-3}$-alkylamino-carbonylamino, 1-($C_{1-3}$-alkyl)-3-(carboxy-$C_{1-3}$-alkyl)-aminocarbonylamino, 3-($C_{1-3}$-alkyl)-3-(carboxy-$C_{1-3}$-alkyl)-aminocarbonylamino or 1,3-di-($C_{1-3}$-alkyl)-3-(carboxy-$C_{1-3}$-alkyl)-aminocarbonylamino group, a 5- to 7-membered cycloalkyleneimino group optionally substituted by a $C_{1-3}$-alkyl group, to which a phenyl ring is fused via two adjacent carbon atoms, a morpholino, piperazino, N-($C_{1-3}$-alkyl)-piperazino, pyrrolino, 3,4-dehydro-piperidino or pyrrol-1-yl group, a $C_{3-5}$-cycloalkyl group substituted in the 1 position by the $R_2$—CX— group, wherein R2 denotes a phenyl, naphthyl or monocyclic 5- or 6-membered heteroaryl group optionally substituted by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group and an oxygen or sulphur atom or one or two nitrogen atoms and the abovementioned alkyl substituent may be substituted by a carboxy, carboxy-$C_{1-3}$-alkoxy, carboxy-$C_{1-3}$-alkylamino or N-($C_{1-3}$-alkyl)-carboxy-$C_{1-3}$-alkylamino group, and X denotes an oxygen atom, a $C_{1-3}$-alkylimino, $C_{1-3}$-alkoxyimino or $C_{1-3}$-alkylidene group, each of which may be substituted in the alkyl or alkanoyl moiety by a carboxy group, a $C_{1-3}$-alkyl group substituted in the 1 position by an imidazole or imidazolone group wherein the imidazole ring may be substituted by a phenyl or carboxy group and by one or two $C_{1-3}$-alkyl groups or by one, two or three $C_{1-3}$-alkyl groups, wherein the substituents may be identical or different and one of the abovementioned alkyl substituents may simultaneously be substituted by a carboxy group or may be substituted in the 2 or 3 position by an amino, $C_{2-4}$-alkanoylamino, $C_{1-3}$-alkylamino, N-($C_{2-4}$-alkanoyl)-$C_{1-3}$-alkylamino or di-($C_{1-3}$-alkyl)-amino group, and the imidazolone ring may be substituted by a $C_{1-3}$-alkyl group, whilst the alkyl substituent may be substituted by a carboxy group or in the 2 or 3 position by an amino, $C_{2-4}$-alkanoylamino, $C_{1-3}$-alkylamino, N-($C_{2-4}$-alkanoyl)-$C_{1-3}$-alkylamino or di-($C_{1-3}$-alkyl)-amino group, and additionally a phenyl or pyridine ring may be fused to the abovementioned imidazole or imidazolone rings via two adjacent carbon atoms, an imidazolidine-2,4-dtion-5-yl group which may be substituted by one or two $C_{1-3}$-alkyl groups, whilst at the same time an alkyl substituent may be substituted by a carboxy group, a $C_{1-4}$-alkyl group which is substituted in the 1 position by an $R_3NR_4$— or $R_3NR_4$-$C_{1-3}$-alkyl group and by a pyrrolinocarbonyl, 2,3-dehydro-piperidinocarbonyl, imidazol-1-yl-carbonyl, carboxy, aminocarbonyl, $C_{1-3}$-alkylaminocarbonyl, di-($C_{1-3}$-alkyl)-aminocarbonyl, isoxazolidin-1-yl-carbonyl or 4- to 7-membered cycloalkyleneiminocarbonyl group, whilst in the abovementioned groups the cycloalkyleneimino moiety may be substituted by one or two $C_{1-3}$-alkyl groups and at the same time each alkyl moiety or alkyl substituent in the abovementioned $C_{1-3}$-alkylaminocarbonyl, di-($C_{1-3}$-alkyl)-aminocarbonyl or cycloalkyleneiminocarbonyl groups may be substituted by a carboxy group, and the remaining hydrogen atoms of the $C_{1-4}$-alkyl group may be wholly or partially replaced by fluorine atoms, wherein $R_3$ denotes a hydrogen atom or a $C_{1-3}$-alkyl group optionally substituted by a carboxy group and $R_4$ denotes a hydrogen atom, a $C_{1-3}$-alkyl-$Y_2$ or carboxy-$C_{1-3}$-alkyl-$Y_2$ group or $R_3$ and $R_4$ together with the nitrogen atom between them denote a 4- to 7-membered cycloalkyleneimino group optionally substituted in the 1 position by a carboxy, $C_{1-3}$-alkyl or carboxy-$C_{1-3}$-alkyl group, wherein $Y_2$ denotes a carbon—nitrogen bond or a carbonyl, imino or —NH—CO— group, wherein the carbonyl group of the —NH—CO— group is linked to the nitrogen atom of the $R_3NR_4$— group, and the imino group occurring in the definition of the groups $Y_2$ may additionally be substituted by a $C_{1-3}$-alkyl or carboxy-$C_{1-3}$-alkyl group, a $C_{1-3}$-alkyl or $C_{3-5}$-cycloalkyl group substituted in the 1 position by an $R_5NR_6$— group, wherein $R_5$ denotes a hydrogen atom, a $C_{1-3}$-alkyl, $C_{5-7}$-cycloalkyl, phenylcarbonyl, phenylsulphonyl or pyridinyl group and $R_6$ denotes a $C_{1-3}$-alkyl, carboxy-$C_{1-3}$-alkyl or carboxy-$C_{1-3}$-alkylcarbonyl group, a $C_{1-3}$-alkyl group which is substituted by a $C_{2-4}$-alkanoyl or $C_{5-7}$-cycloalkanoyl group and by a $C_{1-3}$-alkyl group substituted by a chlorine, bromine or iodine atom, $R_b$ denotes a $C_{1-3}$-alkyl group and $R_c$ denotes an amidino group which may optionally be substituted by a 2,2,2-trichloroethoxycarbonyl, $C_{1-8}$-alkoxycarbonyl, acetoxymethyloxycarbonyl, benzyloxycarbonyl or benzoyl group, whilst the benzoyl moiety may be mono- or disubstituted by fluorine, chlorine, bromine or iodine atoms, by $C_{1-3}$-alkyl or $C_{1-3}$-alkoxy groups and the substituents may be identical or different, the $C_{1-3}$-alkanol esters, the tautomers, stereoisomers and salts thereof.

Most particularly preferred compounds of general formula I are those wherein

A denotes a methylene group,

B denotes an oxygen atom or an imino group, $R_a$ denotes a cyclopropyl group substituted by the $R_1$—CO— group in the 1 position, wherein $R_1$ denotes a pyrrolidino or piperidino group optionally substituted by a methyl or ethyl group wherein each methyl or ethyl moiety may be substituted by a carboxy, carboxy-$C_{1-3}$-alkoxy, carboxy-$C_{1-3}$-alkylamino or N-($C_{1-3}$-alkyl)-carboxy-$C_{1-3}$-alkylamino group, a cyclopropyl group substituted in the 1 position by the $R_2$—CX— group, wherein $R_2$ denotes a phenyl, pyridyl, pyrazolyl group optionally substituted by a $C_{1-3}$-alkyl group and X denotes an oxygen atom, a $C_{1-3}$-alkoxyimino or $C_{1-3}$-alkylidene group, each of which is substituted in the alkyl or alkoxy moiety by a carboxy group, a $C_{1-2}$-alkyl group substituted in the 1 position by an imidazole group wherein the imidazole ring may be substituted by a phenyl or carboxy group and by one or two $C_{1-3}$-alkyl groups or by one, two or three $C_{1-3}$-alkyl groups, wherein the substituents may be identical or different and one of the abovementioned alkyl substituents may simultaneously be substituted by a carboxy group or may be substituted in the 2 or 3 position by an amino, $C_{2-4}$-alkanoylamino, $C_{1-3}$-alkylamino, N-($C_{2-4}$-alkanoyl)-$C_{1-3}$-alkylamino or di-($C_{1-3}$-alkyl)-amino group, whilst additionally a phenyl or pyridine ring may be fused to the abovementioned imidazole rings via two adjacent carbon atoms, a $C_{1-2}$-alkyl substituted in the 1 position by a benzimidazolon-1-yl group, whilst the imidazolone ring may be substituted by a methyl or ethyl group optionally substituted by a carboxy group, a methyl or ethyl group which is substituted in the 1 position by an $R_3NR_4$— or $R_3NR_4$-$C_{1-3}$-alkyl group and by a di-($C_{1-3}$-alkyl)-aminocarbonyl group, by an isoxazolidin-1-yl-carbonyl group, by a pyrrolidinocarbonyl or piperidino-carbonyl group substituted by a $C_{1-3}$-alkyl group, whilst in the abovementioned groups each alkyl moiety or alkyl substituent in the abovementioned groups may be substituted by a carboxy group, wherein $R_3$ denotes a hydrogen atom or a $C_{1-3}$-alkyl group optionally substituted by a carboxy group and $R_4$ denotes a hydrogen atom, a $C_{1-3}$-alkyl-$Y_2$ or carboxy-$C_{1-3}$-alkyl-$Y_2$ group or $R_3$ and $R_4$ together with the nitrogen atom between them denote a 4- to 7-membered cycloalkyleneimino group optionally substituted by a carboxy group, wherein $Y_2$ denotes a carbon—nitrogen bond, a carbonyl group or an imino group optionally substituted by a $C_{1-3}$-alkyl group, a $C_{1-2}$-alkyl group substituted in the 1 position by an $R_5NR_6$— group, wherein $R_5$ denotes a pyridinyl, phenylcarbonyl or phenylsulphonyl group and $R_6$ denotes a $C_{1-3}$-alkyl or carboxy-$C_{1-3}$-alkyl group, an n-propyl group substituted in the 3 position by a chlorine atom, which is substituted in the 1 position by a cyclopentylcarbonyl group, a cyclopropyl group substituted in the 1 position by a cyclopentylamino group, which is substituted at the nitrogen atom by a carboxy-$C_{1-3}$-alkylcarbonyl group, $R_b$ denotes a methyl group and $R_c$ denotes an amidino group which may optionally be substituted by a $C_{1-8}$-alkoxycarbonyl, acetoxymethyloxycarbonyl, 2,2,2-trichloroethoxycarbonyl, benzyloxycarbonyl or benzoyl group, particularly those compounds of general formula Ia wherein A denotes a methylene group, B denotes an imino group, $R_a$ denotes a cyclopropyl group substituted by the $R_1$—CO— group in the 1 position, wherein $R_1$ denotes a pyrrolidino or piperidino group optionally substituted by a methyl or ethyl group wherein each methyl or ethyl moiety may be substituted by a carboxy, carboxy-$C_{1-3}$-alkoxy, carboxy-$C_{1-3}$-alkylamino or N-($C_{1-3}$-alkyl)-carboxy-$C_{1-3}$-alkylamino group, a cyclopropyl group substituted in the 1 position by the $R_2$—CX group, wherein $R_2$ denotes a phenyl, pyridyl, pyrazolyl group optionally substituted by a $C_{1-3}$-alkyl group and X denotes an oxygen atom, a $C_{1-3}$-alkoxyimino or $C_{1-3}$-alkylidene group, each of which is substituted in the alkyl or alkoxy moiety by a carboxy group, a $C_{1-2}$-alkyl group substituted in the 1 position by an imidazole group wherein the imidazole ring may be substituted by one to three methyl groups or by two methyl groups and an ethyl group, whilst additionally one of the abovementioned methyl or ethyl substituents may simultaneously be substituted by a carboxy group, a methyl or ethyl group which is substituted in the 1 position by an $R_3NR_4$— or $R_3NR_4$—$CH_2$— group and by a di-($C_{1-3}$-alkyl)-aminocarbonyl, by a pyrrolidinocarbonyl or piperidinocarbonyl group optionally substituted by a $C_{1-3}$-alkyl group, whilst in the abovementioned groups each alkyl moiety or alkyl substituent may be substituted by a carboxy group, wherein $R_3$ denotes a hydrogen atom or a $C_{1-3}$-alkyl group optionally substituted by a carboxy group and $R_4$ denotes a $C_{1-3}$-alkyl-$Y_2$ or carboxy-$C_{1-3}$-alkyl-$Y_2$ group wherein $Y_2$ denotes a carbon—nitrogen bond, a carbonyl group or an imino group optionally substituted by a $C_{1-3}$-alkyl group, $R_b$ denotes a methyl group and $R_c$ denotes an amidino group which may optionally be substituted by a $C_{1-8}$-alkoxycarbonyl, acetoxymethyloxycarbonyl, 2,2,2-trichloroethoxycarbonyl, benzyloxycarbonyl or benzoyl group, whilst the abovementioned compounds in which the group $R_a$ is in the 5 position are particularly preferred, the $C_{1-3}$-alkanol esters, the tautomers, stereoisomers and salts thereof.

The following are mentioned as examples of particularly preferred compounds:

(a) 2-(4-amidinophenylaminomethyl)-1-methyl-5-[1-(pyrrolidin-1-yl-carbonyl)-cyclopropyl]-benzimidazole, (b) (E/Z)-2-(4-amidinophenylaminomethyl)-1-methyl-5-[1-[(pyridin-2-yl)-(carboxymethyloxyimino)methylene]-cyclopropyl]-benzimidazole, (c) 2-(4-amidinophenylaminomethyl)-1-methyl-5-[1-(2-carboxyethylamino)-1-(pyrrolidin-1-yl-carbonyl)-ethyl]-benzimidazole, (d) 2-(4-amidinophenylaminomethyl)-1-methyl-5-[1-[2-(2-carboxyethyl)-pyrrolidin-1-yl-carbonyl]cyclopropyl]-benzimidazole, (e) 2-(4-amidinophenylaminomethyl)-1-methyl-5-[2-(2-carboxyethyl)-4,5-dimethyl-imidazol-1-yl-methyl]-benzimidazole (f) 2-(4-amidinophenylaminomethyl)-1-methyl-5-[1-(carboxymethylamino)-1-(pyrrolidin-1-yl-carbonyl)-ethyl]-benzimidazole and (g) 2-(4-amidinophenylaminomethyl)-1-methyl-5-[1-(N-methylcarboxymethylcarbonylaminomethyl)-1-methyl-1-(pyrrolidin-1-yl-carbonyl)-ethyl]-benzimidazole and the $C_{1-3}$-alkanol esters, the N-($C_{1-8}$-alkoxycarbonyl), N-benzyloxycarbonyl and N-benzoyl-amidines, the tautomers, stereoisomers and salts thereof.

According to the invention, the compounds of general formula I are prepared by methods known per se, for example by the following methods:

a) In order to prepare a compound of general formula I wherein R, denotes a cyano group:
cyclising a compound of general formula

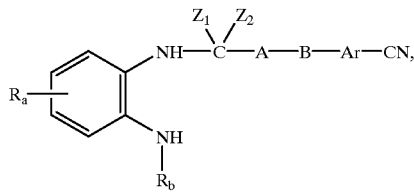

(II)

optionally formed in the reaction mixture,
wherein
$R_a$, $R_b$, Ar, A and B are as hereinbefore defined, $Z_1$ and $Z_2$, which may be identical or different, denote amino, hydroxy or mercapto groups optionally substituted by alkyl groups with 1 to 6 carbon atoms or $Z_1$ and $Z_2$ together represent an oxygen or sulphur atom, an imino group optionally substituted by an alkyl group with 1 to 3 carbon atoms, an alkylendioxy or alkylenedithio group with 2 or 3 carbon atoms.

The cyclisation is expediently carried out in a solvent or mixture of solvents such as ethanol, isopropanol, glacial acetic acid, benzene, chlorobenzene, toluene, xylene, glycol, glycol monomethylether, diethyleneglycol dimethylether, sulpholane, dimethylformamide, tetraline or in an excess of the acylating agent used to prepare the compound of general formula II, e.g. in the corresponding nitrile, anhydride, acid halide, ester or amide, for example at temperatures between 0 and 250° C., but preferably at the boiling temperature of the reaction mixture, optionally in the presence of a condensing agent such as phosphorus oxychloride, thionyl chloride, sulphuryl chloride, sulphuric acid, p-toluenesulphonic acid, methanesulphonic acid, hydrochloric acid, phosphoric acid, polyphosphoric acid, acetic acid, acetic anhydride, N,N-dicyclohexyl-carbodiimide or optionally in the presence of a base such as potassium ethoxide or potassium tert.butoxide. However, the cyclisation may also be carried out without a solvent and/or condensing agent.

It is particularly advantageous to perform the reaction by preparing a compound of general formula II in the reaction mixture by reduction of a corresponding o-nitro compound optionally in the presence of a carboxylic acid of general formula

HO—C—A—B—Ar—CN    (III), wherein

Ar, A and B are as hereinbefore defined, by acylation of a corresponding amino compound optionally formed in the reaction mixture.

b) In order to prepare a compound of general formula I wherein $R_a$ denotes a $R_2$—CX'—$C_{3-5}$-cycloalkylene group, wherein $R_2$ is as hereinbefore defined and X' denotes one of the imino groups mentioned for X hereinbefore:

reacting a compound of general formula

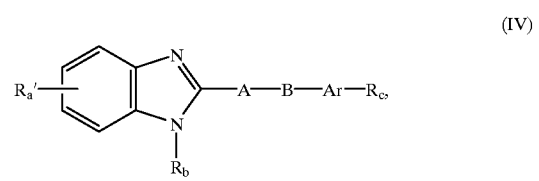

(IV)

wherein $R_b$, $R_c$, Ar, A and B are as hereinbefore defined and $R_a'$ denotes an $R_2$—CO—$C_{3-5}$-cycloalkylene group, where $R_2$ is as hereinbefore defined, with an amine of general formula

$H_2X'$    (V), wherein

X' denotes one of the imino groups mentioned for X hereinbefore.

The reaction is preferably carried out in a solvent such as methanol/toluene, ethanol, isopropanol or xylene and expediently in the presence of a dehydrating agent such as molecular sieve, sodium sulphate or calcium chloride optionally in the presence of a base such as triethylamine at temperatures between 50 and 100° C., preferably at the boiling temperature of the reaction mixture.

c) In order to prepare a compound of general formula I wherein $R_a$ denotes a $R_2$—CX''-$C_{3-5}$-cycloalkylene group, wherein $R_2$ is as hereinbefore defined and X'' denotes one of the alkylidene groups mentioned for X hereinbefore:

reacting a compound of general formula

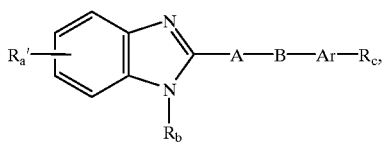

(IV)

wherein $R_b$, $R_c$, Ar, A and B are as hereinbefore defined and $R_a'$ denotes an $R_2$—CO-$C_{3-5}$-cycloalkylene group, where $R_2$ is as hereinbefore defined, with a phosphone of general formula $$Z_3—HX'' \quad (VI),$$

wherein

X" denotes one of the alkylidene groups mentioned for X hereinbefore and $Z_3$ denotes a triphenylphosphono or di-($C_{1-3}$-alkoxy) phosphono group such as the triethoxyphosphono group.

The reaction is preferably carried out under protective gas in a solvent such as tetrahydrofuran, dimethylformamide, dioxane, diethylether or dimethyl sulphoxide in the presence of a base such as potassium tert.butoxide, sodium ethoxide or sodium hydride at temperatures between −25 and 50° C., preferably at temperatures between −15° and ambient temperature.

d) In order to prepare a compound of general formula I wherein $R_c$ denotes an amiaino group which may be substituted by one or two $C_{1-3}$-alkyl groups:

reacting a compound of general formula

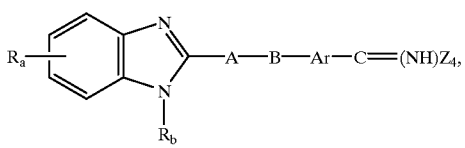

(VII)

optionally formed in the reaction mixture
wherein $R_a$, $R_b$, Ar, A and B are as hereinbefore defined and $Z_4$ denotes an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group, with an amine of general formula $$H—R_7NR_8, \quad (VIII)$$

wherein $R_7$ and $R_8$, which may be identical or different, each denote a hydrogen atom or a $C_{1-3}$-alkyl group, or with the salts thereof.

The reaction is expediently carried out in a solvent such as methanol, ethanol, n-propanol, tetrahydrofuran or dioxane at temperatures between 0 and 150° C., preferably at temperatures between 0 and 80° C., with an amine of general formula VIII or with a corresponding acid addition salt such as for example ammonium carbonate or ammonium acetate.

A compound of general formula VII is obtained for example by reacting a corresponding cyano compound with a corresponding alcohol such as methanol, ethanol, n-propanol, isopropanol or benzyl alcohol in the presence of an acid such as hydrochloric acid or by reacting a corresponding amide with a trialkyloxonium salt such as triethyloxonium-tetrafluoroborate in a solvent such as methylene chloride, tetrahydrofuran or dioxane at temperatures between 0 and 50° C., but preferably at 20° C., or a corresponding nitrile with hydrogen sulphide expediently in a solvent such as pyridine or dimethylformamide and in the presence of a base such as triethylamine and subsequently alkylating the thioamide formed with a corresponding alkyl or aralkyl halide.

e) In order to prepare a compound of general formula I wherein $R_a$ denotes an imidazolidin-2,4-dion-5-yl group which may be substituted by one or two $C_{1-3}$-alkyl groups, whilst at the same time an alkyl substituent may be substituted by a carboxy or $C_{1-3}$-alkoxycarbonyl group:

cyclising a compound of general formula

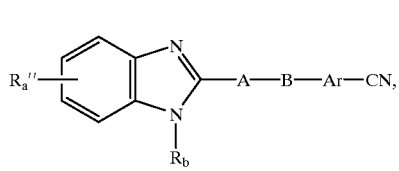

(IX)

optionally formed in the reaction mixture
wherein $R_b$, Ar, A and B are as hereinbefore defined and $R_a''$ denotes an aminocarbonylamino group, substituted in the 3 position by a $C_{1-3}$-alkoxycarbonyl-$C_{1-3}$-alkyl group.

The reaction is preferably carried out in a solvent such as methanol, ethanol, n-propanol, isopropanol or benzyl alcohol in the presence of an acid such as hydrochloric acid at temperatures between 0 and 50° C., but preferably at 20° C.

f) In order to prepare a compound of general formula I wherein $R_c$ denotes a hydroxyamidino group:

reacting a nitrite of general formula

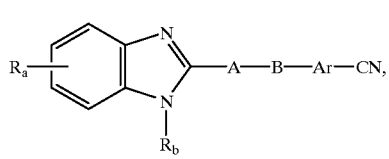

(X)

wherein $R_a$, $R_b$, Ar, A and B are as hereinbefore defined, with hydroxylamine or the salts thereof.

The reaction is expediently carried out in a solvent such as methanol, ethanol, n-propanol, water, methanol/water, tetrahydrofuran, tetrahydrofuran/water, dioxane or dioxane/water at temperatures between 0 and 150° C., preferably at temperatures between 0 and 80° C.

g) In order to prepare a compound of general formula I wherein $R_a$ contains a carboxy group and $R_c$ is as hereinbefore defined or $R_a$ is as hereinbefore defined and R, denotes an amidino group optionally substituted by a hydroxy group or by one or two $C_{1-3}$-alkyl groups:

converting a compound of general formula

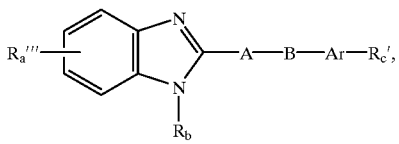

(XI)

wherein
- $R_b$, Ar, A and B are as hereinbefore defined and $R_a'''$ and $R_c'$ have the meanings given for $R_a$ and $R_c$ with the proviso that $R_a$ contains a group which may be converted into a carboxy group by hydrolysis, treatment with an acid or base, thermolysis or hydrogenolysis and $R_c$ is as hereinbefore defined or $R_c$ denotes a group which may optionally be converted by hydrolysis, treatment with an acid or base, thermolysis or hydrogenolysis into an amidino group substituted by a hydroxy group or by one or two $C_{1-3}$-alkyl groups and $R_a$ is as hereinbefore defined,
- is converted by hydrolysis, treatment with an acid or base, thermolysis or hydrogenolysis into a compound of general formula I wherein $R_a$ contains a carboxy group and $R_c$ is as hereinbefore defined or $R_a$ is as hereinbefore defined and $R_c$ denotes an amidino group optionally substituted by a hydroxy group or by one or two $C_{1-3}$-alkyl groups.

A group which may be converted into a carboxy group might be, for example, a carboxyl group protected by a protecting group, such as the functional derivatives thereof, e.g. the unsubstituted or substituted amides, esters, thioesters, trimethylsilylesters, orthoesters or iminoesters thereof which are expediently converted by hydrolysis into a carboxyl group, the esters thereof with tertiary alcohols, e.g. the tert.butyl ester, which are expediently converted into a carboxyl group by treatment with an acid or thermolysis, and the esters thereof with aralkanols, e.g. the benzylester, which are expediently converted into a carboxyl group by hydrogenolysis.

The hydrolysis is expediently carried out either in the presence of an acid such as hydrochloric acid, sulphuric acid, phosphoric acid, acetic acid, trichloroacetic acid, trifluoroacetic acid or the mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10 and 120° C., e.g. at temperatures between ambient temperature and the boiling temperature of the reaction mixture.

If a compound of formula XI for example contains the tert.butyl or tert.butyloxycarbonyl group, these may also be cleaved by treatment with an acid such as trifluoroacetic acid, formic acid, p-toluenesulphonic acid, sulphuric acid, hydrochloric acid, phosphoric acid or polyphosphoric acid optionally in an inert solvent such as methylene chloride, chloroform, benzene, toluene, diethylether, tetrahydrofuran or dioxane preferably at temperatures between −10 and 120° C., e.g. at temperatures between 0 and 60° C., or thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40 and 120° C.

If a compound of formula XI contains, for example, a benzyloxy or benzyloxycarbonyl group, these may also be cleaved hydrogenolytically in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0 and 50° C., e.g. at ambient temperature, and at a hydrogen pressure of from 1 to 5 bar.

h) In order to prepare a compound of general formula I wherein $R_c$ denotes an amidino group which is substituted by one or two $C_{1-8}$-alkoxycarbonyl groups or by a group which can be cleaved in vivo:

reacting a compound of general formula I

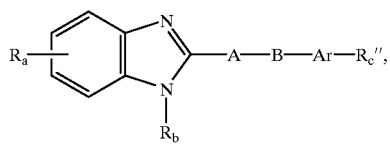

(XII)

wherein
- $R_a$, $R_b$, Ar, A and B are as hereinbefore defined and
- $R_c''$ denotes an amidino group, with a compound of general formula $$Z_5—R_9 \quad \text{(XIII)},$$

wherein
- $R_9$ denotes a $C_{1-8}$-alkoxycarbonyl group or the acyl group of one of the groups which can be cleaved in vivo mentioned hereinbefore and
- $Z_5$ denotes a nucleofugic leaving group such as a halogenatom, e.g. a chlorine, bromine or iodine atom, or a p-nitrophenyl group.

The reaction is preferably carried out in a solvent such as methanol, ethanol, methylene chloride, tetrahydrofuran, toluene, dioxane, dimethyl sulphoxide or dimethylformamide optionally in the presence of an inorganic or a tertiary organic base, preferably at temperatures between 20° C. and the boiling temperature of the solvent used.

With a compound of general formula XIII wherein $Z_5$ denotes a nucleofugic leaving group, the reaction is preferably carried out in a solvent such as methylene chloride, acetonitrile, tetrahydrofuran, toluene, acetone/water, dimethylformamide or dimethyl sulphoxide, optionally in the presence of a base such as sodium hydride, potassium carbonate, potassium tert.butoxide or N-ethyl-diisopropylamine at temperatures between 0 and 60° C.

If according to the invention a compound of general formula I is obtained which contains a $(R_3NR_4)$-$C_{1-3}$-alkyl group wherein at least one of the groups $R_3$ or $R_4$ denotes a hydrogen atom, this may subsequently be converted with a corresponding isocyanate or carbamoyl halide into a corresponding urea compound of general formula I and/or if a compound of general formula I is obtained which contains an $NH_2$-$C_{1-3}$-alkyl group, this may subsequently be converted with a corresponding acrylic acid ester into a corresponding 2-($C_{1-3}$-alkoxycarbonyl)-ethyl compound of general formula I and/or if a compound of general formula I is obtained which contains an $(R_3NR_4)$-$C_{1-3}$-alkyl group wherein $R_3$ and $R_4$ each denote a hydrogen atom, this may subsequently be converted with a corresponding dihaloalkane into a corresponding compound of general formula I wherein $R_3$ and $R_4$ together with the nitrogen atom between them denote a corresponding 4- to 7-membered cycloalkyleneimino group and/or if a compound of general formula I is obtained wherein $R_c$ denotes an amidino group, this may subsequently be converted by reaction with a haloacetic acid derivative and subsequent hydrolysis and decarboxylation into a corresponding amidino compound substituted by one or two methyl groups and/or if a compound of general formula I is obtained wherein $R_c$ denotes a hydroxyamidino group, this may subsequently be converted into a corresponding amidino compound by catalytic hydrogenation and/or if a compound of general formula I is obtained wherein $R_a$ contains a carboxy group, this may subsequently be converted into a corresponding ester by esterification.

The subsequent preparation of a corresponding urea compound of general formula I is expediently carried out with a corresponding isocyanate or carbamoyl chloride, preferably in a solvent such as dimethylformamide and optionally in the presence of a tertiary organic base such as triethylamine at temperatures between 0 and 50° C., preferably at ambient temperature, The subsequent preparation of a corresponding 2-($C_{1-3}$-alkoxy-carbonyl)-ethyl-compound is carried out with a corresponding acrylic acid ester, preferably in a solvent such as methanol, ethanol or isopropanol at temperatures between 50 and 100° C., preferably at the boiling temperature of the reaction mixture.

The subsequent preparation of a corresponding 4- to 7-membered cycloalkyleneimino compound of general formula I is expediently carried out with a corresponding dihaloalkane, preferably in a solvent such as methanol, ethanol or isopropanol in the presence of a base such as sodium carbonate at temperatures between 50 and 100° C., preferably at the boiling temperature of the reaction mixture.

The subsequent alkyLation is expediently carried out in a solvent such as methylene chloride, tetrahydrofuran, dioxane, dimethylsulphoxide, dimethylformamide or acetone optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously act as solvent, or optionally in the presence of silver carbonate or silver oxide at temperatures between −30 and 100° C., but preferably at temperatures between −10 and 80° C.

The subsequent hydrolysis is expediently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane and subsequent decarboxylation in the presence of an acid as hereinbefore described at temperatures between −10 and 120° C., e.g. at temperatures between ambient temperature and the boiling temperature of the reaction mixture.

The subsequent esterification is carried out with a corresponding alcohol, conveniently in a solvent or mixture of solvents such as methylene chloride, benzene, toluene, chlorobenzene, tetrahydrofuran, benzene/tetrahydrofuran or dioxan, but preferably in an excess of the alcohol used, optionally in the presence of an acid such as hydrochloric acid or in the presence of a dehydrating agent, e.g. in the presence of isobutyl chloroformate, thionyl chloride, trimethylchlorosilane, sulphuric acid, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole, triphenylphosphine/carbon tetrachloride or triphenylphosphine/diethyl azodicarboxylate, optionally in the presence of a base such as potassium carbonate, N-ethyldiisopropylamine or N,N-dimethylamino-pyridine expediently at temperatures between 0 and 150° C., preferably at temperatures between 0 and 80° C., or with a corresponding halide in a solvent such as methylene chloride, tetrahydrofuran, dioxane, dimethylsulphoxide, dimethylformamide or acetone, optionally in the presence of a reaction accelerator such as sodium or potassium iodide and preferably in the presence of a base such as sodium carbonate or potassium carbonate or in the presence of a tertiary organic base such as N-ethyl-diisopropylamine or N-methyl-morpholine, which may simultaneously act as solvent, or optionally in the presence of silver carbonate or silver oxide at temperatures between −30 and 100° C., but preferably at temperatures between −10 and 80° C.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, acetyl, benzoyl, tert.butyl, trityl, benzyl or tetrahydropyranyl group, protecting groups for a carboxy group may be a trimethylsilyl, methyl, ethyl, tert.butyl, benzyl or tetrahydropyranyl group and protecting groups for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxan/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidant such as cerium(IV)ammonium nitrate in a solvent such as methylene chloride, acetonitrile or acetonitrile/water at temperatures between 0 and 50° C., but preferably at ambient temperature.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxan or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

An allyloxycarbonyl group is cleaved by treating with a catalytic amount of tetrakis-(triphenylphosphine)-palladium (O), preferably in a solvent such as tetrahydrofuran and preferably in the presence of an excess of a base such as morpholine or 1,3-dimedone at temperatures between 0 and 100° C., preferably at ambient temperature and under an inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

The compounds of general formulae II to XIII used as starting materials, some of which are known from the literature, may be obtained by methods known from the literature and in addition their preparation is described in the Examples.

The chemistry of the compounds of general formula III is described, for example, by Jack Robinson in J. Chem. Soc. 1941, 744, that of the benzimidazoles is described by Katritzky and Rees in Comprehensive Heterocyclic Chemistry, Oxford, Pergamon Press, 1984, and by Schaumann in Hetarene III, Methoden der organischen Chemie (Houben-Weyl), 4$^{th}$ edition, Verlag Thieme, Stuttgart 1993.

Thus, for example, a compound of general formula II is obtained by acylating a corresponding o-diamino compound with a corresponding reactive derivative of a compound of general formula III, a compound of general formulae IV, VII, IX, X, XI and XII is obtained by cyclisation of a corresponding substituted compound according to process a) and if necessary subsequent reduction of any nitro group present in the phenyl moiety, followed by acylation, amidation and/or halogenation.

Moreover, the compounds of general formula I obtained may be resolved into their enantiomers and/or diastereomers, as mentioned hereinbefore.

Thus, for example, the compounds of general formula I obtained which occur as racemates may be separated by methods known per se (cf. Allinger N. L. and Eliel E. L. in "Topics in Stereo-chemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+) or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanol-amine, diethanolamine and triethanolamine.

As already mentioned hereinbefore, the new compounds of general formula I and the salts thereof have valuable properties. Thus, the compounds of general formula I wherein $R_c$ denotes a cyano group are valuable intermediate products for preparing the other compounds of general formula I, and the compounds of general formula I wherein $R_c$ denotes one of the abovementioned amidino groups, and the tautomers, stereoisomers and the physiologically acceptable salts thereof have valuable pharmacological properties, particularly an antithrombotic activity, which is preferably based on an activity which influences thrombin or factor Xa, for example on a thrombin-inhibiting or factor Xa-inhibiting activity, on an activity which extends the aPTT time and on an inhibiting effect on related serine proteases such as, for example, trypsin, urokinase factor VIIa, factor IX, factor XI and factor XII.

For example, the compounds

A=2-(4-amidinophenylaminomethyl)-1-methyl-5-[1-(pyrrolidin-1-yl-carbonyl)cyclopropyl]-benzimidazole-hydrochloride, B=(E/Z)-2-(4-amidiLnophenylaminomethyl)-1-methyl-5-[1-[(pyridin-2-yl)-(carboxymethyloxyimino)methylene]-cyclopropyl]-benzimidazole-hydrochloride, C=2-(4-amidinophenylaminomethyl)-1-methyl-5-[1-(2-carboxyethylamino)-1-(pyrrolidin-1-yl-carbonyl)-ethyl]-benzimidazolehydrochloride, D=2-(4-amidinophe:nylaminomethyl)-1-methyl-5-[1-[2-(2-carboxyethyl)-pyrrolidin-1-yl-carbonyl]cyclopropyl]-benzimidazole-hydrochloride, E=2-(4-amidinophenylaminomethyl)-1-methyl-5-[2-(2-carboxyethyl)-4,5-dimethyl-imidazol-1-yl-methyl]-benzimidazole-hydrochloride, F=2-(4-amidinophenylaminomethyl)-1-methyl-5-[1-(carboxymethylamino)-1-(pyrrolidin-1-yl-carbonyl)-ethyl]-benzimidazol-ehydrochloride and G=2-(4-amidinophenylaminomethyl)-1-methyl-5-[1-(N-methylcarboxymethylcarbonylaminomethyl)-1-methyl-1-(pyrrolidin-1-yl-carbonyl)-ethyl]-benzimidazole-dihydrochloride were investigated for their effect on extending the aPTT time as follows:

Materials:

Plasma, from human citrated blood,

PTT reagent, Boehringer Mannheim (524298), calcium solution (0.025 Mol/l), Behring Werke, Marburg (ORH 056/57),
diethylbarbiturate acetate buffer, Behring Werke, Marburg (ORWH 60/61),
Biomatic B10 coagulometer, Desaga, Wiesloch.
Method:

The aPTT time was determined using a Biomatic B10-coagulometer made by Messrs. Desaga.

The test substance was added to the test vessels prescribed by the manufacturer with 0.1 ml of human citrate plasma and 0.1 ml of PTT reagent. The mixture was incubated for three minutes at 37° C. The clotting reaction was started by the addition of 0.1 ml of calcium solution. Because of the design of the apparatus, the time taken for the mixture to clot was measured as the calcium solution was added. Mixtures to which 0.1 ml of DBA buffer had been added were used as controls.

According to the definition the effective concentration of substance at which the aPTT time was double that of the control was determined by means of a dosage/activity curve.

The following Table contains the values found:

| substance | APTT time ($ED_{200}$ in $\mu M$) |
|---|---|
| A | 0.12 |
| B | 0.42 |
| C | 0.31 |
| D | 0.29 |
| E | 0.29 |
| F | 0.20 |
| G | 0.17 |

The compounds prepared according to the invention are well tolerated, since no toxic side effects could be detected at therapeutic doses.

In view of their pharmacological properties the new compounds and the physiologically acceptable salts thereof are suitable for the prevention and treatment of venous and arterial thrombotic diseases, such as for example the treatment of deep leg vein thrombosis, for preventing reocclusions after bypass operations or angioplasty (PT(C)A), and occlusion in peripheral arterial diseases such as pulmonary embolism, disseminated intravascular coagulation, for preventing coronary thrombosis, stroke and the occlusion of shunts. In addition, the compounds according to the invention are suitable for antithrombotic support in thrombolytic treatment, such as for example with rt-PA or streptokinase, for preventing long-term restenosis after PT(C)A, for preventing metastasis and the growth of clot-dependent tumours and fibrin-dependent inflammatory processes, e.g. in the treatment of pulmonary fibrosis.

The dosage required to achieve such an effect is appropriately 0.1 to 30 mg/kg, preferably 0.3 to 10 mg/kg by intravenous route, and 0.1 to 50 mg/kg, preferably 0.3 to 30 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention:

EXAMPLE 1

2-(4-amidinophenylaminomethyl)-1-methyl-5-[1-(pyrrolidin-1-yl-carbonyl)cyclopropyl]-benzimidazole-hydrochloride a. 1-(4-chloro-3-nitro-phenyl)-1-cyclopropanecarboxylic acid To 350 ml of fuming nitric acid are added, in batches, at −25° C., 50.0 g (0.21 moi) of 1-(4-chlorophenyl)-1-cyclopropanecarboxylic acid. The solution is stirred for 15 minutes at −25° C. and subsequently poured onto ice water. The product precipitated is suction filtered, washed with water and dried.

Yield: 58.5 g (95% of theory), $R_f$ value: 0.45 (silica gel; methylene chloride/methanol=9.5:0.5).

b. 1-(4-methylamino-3-nitro-phenyl)-1-cyclopropanecarboxylic acid 20.0 g (0.083 mol) of 1-(4-chloro-3-nitro-phenyl)-1-cyclopropanecarboxylic acid and 100 ml of methylamine solution (40% in $H_2O$) are heated to 80° C. in a pressure vessel for five hours. The contents are evaporated to dryness, dissolved in water and acidified with glacial acetic acid. The product precipitated is suction filtered, washed with water and dried.

Yield: 16.9 g (93% of theory), $R_f$ value: 0.58 (silica gel; methylene chloride/methanol=9:1).

c. 4-[1-(pyrrolidin-1-yl-carbonyl)cyclopropyl]-2-nitro-N-methylaniline 2.4 g (0.01 mol) of 1-(4-methylamino-3-nitro-phenyl)-1-cyclopropanecarboxylic acid are dissolved in 50 ml dimethylformamide and after the addition of 3.2 g (0.01 mol) of O-(benzotriazol-1-yl)-N,N,N',N'-tetramethyluronium tetrafluoroborate, 0.7 g (0.01 mol) of pyrrolidine and 1.1 g (0.01 mol) of N-methyl-morpholine stirred for 20 hours at ambient temperature. The solvent is distilled off and the residue is chromatographed on silica gel, eluting with methylene chloride. The desired fractions are concentrated by evaporation, triturated with ether, suction filtered and dried.

Yield: 1.8 g (61% of theory), $R_f$ value: 0.51 (silica gel; methylene chloride/methanol=9:1).

d. 4-[1-(pyrrolidin-1-yl-carbonyl)cyclopropyl]-2-amino-N-methylaniline 1.8 g (6.2 mmol) of 4-[1-(pyrrolidin-1-yl-carbonyl)cyclopropyl]-2-nitro-N-methyl-aniline are dissolved in 40 ml methanol and 40 ml methylene chloride and after the addition of 0.4 g of palladium on activated charcoal (10%) hydrogenated for 4 hours at ambient temperature. Then the catalyst is filtered off and the residue is concentrated by evaporation.

Yield: 1.6 g (100% of theory), $R_f$ value: 0.26 (silica gel; methylene chloride/methanol=9:1).

e. 4-[1-(pyrrolidin-1-yl-carbonyl)cyclopropyl]-2-(4-cyanophenyl)aminomethylcarbonylamino-N-methyl-aniline Prepared analogously to Example 1c from 4-[1-(pyrrolidin-1-yl-carbonyl)cyclopropyl]-2-amino-N-methyl-aniline, O-(benzotriazol-1-yl)-N,N,N',N'-tetramethyluronium tetrafluoroborate, 4-cyanophenylglycine and triethylamine in dimethylformamide.

Yield: 66% of theory, $R_f$ value: 0.51 (silica gel; methylene chloride/methanol=9:1).

f. 2-(4-cyanophenylaminomethyl)-1-methyl-5-[1-(pyrrolidin-1-yl-carbonyl)cyclopropyl]-benzimidazole 1.7 g (0.004 mol) of 4-[1-(pyrrolidin-1-yl-carbonyl) cyclopropyl]-2-(4-cyanophenyl)-aminomethylcarbonylamino-N-methyl-aniline are refluxed in 7 ml of glacial acetic acid for 2 hours. The solvent is distilled off, the residue dissolved in water and extracted with methylene chloride. The organic phase is dried, concentrated by evaporation and subsequently chromatographed on silica gel, eluting with methylene chloride +2 to 3% methanol.

Yield: 1.0 g (62% of theory), $R_f$ value: 0.49 (silica gel; methylene chloride/methanol=9:1).

g. 2-(4-amidinophenylaminomethyl)-1-methyl-5-[1-(pyrrolidin-1-yl-carbonyl)cyclopropyl]-benzimidazole-hydrochloride 1.0 g (2.5 mmol) of 2-(4-cyanophenylaminomethyl)-1-methyl-5-[1-(pyrrolidin-1-yl-carbonyl)cyclopropyl]-benzimidazole are dissolved in 50 ml saturated ethanolic hydrochloric acid and stirred for 5 hours at ambient temperature. The solvent is distilled off, the residue dissolved in 50 ml absolute ethanol and mixed with 2.3 g (25 mmol) of ammonium carbonate. After 60 hours at ambient temperature the mixture is evaporated to dryness. The residue is chromatographed on silica gel, eluting with methylene chloride/methanol (7:1).

Yield: 700 mg (62% of theory), $R_f$ value: 0.61 (silica gel; methylene chloride/methanol=4:1) $C_{24}H_{28}N_6O \times HCl$ (416.54/453.0); mass spectrum: $(M+H)^+=417$.

The following compounds are obtained analogously to Example 1:

(1) 2-(4-amidinophenylaminomethyl)-1-methyl-5-[1-(3-methyl-piperidin-1-yl-carbonyl)cyclopropyl]-benzimidazole-hydrochloride.

Yield: 45% of theory, $R_f$ value: 0.25 (silica gel; methylene chloride/methanol=4:1) $C_{26}H_{32}N_6O \times HCl$ (444.9/481.05); mass spectrum: $(M+H)^+=445$.

(2) 2-(4-amidinophenylaminomethyl)-1-methyl-5-[1-(piperidin-1-yl-carbonyl)cyclolpropyl]-benzimidazole-hydrochloride.

Yield: 57% of theory, $R_f$ value: 0.23 (silica gel; methylene chloride/methanol=4:1) $C_{25}H_{30}N_6O \times HCl$ (430.56/467.93); mass spectrum: $(M+H)^+=431$.

(3) 2-(4-amidinophenylaminomethyl)-1-methyl-5-[1-(4-methyl-piperazin-1-yl-carbonyl)cyclopropyl]-benzimidazole-hydrochloride.

Yield: 32% of theory, $R_f$ value: 0.26 (silica gel; methylene chloride/methanol/ammonia=2:1:0.25) $C_{25}H_{31}N_7O \times HCl$ (445.58/482.04); mass spectrum: $(M+H)^+=446$.

(4) 2-(4-amidinophenylaminomethyl)-1-methyl-5-[1-(2,3-dihydroindolin-1-yl-carbonyl)cyclopropyl]-benzimidazole-hydrochloride.

Yield: 60% of theory, $R_f$ value: 0.34 (silica gel; methylene chloride/methanol=4:1) $C_{28}H_{28}N_6O \times HCl$ (464.58/501.04); mass spectrum: $(M+H)^+=465$.

(5) 2-(4-amidinophenylaminomethyl)-1-methyl-5-[1-((2-ethoxycarbonylethyl)-piperidin-1-yl-carbonyl)cyclopropyl]-benzimidazole-hydrochloride.

Yield: 85% of theory, $R_f$ value: 0.57 (silica gel; methylene chloride/methanol=4:1) $C_{30}H_{38}N_6O_3 \times HCl$ (530.67/567.13); mass spectrum: $(M+H)^+=531$.

(6) 2-(4-amidinophenylaminomethyl)-1-methyl-5-[1-((2-ethoxycarbonylethyl)-pyrrolidin-1-yl-carbonyl)cyclopropyl]-benzimidazole-hydrochloride.

Yield: 60% of theory, $C_{29}H_{36}N_6O_3 \times HCl$ (516.64/553.10).

mass spectrum: $(M+H)^+ = 517$ $(M+2H)^{++} = 259$ (7) 2-(4-amidinophenylaminomethyl)-1-methyl-5-[1-[(N-(2-ethoxycarbonylethyl)-N-methyl-aminomethyl)-pyrrolidin-1-yl-carbonyl]cyclopropyl]-benzimidazole-hydrochloride.

Yield: 65% of theory, $C_{31}H_{41}N_7O_3 \times HCl$ (559.72/596.18).

mass spectrum: $(M+H)^+ = 560$ $(M+2H)^{++} = 280.6$ (8) 2-(4-amidinophenylaminomethyl)-1-methyl-5-[1-[(2-ethoxycarbonylmethyloxymethyl)-pyrrolidin-1-yl-carbonyl]cyclopropyl]-benzimidazole-hydrochloride Yield: 61% of theory, $R_f$ value: 0.20 (silica gel; methylene chloride/ethanol=8:2+1% glacial acetic acid); $C_{29}H_{36}N_6O_4 \times HCl$ (532.66/569.11).

mass spectrum: $(M+H)^+ = 533$ $(M+2H)^{++} = 267$

EXAMPLE 2

2-(4-amidinophenylaminomethyl)-1-methyl-5-(1-cyclopentylcarbonyl-3-chloro-n-propyl)-benzimidazole-hydrochloride a. 4-[1-(cyclopentylcarbonyl)cyclopropyl]-chlorobenzene 2.4 g (0.1 mol) of magnesium chips are suspended in 10 ml ether. After the addition of a spatula-tip of iodine, 14.9 g (0.1 mol) of bromocyclopentane are slowly added dropwise to 40 ml of ether, the reaction being started off initially by gentle heating. After the addition has ended the mixture is refluxed for 30 minutes. Then a solution of 14.0 g (0.08 mol) of 1-(4-chlorophenyl)-1-cyclopropanecarbonitrile in 75 ml ether is added and refluxed for a further 3 hours. The reaction solution is poured onto ice water, adjusted to pH 3 with hydrochloric acid and extracted with ether. The organic extracts are dried and concentrated by evaporation. The residue is chromatographed on silica gel and eluted with petroleum ether/ethyl acetate (19:1 and 15:1).

Yield: 3.0 g (12% of theory), $R_f$ value: 0.58 (silica gel; petroleum ether/ethyl acetate=4:1).

b. 4-[1-(cyclopentylcarbonyl)cyclopropy]-2-nitro-chlorobenzene

Prepared analogously to Example 1a from 4-[1-(cyclopentylcarbonyl)cyclopropyl]-chlorobenzene and fuming nitric acid.

Yield: 87% of theory, $R_f$ value: 0.60 (silica gel; petroleum ether/ethyl acetate=9:1).

c. 4-[1-(cyclopentylcarbonyl)cyclopropyl]-2-nitro-N-methylaniline

Prepared analogously to Example 1b from 4-[1-(cyclopentylcarbonyl)cyclopropyl]-2-nitro-chlorobenzene and aqueous methylamine solution.

Yield: 18% of theory, $R_f$ value: 0.54 (silica gel; methylene chloride/ethanol=19:1).

d. 4-[1-(cyclopentylcarbonyl)cyclopropyl]-2-amino-N-methylaniline 2.3 g (7.9 mmol) of 4-[1-(cyclopentylcarbonyl)-cyclopropyl]-2-nitro-N-methyl-aniline are dissolved in 125 ml ethyl acetate and 25 ml ethanol and after the addition of 1.0 g Raney nickel hydrogenated for 1.5 hours at ambient temperature. Then the catalyst is filtered off and the residue is concentrated by evaporation.

Yield: 2.0 g (98% of theory), $R_f$ value: 0.15 (silica gel; methylene chloride/ethanol=19:1).

e. 4-[1-(cyclopentylcarbonyl)cyclopropyl]-2-(4-cyanophenylaminomethylcarbonylamino)-N-methyl-aniline Prepared analogously to Example 1c from 4-[1-(cyclopentylcarbonyl)cyclopropyl]-2-amino-N-methylaniline, O-(benzotriazol-1-yl)-N,N,N',N'-tetramethyluroniumtetrafluoroborate, 4-cyanophenylglycine and triethylamine in dimethylformamide.

Yield: 96% of theory, $R_f$ value: 0.54 (silica gel; methylene chloride/ethanol=19:1).

f. 2-(4-cyanophenylaminomethyl)-1-methyl-5-[1-(cyclopentylcarbonyl)-cyclopropyl]-benzimidazole Prepared analogously to Example 1f from 4-[1-(cyclopentylcarbonyl)cyclopropyl]-2-(4-cyanophenyl-aminomethylcarbonylamino)-N-methyl-aniline in glacial acetic acid.

Yield: 53% of theory, $R_f$ value: 0.46 (silica gel; methylene chloride/ethanol=19:1).

g. 2-(4-amidinophenylaminomethyl)-1-methyl-5-(1-cyclopentyl-carbonyl-3-chloro-n-propyl)-benzimidazole hydrochloride Prepared analogously to Example 1g from 2-(4-cyanophenylaminomethyl)-1-methyl-5-(1-cyclopentyl-carbonyl-3-chloro-n-propyl)-benzimidazole and hydrochloric acid/ammonium carbonate in ethanol.

Yield: 61% of theory, $C_{25}H_{30}ClN_5O \times HCl$ (452.00/488.56); mass spectrum: $(M+H)^+=452/4$ (Cl)).

EXAMPLE 3

(E/Z)-2-(4-amidinophenylaminomethyl)-1-methyl-5-[1-[(pyridin-3-yl)-(ethoxycarbonylmethyloxyimino)-methylene]cyclopropyl]-benzimidazole-hydrochloride a. 1-[(pyridin-3-yl)-carbonyl]cycloproyl-benzene A solution of 21.4 g (0.135 mol) of 3-bromopyridine in 125 ml of ether is added dropwise at −40 to −50° C. to 100 ml of butyllithium (1.6 M in hexane) and then stirred for 20 minutes at −40° C. The mixture is then cooled to −60° C. and a solution of 20.1 g (0.14 mol) of 1-phenyl-cyclopropane-carbonitrile in 125 ml ether is added dropwise. After it has all been added, the reaction mixture is heated to ambient temperature and stirred for 5 hours. The suspension is mixed with 20% hydrochloric acid and heated to 100° C. for 30 minutes. After cooling, the mixture is adjusted to pH 8 with 20% sodium hydroxide solution and extracted with ethyl acetate. The combined organic extracts are dried and concentrated by evaporation. The residue is chromatographed on aluminium oxide, eluting with petroleum ether/ethyl acetate (9:1).

Yield: 14.0 g (46% of theory), $R_f$ value: 0.27 (aluminium oxide; petroleum ether/ethyl acetate=9:1).

b. 4-[1-[(pyridin-3-yl)-carbonyl]cyclopropyl]-nitrobenzene

Prepared analogously to Example 1a from 1-[(pyridin-3-yl)-carbonyl]cyclopropyl-benzene and fuming nitric acid.

Yield: 53.7% of theory, $R_f$ value: 0.29 (aluminium oxide; petroleum ether/ethyl acetate=4:1).

c. 4-[1-[(Pyridin-3-yl)-carbonyl]cyclopropyl]-aniline

Prepared analogously to Example 2d from 4-[1-[(pyridin-3-yl)-carbonyl]cyclopropyl]-nitrobenzene and Raney nickel in ethyl acetate/ethanol.

Yield: 94% of theory, $R_f$ value: 0.51 (silica gel; methylene chloride/ethanol=19:1).

d. 4-[1-[(pyridin-3-yl)-carbonyl]cyclopropyl]-trifluoro-acetylaniline 8.0 g (33.5 mmol) of 4-[1-[(pyridin-3-yl)-carbonyl]cyclopropyl]-aniline are dissolved in 100 ml chlorobenzene and after the addition of 15 ml trifluoroacetic anhydride the mixture is stirred for two hours at 110° C. The solvent is distilled off, the residue stirred with petroleum ether/ether (9:1), suction filtered and dried.

Yield: 10.0 g (88% of theory), $R_f$ value: 0.54 (silica gel; methylene chloride/ethanol=19:1).

e. 4-[1-[(pyridin-3-yl)-carbonyl]cyclopropyl]-2-nitro-trifluoroacetylaniline 1.7 g (5 mmol) of 4-[1-[(pyridin-3-yl)-carbonyl]cyclopropyl]-trifluoroacetylaniline are added batchwise to 13 ml of conc. sulphuric acid and 16 ml of 65% nitric acid at −5° C. Then the mixture is stirred for a further 30 minutes without cooling, poured onto ice water and extracted with ethyl acetate. The organic extracts are dried and concentrated by evaporation. The residue is chromatographed on silica gel and eluted with methylene chloride/ethanol (50:1 and 25:1). The desired fractions are concentrated by evaporation, triturated with ether/petroleum ether, suction filtered and dried.

Yield: 1.2 g (75% of theory), $R_f$ value: 0.70 (silica gel; methylene chloride/ethanol=19:1).

f. 4-[1-[(pyridin-3-yl)-carbonyl]cyclopropyl]-2-nitro-N-trifluoroacetyl-N-methyl-aniline 1.15 g (3.0 mmol) of 4-[1-[(pyridin-3-yl)-carbonyl]cyclopropyl]-2-nitro-trifluoroacetylaniline are dissolved in 50 ml acetone and after the addition of 2.0 g potassium carbonate and 0.8 ml methyl iodide refluxed for two hours. The insoluble matter is filtered off and the solution is evaporated down. The residue is chromatographed on silica gel, eluting with petroleum ether/ethyl acetate (1:1 and 1:4).

Yield: 0.88 g (75% of theory), $R_f$ value: 0.38 (silica gel; petroleum ether/ethyl acetate=1:1).

g. 4-[1-[(pyridin-3-yl)-carbonyl]cyclopropyl]-2-nitro-N-methyl-aniline 7.4 g (18.8 mmol) of 4-[1-[(pyridin-3-yl)-carbonyl]cyclopropyl]-2-nitro-N-trifluoroacetyl-N-methyl-aniline are stirred in 200 ml of 20% potassium hydroxide solution for one hour at 30° C. Then the mixture is diluted with isopropanol, the organic phase is separated off, 10.0 g of aluminium oxide are added and the resulting mixture is evaporated to dryness. The residue is chromatographed on aluminium oxide, eluting with petroleum ether/ethyl acetate (4:1 and 1:1).

Yield: 2.6 g (47% of theory), $R_f$ value: 0.50 (silica gel; petroleum ether/ethyl acetate=1:1).

h. 4-[1-[(pyridin-3-yl)-carbonyl]cyclopropyl]-2-amino-N-methyl-aniline

Prepared analogously to Example 2d from 4-[1-[(pyridin-3-yl)-carbonyl]cyclopropyl]-2-nitro-N-methyl-aniline and Raney nickel in ethyl acetate/ethanol.

Yield: 98% of theory, $R_f$ value: 0.51 (silica gel; methylene chloride/ethanol=19:1).

i. 4-[1-[(pyridin-3-yl)-carbonyl]cyclopropyl]-2-(4-cyanophenyl)-aminomethylcarbonylamino-N-methyl-aniline Prepared analogously to Example 1c from 4-[1-[(pyridin-3-yl)-carbonyl]cyclopropyl]-2-amino-N-methyl-aniline, O-(benzotriazol-1-yl)-N,N,N',N'-tetramethyluronium tetrafluoroborate, 4-cyanophenylglycine and triethylamine in dimethylformamide.

Yield: 97% of theory, $R_f$ value: 0.48 (silica gel; methylene chloride/ethanol=19:1).

k. 2-(4-cyanophenylaminomethyl)-1-methyl-5-[1-[(pyridin-3-yl)-carbonyl]cyclopropyl]-benzimidazole Prepared analogously to Example 1f from 4-(pyridin-3-yl-carbonyl)cyclopropyl-2-(4-cyanophenyl)-aminomethylcarbonylamino-N-methyl-aniline in glacial acetic acid.

Yield: 76% of theory, $R_f$ value: 0.52 (silica gel; methylene chloride/ethanol=19:1).

l. (E/Z)-2-(4-cyanophenylaminomethyl)-1-methyl-5-[1-[(pyridin-3-yl)-(carboxymethyloxyimino)methylene]-cyclopropyl]benzimidazole 1.6 g (4.0 mmol) of 2-(4-cyanophenylaminomethyl)-1-methyl-5-[1-[(pyridin-3-yl)-carbonyl]cyclopropyl]-benzimidazole, 3.0 g (12 mmol) of carboxy-methoxylamine-hemihydrate, 0.84 ml of triethylamine, 12 g of molecular sieve 3A and 12 g of molecular sieve 4A are refluxed for 12 hours in 80 ml methanol and 40 ml toluene. Then the molecular sieve is filtered off and the filtrate is concentrated by evaporation. The residue is stirred with water, suction filtered and dried. The crude product is chromatographed on silica gel, eluting with methylene chloride/ethanol/glaciaL acetic acid (25:1:0 and 8:2:0.2).

Yield: 0.9 g (48% of theory), $R_f$ value: 0.34 (silica gel; methylene chloride/ethanol/glacial acetic acid=8:2:0.2).

m. (E/Z)-2-(4-amidinophenylaminomethyl)-1-methyl-5-[1-[(pyridin-3-yl)-(ethoxycarbonylmethyloxyimino)-methylene]cyclopropyl]-benzimidazole-hydrochloride Prepared analogously to Example 1g from (E/Z)-2-(4-cyanophenyl-aminomethyl)-1-methyl-5-[1-[(pyridin-3-yl)-(ethoxycarbonyl-methyloxyimino)methylene]cyclopropyl]-benzimidazole and hydrochloric acid/ammonium carbonate in ethanol.

Yield: 60% of theory, $R_f$ value: 0.28 (silica gel; methylene chloride/ethanol/glacial acetic acid=8:2:0.2); $C_{29}H_{31}N_7O_3 \times$ HCl (525.62/562.09); mass spectrum: $(M+H)^+=526$.

The following compounds are obtained analogously to Example 3:

(1) (E/Z)-2-(4-amidinophenylaminomethyl)-1-methyl-5-[1-[(pyridine-2-yl)-(ethoxycarbonylmethyloxyimino)-methylene]cyclopropyl]-benzimidazole-hydrochloride Yield: 52% of theory, $R_f$ value: 0.21 (silica gel; methylene chloride/ethanol/glacial acetic acid=8:2:0.2) $C_{29}H_{31}N_7O_3 \times$ HCl (525.62/562.09); mass spectrum: $(M+H)^+=526$.

(2) (E/Z)-2-(4-amidinophenylaminomethyl)-1-methyl-5-[1-[phenyl-(ethoxycarbonylmethyloxyimino)-methylene]-cyclopropyl]-benzimidazole-hydrochloride Yield: 18% of theory, $C_{30}H_{32}N_6O_3 \times$ HCl (524.63/561.09).

mass spectrum: $(M+H)^+ = 525$ $(M-H+HCl)^- = 559/61$ (Cl)

(3) 2-(4-amidinophenylaminomethyl)-1-methyl-5-[1-(1-methyl-pyrazol-5-yl-carbonyl)cyclopropyl]-benzimidazole-hydrochloride Yield: 10% of theory, $C_{24}H_{25}N_7O \times$ HCl (427.51/463.97).

mass spectrum: $(M+H)^+ = 428$ $(M+H+HCl)^- = 464/6$ (Cl)

(4) (E/Z)-2-(4-amidinophenylaminomethyl)-1-methyl-5-[1-[(1-methyl-pyrazol-5-yl)-(ethoxycarbonylmethyloxyimino)-methylene]cyclopropyl]-benzimidazole-hydrochloride Yield: 80% of theory, $R_f$ value: 0.20 (silica gel; methylene chloride/ethanol=8:2+1% glacial acetic acid) $C_{28}H_{32}N_8O_3 \times$ HCl (528.63/565.08); mass spectrum: $(M+H)^+=529$.

(5) (E/Z)-2-(4-amidinophenylaminomethyl)-1-methyl-5-[1-[phenyl-(3-ethoxycarbonyl-n-propyloxyimino) methylene]-cyclopropyl]-benzimidazole-dihydrochloride Yield: 47% of theory, $R_f$ value: 0.06 (silica gel; methylene chloride/methanol=9:1) $C_{32}H_{36}N_6O_3 \times 2$ HCl (552.69/625.60); mass spectrum: $(M+H)^+ =553$.

EXAMPLE 4

(E/Z)-2-(4-amidinophenylaminomethyl)-1-methyl-5-[1-[(pyridine-2-yl)-(carboxymethyloxyimino) methylene]-cyclopropyl]-benzimi-dazole-hydrochloride 150 mg (E/Z)-2-(4-amidinophenylaminomethyl)-1-methyl-5-[1-[(pyridin-2-yl-(ethoxycarbonylmethyloxyimino)-methylene]cyclopropyl]-benzimidazole-hydrochloride and 2.5 ml of 2N sodium hydroxide solution are stirred in 10 ml ethanol for 5 hours at ambient temperature. The alcohol is distilled off and the residue is adjusted to pH 5 with hydrochloric acid. The crystalline product is suction filtered, washed with water and dried.

Yield: 46% of theory, $R_f$ value: 0.10 (silica gel; methylene chloride/ethanol/-glacial acetic acid=8:2:0.1) $C_{27}H_{27}N_7O_3 \times$ HCl (497.58/534.05)

mass spectrum: $(M+H)^+ = 498$ $(M+Na)^+ = 520$

The following compounds are obtained analogously to Example 4:

(1) 2-(4-amidinophenylaminomethyl)-1-methyl-5-[1-[2-(2-carboxyethyl)-piperidin-1-yl-carbonyl]cyclopropyl]-benzimidazole-hydrochloride Yield: 94% of theory, $R_f$ value: 0.57 (Reversed phase RP 18; methanol/5% sodium chloride solution=3:2) $C_{28}H_{34}N_6O_3 \times$ HCl (502.62/539.08).

mass spectrum: $(M+H)^+ = 503$ $(M+Na)^+ = 525$ (2) 2-(4-amidinophenylaminomethyl)-1-methyl-5-[1-(2-carboxyethylamino)-1-(pyrrolidin-1-yl-carbonyl)-ethyl]-benzimidazole-hydrochloride Yield: 98% of theory, $R_f$ value: 0.73 (Reversed phase RP 8; methanol/5% sodium chloride solution=1:2); $C_{26}H_{33}N_7O_3 \times$ HCl (491.60/564.54).

mass spectrum: $(M+H)^+ = 492$ $(M+2H)^{++} = 247$ (3) 2-(4-amidinophenylaminomethyl)-1-methyl-5- [1-(3-carboxypropionylamino)-1-(ethoxycarbonyl)-ethyl]-benzimidazole-hydrochloride Yield: 98% of theory, $R_f$ value: 0.70 (RP 8; methanol/5% sodium chloride solution=1:2); $C_{25}H_{30}N_6O_5 \times$ HCl (494.55/531.05).

mass spectrum: $(M+H)^+ = 495$ $(2M+H)^+ = 989$ (4) 2-(4-amidinophenylaminomethyl)-1-methyl-5-[1-(carboxymethylamino)-1-(pyrrolidin-1-yl-carbonyl)-methyl]-benzimidazole-hydrochloride Yield: 87% of theory, $C_{24}H_{29}N_7O_3 \times$ HCl (463.54/500.04).

mass spectrum: $(M+H)^+ = 464$ $(M+2H)^+ = 232.6$ (5) 2-(4-amidinophenylaminomethyl)-1-methyl-5-[1-[2-(2-carboxyethyl)-pyrrolidin-1-yl-carbonyl]cyclopropyl]-benzimidazole-hydrochloride Yield: 94% of theory, $C_{27}H_{32}N_6O_3 \times HCl$ (488.59/525.05).

mass spectrum: $(M+H)^+ = 489$
$(M+Na)^+ = 511$ (6) 2-(4-amidinophenylaminomethyl)-1-methyl-5-[1-(carboxymethylcarbonylamino)-1-(pyrrolidin-1-yl-carbonyl)-methyl]-benzimidazole-hydrochloride Yield: 49% of theory, $C_{25}H_{29}N_7O_4 \times HCl$ (491.55/528.01).

mass spectrum: $(M+H)^+ = 492$
$(M+H+Na)^{++} = 257.7$ (7) 2-(4-amidinophenylaminomethyl)-1-methyl-5-[1-(carboxymethylcarbonylamino)-1-(pyrrolidin-1-yl-carbonyl)-ethyl]-benzimidazole-hydrochloride Yield: 92% of theory, $C_{26}H_{31}N_7O_4 \times HCl$ (505.58/542.04).

mass spectrum: $(M+H)^+ = 506$
$(M+H+Na)^{++} = 264.7$ (8) 2-(4-amidinophenylaminomethyl)-1-methyl-5-(5-methyl-3-carboxymethyl-imidazolin-2,4-dion-5-yl)-benzimidazole-hydrochloride Yield: 88% of theory, $C_{22}H_{23}N_7O_4 \times HCl$ (449.47/485.94).

mass spectrum: $(M+H)^+ = 450$
$(M+2Na)^{++} = 247.7$ (9) (E/Z)-2-(4-amidinophenylaminomethyl)-1-methyl-5-[1-[(pyridin-3-yl)-(carboxymethyloxyimino)methylene]-cyclopropyl]-benzimidazole-hydrochloride Yield: 54% of theory, $C_{27}H_{27}N_7O_3 \times HCl$ (497.56/534.09).

mass spectrum: $(M+H)^+ = 498$
$(M+Na)^+ = 520$

(10) 2-(4-amidinophenylaminomethyl)-1-methyl-5-[1-[2-(N-(2-carboxyethyl)-N-methyl-aminomethyl)-pyrrolidin-1-yl-carbonyl]-cyclopropyl]-benzimidazole-hydrochloride Yield: 100% of theory, $C_{29}H_{37}N_7O_3 \times HCl$ (531.66/568.12).

mass spectrum: $(M+H)^+ = 532$
$(M-H)^- = 530$

(11) 2-(4-amidinophenylaminomethyl)-1-methyl-5-[N-(2-carboxyethyl)-N-(2-pyridyl)-aminomethyl]-benzimidazole-hydrochloride Yield: 91% of theory, $C_{25}H_{27}N_7O_2 \times HCl$ (457.54/493.96); mass spectrum: $(M+H)^+=458$.

(12) 2-(4-amidinophenylaminomethyl)-1-methyl-5-(N-benzenesulphonyl-N-carboxymethyl-aminomethyl)-benzimidazole-hydrochloride Yield: 84% of theory, $C_{25}H_{26}N_6O_4S \times HCl$ (506.59/543.06); mass spectrum: $(M+H)^+=507$.

(13) 2-(4-amidinophenylaminomethyl)-1-methyl-5-[2-(2-carboxyethyl)-benzimidazole-1-yl-methyl]-benzimidazole-hydrochloride Yield: 76% of theory, $C_{27}H_{27}N_7O_2 \times HCl$ (481.56/518.05).

mass spectrum: $(M+H)^+ = 482$
$(M+2H)^{2+} = 242$
$(M+Na)^+ = 504$
$(M+H+Na)^{2+} = 253$
$(M-H+2Na)^+ = 526$
$(M+2Na)^{2+} = 264$

(14) 2-(4-amidinophenylaminomethyl)-1-methyl-5-(2-methyl-4-carboxy-imidazol-1-yl-methyl)-benzimidazole-hydrochloride Yield: 61% of theory, $C_{22}H_{23}N_7O_2 \times HCl$ (417.47/453.92); mass spectrum: $(M+H)^+=418$.

(15) 2-(4-amidinophenylaminomethyl)-1-methyl-5-[3-(3-carboxy-n-propyl)-benzimidazol-2-on-1-yl-methyl]-benzimidazole-hydrochloride Yield: 86% of theory, $C_{28}H_{29}N_7O_3 \times HCl$ (511.59/548.04).

mass spectrum: $(M+H)^+ = 512$
$(M+Na)^+ = 534$
$(M+H+Na)^+ = 267.7$
$(M+2Na)^{2+} = 278.8$

(16) 2-(4-amidinophenylaminomethyl)-1-methyl-5-[3-(2-carboxyethyl)-imidazo[4,5-b]pyridin-2-on-1-yl-methyl]-benzimidazole-hydrochloride Yield: 83% of theory, $C_{26}H_{26}N_8O_3 \times HCl$ (498.55/535).

mass spectrum: $(M+H)^+ = 499$
$(M+Na)^+ = 521$
$(M-H)^- = 497$
$(2M-H)^- = 995$

(17) 2-(4-amidinophenylaminomethyl)-1-methyl-5-[2-(2-carboxyethyl)-4,5-dimethyl-imidazol-1-yl-methyl]-benzimidazole-hydrochloride Yield: 68% of theory, $R_f$ value: 0.70 (Reversed phase RP 8; methanol/5% sodium chloride solution=6:4); $C_{25}H_{29}N_7O_2 \times HCl$ (459.56/496.01).

mass spectrum: $(M+H)^+ = 460$
$(M+Na)^+ = 482$
$(M+H+Na)^{2+} = 241$

(18) (E/Z)-2-(4-amidinophenylaminomethyl)-1-methyl-5-[1-[phenyl-(carboxymethyloxyimino)methylene]cyclopropyl]-benzimidazole-dihydrochloride Yield: 70% of theory, $C_{28}H_{28}N_6O_3 \times 2HCl$ (496.57/569.5).

mass spectrum: $(M+H)^+ = 497$
$(M-H)^- = 495$

(19) (E/Z)-2-(4-amidinophenylaminomethyl)-1-methyl-5-[1-[(pyridin-3-yl)-(carboxymethylidene)-methylene]cyclopropyl]-benzimidazole-hydrochloride Yield: 37% of theory $R_f$ value: 0.45 (Reversed phase RP 8; methanol/5% sodium chloride solution=6:4) $C_{27}H_{26}N_6O_2 \times HCl$ (466.55/503.0); mass spectrum: $(M+H)^+ = 467$.

(20) (E/Z)-2-(4-amidinophenylaminomethyl)-1-methyl-5-[1-[(1-methyl-pyrazol-5-yl)-(carboxymethyloxyimino)-methylene]cyclopropyl]-benzimidazole-hydrochloride Yield: 30% of theory, $R_f$ value: 0.25 (Reversed phase RP 8; (5% saline solution/methanol=1:1) $C_{26}H_{28}N_8O_3 \times HCl$ (500.58/537.03).

mass spectrum: $(M+H)^+ = 501$
$(M-H)^- = 499$
$(M+Cl)^+ = 535/537$ (Cl)

(21) (E/Z)-2-(4-amidinophenylaminomethyl)-1-methyl-5-[1-[phenyl-(3-carboxy-n-propyloxyimino)methylene]-cyclopropyl]-benzimidazole-dihydrochloride Yield: 37% of theory, $R_f$ value: 0.35 (Reversed phase RP 8; 5% saline solution/methanol=3:2) $C_{30}H_{32}N_6O_3 \times 2HCl$ (524.64/597.55); mass spectrum: $(M+H)^+ = 525$.

EXAMPLE 5

2-(4-amidinophenylaminomethyl)-1-methyl-5-[1-(pyrrolidin-1-yl-carbonyl)-aminomethyl]-benzimidazole-hydrochloride a. 5-(4-chlorophenyl)-imidazolidin-2,4-dione 15.0 g (0.11 mol) of 4-chlorobenzaldehyde, 51.3 g (0.53 mol) of ammonium carbonate and 7.6 g (0.12 mol) of potassium cyanate are stirred in 150 ml water and 150 ml methanol for 18 hours at 55° C. The solvent is distilled off, the residue dissolved in water and extracted with ethyl acetate. The combined organic extracts are dried and concentrated by evaporation.

Yield: 8.6 g (38% of theory), melting point: 215° C.

b. 5-(4-chloro-3-nitro-phenyl)-imidazolidin-2,4-dione

Prepared analogously to Example 1a from 5-(4-chlorophenyl)-imidazolidin-2,4-dione and fuming nitric acid.

Yield: 52% of theory, $R_f$ value: 0.63 (silica gel; methylene chloride/methanol=9:1).

c. 4-chloro-3-nitro-phenylalanine-hydrochloride 560 mg (2.2 mmol) of 5-(4-chloro-3-nitro-phenyl)-imidazolidin-2,4-dione are refluxed for 24 hours in 20 ml of semiconc. hydrochloric acid. The solvent is distilled off, the residue dissolved in water, filtered to remove the insoluble matter and concentrated by evaporation. The residue is dissolved three times in ethanol, evaporated to dryness, triturated with ether, suction filtered and dried.

Yield: 380 mg (65% of theory), melting point: 186° C.

d. 4-chloro-3-nitro-N-tert.butyloxycarbonyl-phenylalanine 5.7 g (17.8 mmol) of 4-chloro-3-nitro-phenylalanine-hydrochloride are dissolved in 50 ml dioxane and 25 ml water and, after the addition of 5.5 ml (39.1 mmol) of triethylamine and 4.8 g (21.3 mmol) of di-tert.butyl-dicarbonate, stirred for 18 hours at ambient temperature. Then the mixture is diluted with 0.5 M potassium hydrogen sulphate solution and extracted with ethyl acetate. The combined organic extracts are dried and concentrated by evaporation. Yield: 6.3 g (100% of theory), $R_f$ value: 0.20 (silica gel; methylene chloride/methanol=9:1).

e. 2-(4-chloro-3-nilro-phenyl)-2-tert.butyloxycarbonylamino-1-(pyrrolidin-1-yl)-ethanone Prepared analogously to Example 1c from 4-chloro-3-nitro-N-tert.butyloxycarbonyl-phenylalanine, O-(benzotriazol-1-yl)-N,N,N',N'-tetramethyluronium tetrafluoroborate, pyrrolidine and N-ethyl-diisopropylamine in tetrahydrofuran.

Yield: 68 of theory, melting point: 203° C.

f. 2-(4-methylamino-3-nitro-phenyl)-2-tert.butyloxycarbonyl-amino-1-(pyrrolidin-1-yl)-ethanone Prepared analogously to Example 1b from 2-(4-chloro-3-nitro-phenyl)-2-tert.butyloxycarbonylamino-1-(pyrrolidin-1-yl)-ethanone and methylamine solution.

Yield: 76% of theory, $R_f$ value: 0.33 (silica gel; cyclohexane/ethyl acetate=1:1).

g. 2-(4-methylamino-3-amino-phenyl)-2-tert.butyloxycarbonylamino-1-pyrrolidin-1-yl-ethanone Prepared analogously to Example 1d from 2-(4-methylamino-3-nitro-phenyl)-2-tert.butyloxycarbonylamino-1-(pyrrolidin-1-yl)-ethanone and palladium on activated charcoal in methylene chloride/ethanol.

Yield: 100% of theory, $R_f$ value: 0.12 (silica gel; cyclohexane/ethyl acetate=1:1).

h. 2-[4-methylamino-3-(4-cyanophenylamino-methylcarbonylamino)-phenyl]-2-tert.butyloxycarbonylamino-1-(pyrrolidin-1-yl)-ethanone Prepared analogously to Example 1c from 2-(4-methylamino-3-aminophenyl)-2-tert.butyloxycarbonylamino-1-(pyrrolidin-1-yl)-ethanone, O-(benzotriazol-1-yl)-N,N,N',N'-tetramethyluronium tetrafluoroborate, 4-cyano-phenylglycine and triethylamine in tetrahydrofuran.

Yield: 100% of theory, $R_f$ value: 0.50 (silica gel; methylene chloride/methanol=9:1).

i. 2-(4-cyanophenylaminomethyl)-1-methyl-5-[1-(pyrrolidin-1-yl-carbonyl)-aminomethyl]-benzimidazole Prepared analogously to Example 1f from 2-[4-methylamino-3-(4-cyanophenylaminomethyl-carbonylamino)-phenyl]-2-tert.butyloxycarbonylamino-1-(pyrrolidin-1-yl)-ethanone in glacial acetic acid.

Yield: 30% of theory, $R_f$ value: 0.19 (silica gel; methylene chloride/methanol=9.5:0.5).

k. 2-(4-amidinophenylaminomethyl)-1-methyl-5-[1-(pyrrolidin-1-yl-carbonyl)-aminomethyl]-benzimidazole-hydrochloride Prepared analogously to Example 1g from 2-(4-cyanophenylaminomethyl)-1-methyl-5-[1-(pyrrolidin-1-yl-carbonyl)-aminomethyl]-benzimidazole and hydrochloric acid/ammonium carbonate in ethanol.

Yield: 27% of theory, $C_{22}H_{27}N_7O \times HCl$ (405.50/441.96); mass spectrum: $(M+H)^+ = 406$.

The following compounds are obtained analogously to Example 5:

(1) 2-(4-amidinophenylaminomethyl)-1-methyl-5-[1-(pyrrolidin-1-yl-carbonyl)-N-acetyl-aminomethyl]-benzimidazole-hydrochloride Yield: 29% of theory, $C_{24}H_{29}N_7O_2 \times HCl$ (447.54/484.54); mass spectrum: $(M+H)^+ = 448$.

(2) 2-(4-amidinophenylaminomethyl)-1-methyl-5-[1-(pyrrolidin-1-yl-carbonyl)-N-(2-ethoxycarbonylethyl)-N-methyl-aminomethyl]-benzimidazole-hydrochloride Yield: 74% of theory, $C_{28}H_{37}N_7O_3 \times HCl$ (519.65/556.11); mass spectrum: $(M+H)^+=520$.

(3) 2-(4-amidinophenylaminomethyl)-1-methyl-5-[1-(pyrrolidin-1-yl-carbonyl)-N-(elthoxycarbonylmethyl)-aminomethyl]-benzimida-zole-hydrochloride Yield: 76% of theory, $C_{26}H_{33}N_7O_3 \times HCl$ (491.59/528.05).

mass spectrum: $(M + H)^+ = 492$
$(M + 2H)^{++} = 246.7$ (4) 2-(4-amidinophenylaminomethyl)-1-methyl-5-[1-(pyrrolidin-1-yl-carbonyl)-N,N-di-(ethoxycarbonylmethyl)-aminomethyl]-benzimidazole-hydrochloride Yield: 51% of theory, $C_{30}H_{39}N_7O_5 \times HCl$ (577.68/614.14).

mass spectrum: $(M + H)^+ = 578$
$(M + Na)^+ = 600$ (5) 2-(4-amidinophenylaminomethyl)-1-methyl-5-[1-(pyrrolidin-1-yl-carbonyl)-N-(ethoxycarbonylmethyl-carbonyl)-aminomethyl]-benzimidazole-hydrochloride Yield: 29% of theory, $C_{27}H_{33}N_7O_4 \times HCl$ (519.60/556.06).

mass spectrum: $(M + H)^+ = 520$
$(M + 2H)^{++} = 260.7$ (6) 2-(4-amidinophenylaminomethyl)-1-methyl-5-[1-(pyrrolidin-1-yl-carbonyl)-N-(2-ethoxycarbonylethyl)-aminomethyl]-benzimidazole-hydrochloride Yield: 84% of theory, $C_{27}H_{35}N_7O_3 \times HCl$ (505.62/542.62).

mass spectrum: $(M + H)^+ = 506$
$(M + 2H)^{++} = 253.7$

EXAMPLE 6

2-(4-amidinophenylaminomethyl)-1-methyl-5-[1-[N-(2-ethoxycarbonylethyl)-amino]-1-(pyrrolidin-1-yl-carbonyl)-ethyl]-benzimidazole-hydrochloride a. 5-(4-chloro-3-nitro-phenyl)-5-methyl-imidazolidin-2,4-dione To 50 ml of fuming nitric acid are added batchwise at −25° C. to −35° C. 10.0 g (4.45 mmol) of 5-(4-chloro-phenyl)-5-methyl-imidazolidin-2,4-dione. After 45 minutes at °25 to °20° C. the reaction mixture is poured onto ice water. The crystalline product is suction filtered, washed with water and dried.

Yield: 10.5 g (100% of theory), melting point: 173–178° C. $R_f$ value: 0.30 (silica gel; cyclohexane/ethyl acetate=1:1).

b. 2-amino-2-(4-chloro-3-nitro-phenyl)-propionic acid 10.5 g (0.044 mol) of 5-(4-chloro-3-nitro-phenyl)-5-methylimidazolidine-2,4-dione are refluxed in 200 ml dioxane and 700 ml of 6N hydrochloric acid for 5 days. The solution is concentrated by evaporation, the residue is taken up in water and extracted with ethyl acetate. The aqueous phase is concentrated by evaporation, mixed with toluene and evaporated to dryness. The residue is triturated with ether, suction filtered and dried.

Yield: 6.8 g (63% of theory), $R_f$ value: 0.24 (Reversed phase RP8, 5% saline solution/methanol=1:1).

c. 2-tert.butyloxycarbonylamino-2-(4-chloro-3-nitro-phenyl)-propionic acid

Prepared analogously to Example 5d from 2-amino-2-(4-chloro-3-nitro-phenyl)-propionic acid, di-tert.butyl pyrocarbonate and triethylamine in dioxane.

Yield: 9.6 g (100% of theory), $R_f$ value: 0.31 (Reversed phase RP8, 5% saline solution/methanol=1:2).

d. 2-(4-chloro-3-nitro-phenyl)-2-tert.butyloxycarbonylamino-1-(pyrrolidin-1-yl)-propanone Prepared analogously to Example 1c from 2-tert.butyloxycarbonylamino-2-(4-chloro-3-nitro-phenyl)-propionic acid, O-(benzotriazol-1-yl)-N,N,N',N'-tetramethyluronium tetrafluoroborate, pyrrolidine and N-methylmorpholine in dimethylformamide.

Yield: 94% of theory, $R_f$ value: 0.11 (silica gel; cyclohexane/ethyl acetate=1:1).

e. 2-(4-methylamino-3-nitro-phenyl)-2-tert.butyloxycarbonylamino-1-(pyrrolidin-1-yl)-propanone Prepared analogously to Example 1b from 2-(4-chloro-3-nitro-phenyl)-2-tert.butyloxycarbonylamino-1-(pyrrolidin-1-yl)-pro-panone and methylamine solution in dimethylformamide at 160° C. $R_f$ value: 0.79 (silica gel; ethyl acetate/ethanol=9:1)

f. 2-(4-methylamino-3-amino-phenyl)-2-tert.butyloxycarbonyl-amino-1-pyrrolidin-1-yl-propanone Prepared analogously to Example 1d from 2-(4-methylamino-3-nitro-phenyl)-2-tert.butyloxycarbonylamino-1-(pyrrolidin-1-yl)-propanone and palladium on activated charcoal/hydrogen in methanol.

Yield: 100% of theory, $R_f$ value: 0.63 (silica gel; ethyl acetate/ethanol×9:1).

g. 2-[4-methylamino-3-(4-cyanophenylaminomethyl-carbonylamino)-phenyl]-2-tert.butyloxycarbonylamino-1-(pyrrolidin-1-yl)-propanone Prepared analogously to Example 1c from 2-(4-methylamino-3-amino-phenyl)-2-tert.butyloxycarbonylamino-1-(pyrrolidin-1-yl)-propanone, O-(benzotriazol-1-yl)-N,N,N',N'-tetramethyluronium tetrafluoroborate, 4-cyano-phenylglycine and N-methylmorpholine in dimethylformamide.

Yield: 37% of theory, $R_f$ value: 0.47 (silica gel; ethyl acetate).

h. 2-(4-cyanophenylaminomethyl)-1-methyl-5-[1-(N-tert.butyloxycarbonylamino)-1-(pyrrolidin-1-yl-carbonyl)-ethyl]-benzimidazole Prepared analogously to Example 1f from 2-[4-methylamino-3-(4-cyanophenylaminomethylcarbonylamino)-phenyl]-2-tert.butyloxycarbonylamino-1-(pyrrolidin-1-yl)-propanone and glacial acetic acid.

Yield: 60% of theory, $R_f$ value: 0.37 (silica gel; ethyl acetate).

i. 2-(4-cyanophenylaminomethyl)-1-methyl-5-[1-amino-1-(pyrrolidin-1-yl-carbonyl)-ethyl]-benzimidazole 1.3 g (2.3 mmol) of 2-(4-cyanophenylaminomethyl)-1-methyl-5-[1-(N-tert.butyloxycarbonylamino)-1-(pyrrolidin-1-yl-carbonyl)-ethyl]-benzimidazole are dissolved in 20 ml dioxane and, after the addition of 40 ml of semiconc. hydrochloric acid, stirred for two hours at ambient temperature. The solution is mixed with ice, made alkaline with ammonia and extracted with ethyl acetate. The combined organic extracts are dried and concentra-ted by evaporation.

Yield: 0.9 g (98% of theory), $R_f$ value: 0.14 (silica gel; ethyl acetate/ethanol=9:1).

k. 2-(4-cyanophenylaminomethyl)-1-methyl-5-[1-[N-(2-ethoxycarbonylethyl)-amino]-1-(pyrrolidin-1-yl-carbonyl)-ethyl]-benzimidazole 0.4 g (1.04 mmol) of 2-(4-cyanophenylaminomethyl)-1-methyl-5-[1-amino-1-(pyrrolidin-1-yl-carbonyl)-ethyl]-benzimidazole are dissolved in 10 ml ethanol and after the addition of 0.3 ml (2.7 mmol) of ethyl acrylate stirred for 24 hours at 95° C. The solvent is distilled off and the residue is chromatographed on silica gel, eluting with methylene chloride/ethanol (20:1 and 4:1).

Yield: 0.16 g (31% of theory), $R_f$ value: 0.26 (silica gel; ethyl acetate/ethanol=9:1).

l. 2-(4-amidinophenylaminomethyl)-1-methyl-5-[1-[N-(2-ethoxycarbonylethyl)-amino]-1-(pyrrolidin-1-yl-carbonyl)-ethyl]-benzimidazole-hydrochloride Prepared analogously to Example 1g from 2-(4-cyanophenylaminomethyl)-1-methyl-5-[1-[N-(2-ethoxycarbonylethyl)-amino]-1-(pyrrolidin-1-yl-carbonyl)-ethyl]-benzimidazole and hydrochloric acid/ammonium carbonate in ethanol.

Yield: 96% of theory, $C_{28}H_{37}N_7O_3 \times HCl$ (519.65/556.11).

mass spectrum: $(M+H)^+ = 520$
$(M+Na)^+ = 542$

The following compounds are obtained analogously to Example 6:

(1) 2-(4-amidinophenylaminomethyl)-1-methyl-5-[1-(3-ethoxycarbonylpropionylamino)-1-ethoxycarbonyl-ethyl]-benzimidazole-hydrochloride Yield: 69% of theory, $C_{27}H_{34}N_6O_5 \times HCl$ (522.62/555.08).

mass spectrum: $(M+H)^+ = 523$
$(M+H+Na)^{++} = 273$ (2) 2-(4-amidinophenylaminomethyl)-1-methyl-5-[1-(ethoxycarbonylmethylcarbonylamino)-1-(pyrrolidin-1-yl-carbonyl)-ethyl]-benzimidazole-hydrochloride Yield: 95% of theory, $C_{28}H_{35}N_7O_4 \times HCl$ (533.64/570.10).

mass spectrum: $(M+H)^+ = 534$
$(M+Na)^+ = 556$ (3) 2-(4-amidinophenylaminomethyl)-1-methyl-5-[1-(3-ethoxycarbonylpropionylamino)-1-(pyrrolidin-1-yl-carbonyl)-ethyl]-benzimidazole-hydrochloride Yield: 20% of theory, $C_{29}H_{37}N_7O_4 \times HCl$ (547.66/584.12).

mass spectrum: $(M+H)^+ = 548$
$(M+H+Na)^{++} = 285.7$ (4) 2-[4-amidinophenyl-N-(2-ethoxycarboniylethyl)-aminomethyl]-1-methyl-5-[1-dimethylamino-1-(pyrrolidin-1-yl-carbonyl)-ethyl]-benzimidazole-hydrochloride Yield: 91% of theory, $C_{30}H_{41}N_7O_3 \times HCl$ (547.71/584.17).

mass spectrum: $(M+H)^+ = 548$
$(M-H)^- = 546$ (5) 2-(4-amidinophenylaminomethyl)-1-methyl-5-[1-(2-ethoxycarbonylethylamino)-1-(dimethylaminocarbonyl)-ethyl]-benzimidazole-hydrochloride Yield: 40% of theory, $R_f$ value. 0.60 (Reversed phase RP 8; 5% saline solution/methanol=1/1); $C_{26}H_{35}N_7O_3 \times HCl$ (493.63/530.08).

mass spectrum: $(M+H)^+ = 494$
$(M-H+2HCl)^- = 564/566/568$ ($Cl_2$)

(6) 2-(4-amidinophenylaminomethyl)-1-methyl-5-[1-(ethoxycarbonylmethylamino)-1-(pyrrolidin-1-yl-carbonyl)-ethyl]-benzimidazole-hydrochloride Yield: 77% of theory, $R_f$ value: 0.40 (silica gel; methylene chloride/methanol=4:1+1% glacial acetic acid) $C_{27}H_{35}N_7O_3 \times HCl$ (505.63/542.08); mass spectrum: $(M+H)^+ = 506$.

(7) 2-(4-amidinophenylaminomethyl)-1-methyl5-[1-(2-ethoxycarbonylethyl-amino)-1-(N-ethyl-N-methylaminocarbonyl)-ethyl]-benzimidazole-hydrochloride Yield: 85% of theory, $R_F$ value: 0.44 (silica gel; methylene chloride/ethanol=9:1) $C_{27}H_{37}N_7O_3 \times HCl$ (507.64/544.14).

mass spectrum: $(M+H)^+ = 508$
$(M+Cl)^- = 542/4$ (Cl)

(8) 2-(4-amidinophenylaminomethyl)-1-methyl-5-[1-(methoxycarbonylmethylamino)-1-(pyrrolidinocarbonyl)-ethyl]-benzimidazole-hydrochloride Yield: 99% of theory, $R_f$ value: 0.21 (silica gel; methylene chloride/methanol=4:1+1% glacial acetic acid); $C_{26}H_{33}N_7O_3 \times HCl$ (491.60/528.05).

mass spectrum: $(M+H)^+ = 492$
$(M-H+HCl)^- = 526/8$ (Cl)
$(M-H+2HCl)^- = 562/4/8$ ($Cl_2$)

(9) 2-(4-amidinophenylaminomethyl)-1-methyl-5-[1-(N,N-bis(ethoxycarbonylmethyl)amino)-1-(pyrrolidinocarbonyl)-ethyl]-benzimidazole-hydrochloride Yield: 65% of theory, $R_f$ value: 0.35 (silica gel; methylene chloride/methanol=4:1+1% glacial acetic acid) $C_{31}H_{41}N_7O_5 \times HCl$ (591.72/628.17).

mass spectrum: $(M+H)^+ = 592$
$(M-H+HCl)^- = 626/8$ (Cl)
$(M-H+2HCl)^- = 662/4/6$ ($Cl_2$)

(10) 2-(4-amidinophenylaminomethyl)-1-methyl-5-[1-(ethoxycarbonylmethylamino)-1-(isoxazolidin-1-yl-carbonyl)-ethyl]-benzimidazole-hydrochloride Yield: 9% of theory, $R_f$ value: 0.50 (Reversed phase RP 8; methanol/5% saline solution=3:2) $C_{26}H_{33}N_7O_4 \times HCl$ (507.60/544.05); mass spectrum: $(M+H)^+=508$.

(11) 2-(4-amidinophenylaminomethyl)-1-methyl-5-[1-(2-ethoxycarbonyl-ethylamino)-1-(isoxazolidin-1-yl-carbonyl)-ethyl]-benzimidazole-hydrochloride

(12) 2-(4-amidinophenylaminomethyl)-1-methyl-5-[1-(ethoxycarbonylmethylamino)-1-(N-methyl-N-ethylaminocarbonyl)-ethyl]-benzimidazole-dihydrochloride Yield: 58% of theory, $R_f$ value: 0.70 (Reversed phase RP 8; methanol/5% saline solution=3:2); $C_{26}H_{35}N_7O_3 \times 2$ HCl (493.62/566.52).

mass spectrum: $(M+H)^+$ = 494

$(M+HCl-H)^-$ = 528/30 (Cl)

(13) 2-(4-amidinophenylaminomethyl)-1-methyl-5-[1-((N,N-di-(ethoxycarbonylmethyl)-amino)-1-(N-methyl-N-ethylaminocarbonyl)-ethyl]-benzimidazole-dihydrochloride Yield: 30% of theory, $R_f$ value: 0.40 (Reversed phase RP 8; methanol/5% saline solution=3:2); $C_{30}H_{41}N_7O_5 \times 2$ HCl (579.71/652.62).

mass spectrum: $(M+H)^+$ = 580

$(M-H)^-$ = 578

(14) 2-(4-amidinophenylaminomethyl)-1-methyl-5-[1-(ethoxycarbonylmethylamino)-1-(piperidinocarbonyl)-ethyl]-benzimidazole-dihydrochloride Yield: 82% of theory, $R_f$ value: 0.60 (Reversed phase RP 8; methanol/5% saline solution=3:2); $C_{28}H_{37}N_7O_3 \times 2$ HCl (519.65/592.75).

mass spectrum: $(M+H)^+$ = 520

$(M-H+HCl)^-$ = 534/6 (Cl)

$(M-H+2HCl)^-$ = 590/2/4 (Cl$_2$)

(15) 2-(4-amidinophenylaminomethyl)-1-methyl-5-[1-(ethoxycarbonylmethylamino)-1-(diethylaminocarbonyl)-ethyl]-benzimidazole-dihydrochloride Yield: 88% of theory, $R_f$ value: 0.60 (Reversed Phase RP 8; methanol/5% saline solution=3:2); $C_{27}H_{37}N_7O_3 \times 2$ HCl (507.64/580.56).

mass spectrum: $(M+H)^+$ = 508

$(M-H+2HCl)^-$ = 578/580/582 (Cl$_2$)

(16) 2-(4-amidinophenylaminomethyl)-1-methyl-5-[1-(ethoxycarbonylmethylamino)-1-(pyrrolin-1-yl-carbonyl)-ethyl]-benzimidazole-dihydrochloride Yield: % of theory, $C_{27}H_{33}N_7O_3 \times 2$ HCl (503.61/576.51) mass spectrum:

(17) 2-(4-amidinophenylaminomethyl)-1-methyl-5-[1-(ethoxycarbonylmethyl-methylamino)-1-(pyrrolidin-1-yl-carbonyl)-ethyl]-benzimidazole-dihydrochloride Yield: % of theory, $C_{28}H_{35}N_7O_3 \times 2$ HCl (517.64/590.54) mass spectrum:

(18) 2-(4-amidinophenylaminomethyl)-1-methyl-5-[1-(tetrazol-5-yl-methylamino)-1-(pyrrolidin-1-yl-carbonyl)-ethyl]-benzimidazole-dihydrochloride

(19) 2-(4-amidinophenylaminomethyl)-1-methyl-5-[1-(3-ethoxycarbonyl-propylamino)-1-(pyrrolidin-1-yl-carbonyl)-ethyl]-benzimidazole-dihydrochloride Yield: 95% of theory, $R_f$ value: 0.50 (Reversed Phase RP 8; methanol/5% saline solution=1:1); $C_{29}H_{39}N_7O_3 \times 2$ HCl (533.68/606.58); mass spectrum: $(M+H)^+$=534.

EXAMPLE 7

2-(4-amidinophenylaminomethyl)-1-methyl-5-[1-[N-cyclopentyl-N-(3-ethoxycarbonylpropionyl)-amino] cyclopropyl]-benzimidazole-hydrochloride a. 4-((1-tert.butyloxycarbonylamino)cyclopropyl)-2-nitro-N-methyl-aniline 15.0 g (63.5 mmol) of 4-((1-carboxy)cyclopropyl)-2-nitro-N-methyl-aniline and 17.6 ml (127 mmol) of triethylamine are dissolved in 250 ml of dichloromethane and 8.3 g (76 mmol) of ethyl chloroformate are added at 0° C. After one hour at ambient temperature 0.75 g tetrabutylammonium bromide are added. Then a solution of 6.3 g (96 mmol) of sodium azide in 20 ml water is added dropwise. After one hour at 0° C. the solution is diluted with water and extracted with ethyl acetate. The organic extracts are dried and concentrated by evaporation. The residue is dissolved in 200 ml tert.butanol and refluxed for two hours. The solvent is concentrated by evaporation, the residue chromatographed on silica gel and eluted with methylene chloride.

Yield: 15.5 g (77% of theory), $R_f$ value: 0.83 (silica gel; methylene chloride/methanol=9.5:0.5).

b. 4-((1-amino)cyclopropyl)-2-nitro-N-methyl-aniline-hydrochloride 15.5 g (0.05 mol) of 4-[(1-tert.butyloxycarbonylamino)-cyclopropyl]-2-nitro-N-methyl-aniline are dissolved in 50 ml ethanol and 50 ml elhanolic hydrochloric acid and stirred for 7 hours at ambient temperature. The solvent is distilled off, the residue triturated with ether, suction filtered and dried. Yield: 98% of theory, $R_f$ value: 0.44 (silica gel; methylene chloride/methanol=9.5:0.5).

c. 4-[N-(1-cyclopentylamino)cyclopropyl]-2-nitro-N-methyl-aniline 12.0 g (0.05 mol) of 4-[(1-amino)cyclopropyl]-2-nitro-N-methyl-aniline-hydrochloride are dissolved in 500 ml of tetrahydrofuran and after the addition of 4.1 g (0.05 mol) of cyclopentanone and 3.2 ml of glacial acetic acid, 13.6 g (0.064 mol) of sodium triacetoxyborohydride are added batchwise under a nitrogen atmosphere. After 16 hours at ambient temperature, the mixture is diluted with sodium hydrogen carbonate solution and extracted with ethyl acetate. The organic extracts are dried and concentrated by evaporation. The residue is chromatographed on silica gel and eluted with ethyl acetate/cyclohexane (1:1).

Yield: 10.8 g (80% of theory) $R_f$ value: 0.56 (silica gel; methylene chloride/methanol=9.5:0.5).

d. 4-[1-(N-(3-ethoxycarbonylpropionyl)-N-cyclopentyl-amino)-cyclopropyl]-2-nitro-N-methyl-aniline 1.0 g (3.6 mmol) of 4-[(1-cyclopentylamino) cyclopropyl]-2-nitro-N-methyl-aniline are dissolved in 30 ml tetrahydrofuran and after the addition of 0.45 g (4.4 mmol) of triethylamine, 0.65 g (4.4 mmol) of ethyl succinate chloride are added and the resulting mixture is stirred for four hours at ambient temperature. Then it is diluted with ethyl acetate and sodium hydrogen carbonate solution, the organic extracts are dried and concentrated by evaporation. The residue is chromatographed on silica gel, eluting with ethyl acetate/cyclohexane (1:1).

Yield: 1.3 g (90% of theory), $R_f$ value: 0.46 (silica gel; ethyl acetate/cyclohexane=1:1).

e. 4-[1-(N-(3-ethoxycarbonylpropionyl)-N-cyclopentyl-amino)-cyclopropyl]-2-amino-N-methyl-aniline Prepared analogously to Example 1d 4-[1-(N-(3-ethoxycarbonyl-propionyl)-N-cyclopentyl-amino) cyclopropyl]-2-nitro-N-methyl-aniline and palladium on activated charcoal/hydrogen in methylene chloride/ethanol.

Yield: 100% of theory, $R_f$ value: 0.18 (silica gel; ethyl acetate/cyclohexane=1:1).

f. 4-[1-(N-(3-ethoxycarbonylpropionyl)-N-cyclopentyl-amino)-cyclopropyl]-2-(4-cyanophenyl)-aminomethylcarbonylamino-N-methyl-aniline Prepared analogously to Example 1c 4-[1-(N-(3-ethoxycarbonyl-propionyl)-N-cyclopentyl-amino) cyclopropyl]-2-amino-N-methyl-aniline, O-(benzotriazol-1- yl)-N,N,N',N'-tetramethyluronium tetrafluoroborate, 4-cyano-phenylglycine and triethylamine in dimethylformamide.

Yield: 96% of theory, $R_f$ value: 0.54 (silica gel; methylene chloride/methanol=9.5:0.5)

g. 2-(4-cyanophenylaminomethyl)-1-methyl-5-[1-[N-cyclopentyl-N-(3-ethoxycarbonylpropionyl)-amino]-cyclopropyl]-benzimidazole Prepared analogously to Example 1f from 4-[1-(N-(3-ethoxycarbo-nylpropionyl)-N-cyclopentyl-amino) cyclopropyl]-2-(4-cyanophenyl)-aminomethylcarbonylamino-N-methyl-aniline in glacial acetic acid.

Yield: 52% of theory, $R_f$ value: 0.81 (silica gel; methylene chloride/methanol=9:1).

h. 2-(4-amidinophenylaminomethyl)-1-methyl-5-[1-[N-cyclopentyl-N-(3-ethoxycarbonylpropionyl)-amino] cyclopropyl]-benzimidazole-hydrochloride Prepared analogously to Example 1g from 2-(4-cyanophenylamino-methyl)-1-methyl-5-[1-[N-cyclopentyl-N-(3-ethoxycarbonylpropionyl)-amino]cyclopropyl]-benzimidazole and hydrochloric acid/ammonium carbonate in ethanol.

Yield: 36% of theory, $C_{30}H_{38}N_6N_3 \times HCl$ (530.68/567.14); mass spectrum: $(M+H)^+=531$.

EXAMPLE 8

2-(4-amidinophenylaminomethyl)-1-methyl-5-(5-methyl-3-ethoxycarbonylmethyl-imidazolin-2,4-dion-5-yl)benzimidazole-hydrochloride a. 2-(4-cyanophenylaminomethyl)-1-methyl-5-[1-(ethoxycarbonyl-methylaminocarbonylamino)-1-(pyrrolidin-1-yl-carbonyl)-ethyl]-benzimidazole 1.0 g (2.5 mmol) of 2-(4-cyanophenylaminomethyl)-1-methyl-5-[1-amino-1-(pyrrolidin-1-yl-carbonyl)-ethyl]-benzimidazole are dissolved in 10 ml dimethylformamide and after the addition of 0.9 ml (7.9 mmol) of ethyl isocyanatoacetate stirred for 45 minutes at ambient temperature. The solution is poured onto ice water, the crystalline product is suction filtered and dried. The residue is chromatographed on silica gel, eluting with methylene chloride/ethanol/ammonia (20:1:0.01 and 10:1:0.01).

$R_f$ value: 0.77 (silica gel; methylene chloride/ethanol/ammonia=9:1:0.01).

b. 2-(4-amidinophenylaminomethyl)-1-methyl-5-(5-methyl-3-ethoxycarbonylmethyl-imidazolin-2,4-dion-5-yl)-benzimidazole-hydrochloride Prepared analogously to Example 1g from 2-(4-cyanophenylamino-methyl)-1-methyl-5-[1-(ethoxycarbonylmethylaminocarbonylamino)-1-(pyrrolidin-1-yl-carbonyl)-ethyl]-benzimidazole and hydrochloric acid/ammonium carbonate in ethanol.

Yield: 68% of theory, $C_{24}H_{27}N_7O_4 \times HCl$ (477.52/513.99) mass spectrum: $(M+H)^+=478$.

EXAMPLE 9

2-(4-amidinophenylaminomethyl)-1-methyl-5-[N-(2-pyridyl)-N-(2-ethoxycarbonylethyl)-aminomethyl]-benzimidazole-hydrochloride a. 4-(2-tert.butyloxycarbonylethyl)-2-(pyridylaminomethyl)-2-nitro-chlorobenzene 13.4 g (0.053 mol) of 4-chloro-3-nitro-benzylbromide and 11.8 g (0.053 mol) of 2-tert.butyloxycarbonylethylamino-pyridine are stirred in 80 ml of N-ethyl-diisopropylamine for 3 hours at 90° C. The solution is concentrated by evaporation, the residue chromatographed on silica gel, eluting with petroleum ether/-ethyl acetate (8:2 and 7:3).

Yield: 8.2 g (40% of theory), $R_f$ value: 0.64 (silica gel; petroleum ether/ethyl acetate=8:2).

b. 4-(2-tert.butyloxycarbonylethyl)-2-(pyridyl-aminomethyl)-2-nitro-N-methyl-aniline Prepared analogously to Example 1b from 4-(2-tert.butyloxycarbonylethyl)-2-(pyridylaminomethyl)-2-nitro-chlorobenzene and methylamine solution.

Yield: 20% of theory, $R_f$ value: 0.65 (silica gel; methylene chloride/ethanol=9:1).

c. 4-(2-tert.butyloxycarbonylethyl)-2-(pyridyl-aminomethyl)-2-amino-N-methyl-aniline 1.6 g (4 mmol) of 4-(2-tert.butyloxycarbonylethyl)-2-(pyridylaminomethyl)-2-nitro-N-methyl-aniline are dissolved in 200 ml methanol and, after the addition of 2 g of Raney nickel, combined with 1 ml of hydrazine hydrate. The solution is stirred for 30 minutes at ambient temperature and concentrated by evaporation. The residue is chromatographed on silica gel and eluted with methylene chloride/ethanol (95:5).

Yield: 1.2 g (82% of theory), $R_f$ value: 0.33 (silica gel; methylene chloride/ethanol=9:1).

d. 2-(4-cyanophenylaminomethyl)-1-methyl-5-[N-(2-pyridyl)-N-(2-ethoxycarbonylethyl)-aminomethyl]-benzimidazole Prepared analogously to Example 1c from 4-(2-tert.butyloxycarbonylethyl)-2-(pyridylaminomethyl)-2-amino-N-methyl-aniline, O-(benzotriazol-1-yl)-N,N,N',N'-tetramethyluronium tetrafluo-roborate, 4-cyano-phenylglycine in tetrahydrofuran and glacial acetic acid.

Yield: 72% of theory, $R_f$ value: 0.36 (silica gel; methylene chloride/ethanol=9:1).

e. 2-(4-amidinophenylaminomethyl)-1-methyl-5-[N-(2-pyridyl)-N-(2-ethoxycarbonylethyl)-aminomethyl]-benzimidazole-hydrochloride Prepared analogously to Example 1g from 4-[(5-(2-tert.butyloxycarbonylethyl)-2-pyridylaminomethyl-1-methyl-benzimidazole-2-yl)-methylamino]-benzonitrile and hydrochloric acid/ammonium carbonate in ethanol.

Yield: 59% of theory, $C_{27}H_{31}N_7O_2 \times HCl$ (485.59/522.1) mass spectrum: $(M+H)^+=486$.

The following compounds are obtained analogously to Example 9:

(1) 2-(4-amidinophenylaminomethyl)-1-methyl-5-[N-(ethoxycarbonylmethyl)-benzenesulphonylaminomethyl]-benzimidazole-hydrochloride Yield: 53% of theory, $C_{27}H_{30}N_6O_4S \times HCl$ (534.64/571.1); mass spectrum: $(M+H)^+=535$.

(2) 2-(4-amidinophenylaminomethyl)-1-methyl-5-(N-methyl-phenylcarbonylaminomethyl)]-benzimidazole-hydrochloride Yield: 42% of theory, $C_{25}H_{26}N_6O \times HCl$ (426.53/462.96); mass spectrum: $(M+H)^+=427$.

EXAMPLE 10

2-(4-amidinophenylaminomethyl)-1-methyl-5-[(2-methylbenzimidazol-1-yl)methyl]-benzimidazole-hydrochloride a. 1-(4-chloro-3-nitrobenzyl)-2-methyl-benzimidazole Prepared analogously to Example 9a from 2-methyl-benzimidazole and 4-chloro-3-nitrobenzyl chloride in dimethylsulphoxide.

Yield: 78% of theory, $C_{15}H_{12}ClN_3O_2$ (301.7); mass spectrum: $M^+=301/303$.

b. 1-(4-methylamino-3-nitrobenzyl)-2-methyl-benzimidazole

Prepared analogously to Example 1b from 1-(4-chloro-3-nitrobenzyl)-2-methyl-benzimidazole and methylamine.

Yield: 96% of theory, $R_f$ value: 0.56 (silica gel; methylene chloride/ethanol=19:1).

c. 1-(4-methylamino-3-aminobenzyl)-2-methyl-benzimidazole

Prepared analogously to Example 1c from 1-(4-methylamino-3-nitrobenzyl)-2-methyl-benzimidazole and hydrogen/Raney nickel.

Yield: 100% of theory, $R_f$ value: 0.34 (silica gel; methylene chloride/ethanol=19:1).

d. 2-(4-cyanophenylaminomethyl)-1-methyl-5-[(2-methylbenzimidazol-1-yl)methyl]-benzimidazole A mixture of 1.94 g (11.0 mmol) of N-(4-cyanophenyl)-glycine and 1.78 g (11.0 mmol) of carbonyldiimidazole is refluxed in 80 ml of absolute tetrahydrofuran for 15 minutes. After the addition of 2.7 g (10.46 mmol) of 1-(4-methylamino-3-aminobenzyl)-2-methyl-benzimidazole the mixture is refluxed for a further 16 hours. Then the solution is evaporated to dryness, the residue is mixed with 80 ml glacial acetic acid and refluxed for 1 hour. It is then evaporated to dryness once more, the residue thus obtained is mixed with 50 ml of water and made alkaline with conc. ammonia (about pH 10). The product which crystallises out is suction filtered, washed with a little water and dried.

Yield: 4.1 g (96% of theory), $R_f$ value: 0.30 (silica gel; methylene chloride/ethanol=19:1) $C_{25}H_{22}N_6$ (406.5); mass spectrum: $M^+$=406.

e. 2-(4-amidinophenylaminomethyl)-1-methyl-5-[(2-methyl-benzimidazol-1-yl)methyl]-benzimidazole-hydrochloride Prepared analogously to Example 1g from 2-(4-cyanophenylaminomethyl)-1-methyl-5-[(2-methyl-benzimidazol-1-yl)methyl]-benzimidazole hydrochloric acid/ammonium carbonate.

Yield: 59% of theory, $C_{25}H_{25}N_7 \times HCl$ (423.5/459.9).

mass spectrum: $(M+H)^+$ = 424
$(M+2H)^{2+}$ = 217.7

The following compounds are obtained analogously to Example 10:

(1) 2-(4-amidinophenyloxymethyl)-1-methyl-5-[(imidazol-1-yl)-methyl]-benzimidazole-hydrochloride Yield: 30% of theory, $C_{20}H_{20}N_6O \times HCl$ (360.4/396.9).

mass spectrum: $(M+H)^+$ = 361
$(M+2H)^{2+}$ = 181

(2) 2-(4-amidinophenylaminomethyl)-1-methyl-5-[1-(imidazol-1-yl)-ethyl]-benzimidazole-hydrochloride Yield: 70% of theory, $C_{21}H_{23}N_7 \times HCl$ (373.46/410).

mass spectrum: $(M+H)^+$ = 374
$(M+2H)^{2+}$ = 187.6

(3) 2-(4-amidinophenylaminomethyl)-1-methyl-5-[1-(2-ethyl-4-methyl-imidazol-1-yl)-ethyl]-benzimidazole-dihydrochloride Yield: 18% of theory, $C_{24}H_{29}N_7 \times 2HCl$ (415.55/488.46).

mass spectrum: $(M+H)^+$ = 416
$(M+2H)^{2+}$ = 208.7

(4) 2-(4-amidinophenylaminomethyl)-1-methyl-5-[(2-ethyl-4-methyl-imidazol-1-yl)-methyl]-benzimidazole-dihydrochloride Yield: 36% of theory, $C_{23}H_{27}N_7 \times 2HCl$ (401.52/437.97).

mass spectrum: $(M+H)^+$ = 402
$(M+2H)^{2+}$ = 201.7

(5) 2-(4-amidinophenylaminomethyl)-1-methyl-5-[N-(pyridin-2-yl)-N-methyl-aminomethyl]-benzimidazole-dihydrochloride Yield: 78% of theory, $C_{23}H_{25}N_7 \times 2HCl$ (399.5/435.95).

mass spectrum: $(M+H)^+$ = 400
$(M+2H)^{2+}$ = 200.6

(6) 2-(4-amidinophenylaminomethyl)-1-methyl-5-[(2-(2-ethoxycarbonyl-ethyl)-benzimidazol-1-yl)-methyl]-benzimidazole-dihydrochloride Yield: 61% of theory, $C_{29}H_{31}N_7O_2 \times HCl$ (509.62/546.07).

mass spectrum: $(M+H)^+$ = 510
$(M+2H)^{2+}$ = 255.7
$(M+H+Na)^{2+}$ = 266.7

(7) 2-(4-amidinophenylaminomethyl)-1-methyl-5-[(imidazol-1-yl)-methyl]-benzimidazole-hydrochloride Yield: 35% of theory, $C_{20}H_{21}N_7 \times HCl$ (359.44/395.89).

mass spectrum: $(M+H)^+$ = 360
$(M+2H)^{2+}$ = 180.6

(8) 2-(4-amidinophenylaminomethyl)-1-methyl-5-[(2-(2-acetylamino-ethyl)-4,5-dimethyl-imidazol-1-yl)-methyl]-benzimidazole-dihydrochloride Yield: 42% of theory, $C_{26}H_{32}N_8O \times 2HCl$ (472.6/545.51).

mass spectrum: $(M+H)^+$ = 473
$(M+2H)^{2+}$ = 237
$(M+H+Na)^{2+}$ = 248

(9) 2-(4-amidinophenylaminomethyl)-1-methyl-5-[(2-(2-aminocarbonyl-ethyl)-4,5-dimethyl-imidazol-1-yl)-methyl]-benzimidazole-dihydrochloride Yield: 68% of theory, $C_{25}H_{30}N_8O \times 2HCl$ (458.6/531.51).

mass spectrum: $(M+H)^+$ = 459
$(M+2H)^{2+}$ = 230

(10) 2-(4-amidinophenylaminomethyl)-1-methyl-5-[(2-methyl-4-ethoxycarbonyl-imidazol-1-yl)-methyl]-benzimidazole-hydrochloride Yield: 34% of theory, $C_{24}H_{27}N_7O_2 \times HCl$ (445.53/481.98).

mass spectrum: $(M+H)^+$ = 446
$(M+2H)^{2+}$ = 223.5
$(M+H+Na)^{2+}$ = 234.5

(11) 2-(4-amidinophenylaminomethyl)-1-methyl-5-[(3-(3-ethoxycarbonyl-n-propyl)-benzimidazol-2-on-1-yl)-methyl]-benzimidazole-hydrochloride Yield: 58% of theory, $C_{30}H_{33}N_7O_3 \times HCl$ (539.64/576.09).

mass spectrum: $(M+H)^+$ = 540
$(M+H+Na)^{2+}$ = 281.7

(12) 2-(4-amidinophenylaminomethyl)-1-methyl-5-[(3-(2-ethoxycarbonyl-ethyl)-imidazo[4,5-b]pyridin-2-on-1-yl)-methyl]-benzimidazole-hydrochloride Yield: 29% of theory, $C_{28}H_{30}N_8O_3 \times HCl$ (526.6/563.05).

mass spectrum: $(M+H)^+$ = 527
$(M+2H)^{2+}$ = 264
$(M+H+Na)^{2+}$ = 275

(13) 2-(4-amidinophenylaminomethyl)-1-methyl-5-[(2-phenyl-imidazol-1-yl)-methyl]-benzimidazole-hydrochloride Yield: 58% of theory, $C_{26}H_{25}N_7 \times HCl$ (435.54/472).

mass spectrum: $(M+H)^+$ = 436
$(M+Na)^+$ = 218.6

(14) 2-(4-amidinophenylaminomethyl)-1-methyl-5-[(4,5-dimethyl-2-(2-ethoxycarbonylethyl)-imidazol-1-yl)-methyl]-benzimidazole-dihydrochloride Yield: 52% of theory, $C_{27}H_{33}N_7O_2 \times 2HCl$ (487.61/560.52).

mass spectrum: $(M+H)^+$ = 488
$(M+2H)^{2+}$ = 244.6

EXAMPLE 11

2-(4-amidinophenylaminomethyl)-1-methyl-5-[1-(2-ethoxycarbonylazetidin-1-yl)-1-(pyrrolidin-1-yl-carbonyl)-ethyl]-benzimidazole-hydrochloride a. 2-(4-cyanophenylaminomethyl)-1-methyl-5-[1-(2-tert.butyloxycarbonyl-azetidin-1-yl)-1-(pyrrolidin-1-yl-carbonyl)-ethyl]-benzimidazole 0.8 g (1.86 mmol) of 2-(4-cyanophenylaminomethyl)-1-methyl-5-[1-amino-1-(pyrrolidin-1-yl-carbonyl)-ethyl]-benzimidazole and 1.65 g ((5.5 mmol) of tert.butyl 2,4-dibromobutyrate are dissolved in 5 ml of ethanol, mixed with 0.2 g (1.86 mmol) of sodium carbonate and stirred under nitrogen for 30 hours at 55° C. After cooling, the white precipitate is filtered off and washed with ethanol. The filtrate is concentrated by evaporation, the residue is chromatographed on silica gel, eluting with ethyl acetate and ethyl acetate/ethanol/ammonia (20:1:0.01). The desired fractions are combined and concentrated by evaporation.

Yield: 0.44 g (44% of theory) as a mixture of diastereomers, $C_{31}H_{38}N_6O_3$ (542.69); mass spectrum: $(M+H)^+=543$.

b. 2-(4-amidinophenylaminomethyl)-1-methyl-5-[1-(2-ethoxycarbonyl-azetidin-1-yl)-1-(pyrrolidin-1-yl-carbonyl)-ethyl]-benzimidazole-hydrochloride (mixture of diastereomers)

Prepared analogously to Example 1g from 2-(4-cyanophenylaminomethyl)-1-methyl-5-[1-(2-tert.butyloxycarbonyl-azetidin-1-yl)-1-(pyrrolidin-1-yl-carbonyl)-ethyl]-benzimidazole and hydrochloric acid/ammonium carbonate in ethanol.

Yield: 12% of theory, $C_{29}H_{37}N_7O_3 \times HCl$ (531.66/568.12).

mass spectrum: $(M+H)^+$ = 532
$(M+H+HCl)^{2+}$ = 568/70 (Cl)

EXAMPLE 12

(E/Z)-2-(4-amidinophenylaminomethyl)-1-methyl-5-[1-[(pyridin-3-yl)-ethoxycarbonylmethylidene)-methylene]cyclopropyl]-benzimidazole-hydrochloride a. (E/Z)-2-(4-cyanophenylaminomethyl)-1-methyl-5-[1-[(pyridin-3-yl)-ethoxycarbonylmethylidene)-methylene]cyclopropyl]-benzimidazole 897 mg (4.0 mraol) of triethyl phosphonoacetate are dissolved in 30 ml tetrahydrofuran under argon. At −15° C. 449 mg (4.0 mmol) of potassium tert. butoxide are added. After 30 minutes 815 mg (2.0 mmol) of 2-(4-cyanophenylaminomethyl)-1-methyl-5-[1-(pyridin-3-yl-carbonyl)cyclopropyl]-benzimidazole are added batchwise and the mixture is stirred overnight at ambient temperature. Then the solution is refluxed for a further 6 hours and concentrated by evaporation. The residue is mixed with so-dium chloride solution and extracted 3× with ethyl acetate. The combined organic phases are dried over sodium sulphate and concentrated by evaporation. The residue is dissolved in dichloromethane and chromatographed on silica gel, eluting with dichlo-romethane containing 5% ethanol. The desired fractions are con-centrated by evaporation, the residue is triturated with ether, suction filtered and dried.

Yield: 365 mg (38% of theory).

b. ((E/Z)-2-(4-amidinophenylaminomethyl)-1-methyl-5-[1-[(pyridin-3-yl)-ethoxycarbonylmethylidene)-methylene]cyclopropyl]-benzimidazole-hydrochloride Prepared analogously to Example 1g from (E/Z)-2-(4-cyanophenylaminomethyl)-1-methyl-5-[1-[(pyridin-3-yl)-ethoxycarbonylmethylidene)-methylene]cyclopropyl]-benzimidazole and hydrochloric acid/ammonium carbonate in ethanol.

Yield: 58% of theory, $C_{29}H_{30}N_6O_2 \times HCl$ (494.60/531.05); mass spectrum: $(M+H)^+=495$.

The following compound is obtained analogously to Example 12:

(1) (E/Z)-2-(4-amidinophenylaminomethyl)-1-methyl-5-[1-[(pyridin-2-yl)-ethoxycarbonylmethylidene)-methylene]cyclopropyl]-benzimidazole-hydrochloride Yield: 72% of theory, $C_{29}H_{30}N_6O_2 \times HCl$ (494.60/531.05); mass spectrum: $(M+H)^{+-}495$.

EXAMPLE 13

2-(4-amidinophenylaminomethyl)-1-methyl-5-[1-(2-carboxy-azetidin-1-yl)-1-(pyrrolidin-1-yl-carbonyl)-ethyl]-benzimidazole-hydrochloride (mixture of diastereomers)

200 mg (0.35 mmol) of 2-(4-amidino-phenylaminomethyl)-1-methyl-5-[1-(2-ethoxycarbonylazetidin-1-yl)-1-(pyrrolidin-1-yl-carbonyl)-ethyl]-benzimidazole-hydrochloride are dissolved in 30 ml of 6N hydrochloric acid and stirred for 13 hours at ambient temperature. The reaction mixture is concentrated by evaporation with the addition of toluene, the residue is triturated with acetone/ether, suction filtered, washed with ether and dried.

Yield: 200 mg (>100% of theory, contains ammonium chloride), $C_{27}H_{33}N_7O_3 \times HCl$ (503.62/540.07); mass spectrum: $(M+H)^+=504$.

The following compounds are obtained analogously to Example 13:

(1) 2-(4-amidinophenylaminomethyl)-1-methyl-5-[1-(2-carboxyethylamino)-1-(dimethylaminocarbonyl)-ethyl]-benzimidazole-hydrochloride Yield: 91% of theory, $R_f$ value: 0.75 (Reversed phase; 5% saline solution/methanol=1:1) $C_{24}H_{31}N_7O_3 \times HCl$ (465.56/502.01).

mass spectrum: $(M + H)^+ = 466$
$(M - H + 2HCl)^- = 537/539 \ (Cl_2)$ (2) 2-(4-amidinophenylaminomethyl)-1-methyl-5-[1-(carboxymethylamino)-1-(pyrrolidin-1-yl-carbonyl)-ethyl]-benzimidazole-dihydrochloride Yield: 70% of theory, $R_F$ value: 0.51 (Reversed phase; 5% saline solution/methanol=3:2) $C_{25}H_{31}N_7O_3 \times 2\ HCl$ (477.57/550.48); mass spectrum: $(M+H)^+=478$.

(3) (E/Z)-2-(4-amidinophenylaminomethyl)-1-methyl-5-[1-[(pyridin-2-yl)-carboxymethylidene)-methylene]-cyclopropyl]-benzimidazole-hydrochloride Yield: 65% of theory, $C_{27}H_{26}N_6O_2 \times HCl$ (466.55/503.0).

mass spectrum: $(M + H)^+ = 467$
$(M + Cl)^+ = 501/503\ (Cl)$ (4) 2-(4-amidinophenylaminomethyl)-1-methyl-5-[1-(N-methylcarboxymethylcarbonylamino)-2-(pyrrolidinocarbonyl)-prop-2-yl]-benzimidazole-dihydrochloride Yield: 99% of theory, $R_f$ value: 0.55 (Reversed phase RP 8; methanol/5% saline solution=1:1); $C_{28}H_{35}N_7O_4 \times 2\ HCl$ (533.64/606.64).

mass spectrum: $(M + H)^+ = 534$
$(M - H)^- = 532$
$(M - H + HCl)^- = 568/570\ (Cl)$ (5) 2-(4-amidinophenylaminomethyl)-1-methyl-5-[1-(2-carboxyethyl-amino)-1-(N-ethyl-N-methylaminocarbonyl)-ethyl]-benzimidazole-dihydrochloride Yield: 75% of theory, $R_f$ value: 0.54 (Reversed phase RP 8; methanol/5% saline solution=1:1) $C_{25}H_{33}N_7O_3 \times 2\ HCl$ (479.59/552.59); mass spectrum: $(M+H)^+=480$.

EXAMPLE 14

2-[4-(N-hexyloxycarbonylamidino)-phenylaminomethyl]-1-methyl-5-[1-(2-ethoxycarbonylethylamino)-1-(dimethylaminocarbonyl)-ethyl]-benzimidazole 1.5 g (2.8 mmol) of 2-(4-amidinophenylaminomethyl)-1-methyl-5-[1-(2-ethoxycarbonylethylamino)-1-(dimethylaminocarbonyl)-ethyl]-benzimidazole-hydrochloride are dissolved in 14 ml water and 55 ml tetrahydrofuran, mixed with 2.0 g potassium carbonate and 1.0 ml (6 mmol) of hexyl chloroformate and stirred for 4 hours at ambient temperature. After removal of the solvent in vacuo the residue is; mixed with saline solution and extracted 3× with methylene chloride. The combined organic phases are washed with a little water, dried over magnesium sulphate and concentrated by evaporation. The crude product is purified on silica gel, eluting with methylene chloride plus 2 to 7.5% ethanol. The uniform fractions are combined, concentrated by evaporation, dissolved in a little ethyl acetate and mixed with petroleum ether. The solid form is suction filtered, washed with petroleum ether and dried.

Yield: 0.8 g (43% of theory), $C_{33}H_{47}N_7O_5$ (621.79); $R_f$ value: 0.50 (silica gel; methylene chloride/ethanol=19:1).

mass spectrum: $(M + H)^+ = 622$
$(M + Na)^+ = 644$

EXAMPLE 15

2-(4-amidinophenylaminomethyl)-1-methyl-5-[1-(N-ethoxycarbonylmethylcarbonyl-methylamino)-2-(pyrrolidinocarbonyl)-prop-2-yl]-benzimidazole-hydrochloride a. Methyl 2-(4-chloro-phenyl)-3-hydroxy-2-methyl-propionate 35 ml of a 1.6 molar solution of n-butyllithium in hexane (61 mmol) are added dropwise to a solution of 8.1 ml of diisopropylamine (85 mmol)l in 20 ml tetrahydrofuran at −78° C. Then a solution of 10.0 g (50 mmol) of methyl 2-(4-chloro-phenyl)-propionate in 30 ml tetrahydrofuran is added dropwise at −78° C. Formaldehyde gas is then piped into the reaction mixture at −20° C. for 30 minutes. After the addition of 5% citric acid and glacial acetic acid the mixture is extracted with ethyl acetate. The organic phases are washed with 1N sulphuric acid, water, saturated sodium bicarbonate solution and saline solution and dried over magnesium sulphate. The crude product is purified on silica gel, eluting with cyclohexane/ethyl acetate (19:1; 9:1; 4:1; 1:1 and 0:1). The uniform fractions are combined and concentrated by evaporation.

Yield: 9.7 g (84% of theory) yellow oil, $R_F$ value: 0.25 (silica gel; petroleum ether/ethyl acetate=4:1).

b. 2-(4-chloro-phenyl)-3-hydroxy-2-methyl-propionic Acid

Prepared analogously to Example 4 from methyl 2-(4-chlorophenyl)-3-hydroxy-2-methyl-propionate and sodium hydroxide solution in ethanol.

Yield: 83% of theory, $R_F$ value: 0.55 (silica gel; ethyl acetate/cyclohexane=2:1+glacial acetic acid).

c. 2-(4-chloro-3-nitro-phenyl)-2-methyl-3-nitroxy-propionic Acid

Prepared analogously to Example 1a from 2-(4-chloro-phenyl)-3-hydroxy-2-methyl-propionic acid and nitric acid.

Yield: 90% of theory, melting point: 129–132° C. $C_{10}H_9ClN_2O_7$ (304.64).

d. 2-(4-chloro-3-nitro-phenyl)-2-methyl-3-hydroxy-propionic Acid

Prepared analogously to Example 6 from 2-(4-chloro-3-nitro-phenyl)-3-nitrooxy-2-methyl-propionic acid and 6N hydrochloric acid in dioxane.

Yield: 98% of theory, $C_{10}H_{10}ClNO_5$ (259.65).

mass spectrum: $(M - H)^- = 258/60$ (Cl)
$(2M - H)^- = 517/9$ (Cl$_2$)

e. 2-[4-(N-benzyl-methylamino)-3-nitro-phenyl]-2-methyl-3-hydroxy-propionic Acid Prepared analogously to Example 1b from 2-(4-chloro-3-nitro-phenyl)-3-hydroxy-2-methyl-propionic acid and N-methyl-benzylamine.

Yield: 81% of theory, $C_{18}H_{20}ClN_2O_5$ (344.37); mass spectrum: M$^+$=344.

f. 2-[4-(N-benzyl-methylamino)-3-nitro-phenyl]-2-methyl-3-hydroxy-1-pyrrolidin-1-yl-propan-1-one Prepared analogously to Example 1c from 2-[4-(N-benzyl-methylamino)-3-nitro-phenyl]-3-hydroxy-2-methyl-propionic acid and N-methyl-benzylamine.

Yield: 96% of theory, $C_{22}H_{27}N_3O_4$ (397.48).

mass spectrum: M$^+$ = 398
$(M + Na)^+$ = 420 g. 2-[4-(N-benzyl-methylamino)-3-nitro-phenyl]-2-methyl-3-methanesulphonyloxy-1-pyrrolidin-1-yl-propan-1-one A solution of 1.2 g (3.0 mmol) of 2-[4-(N-benzyl-methylamino)-3-nitro-phenyl]-2-methyl-3-hydroxy-1-pyrrolidin-1-yl-propan-1-one in 20 ml tetrahydrofuran is mixed at ambient temperature with 1.3 ml (9.3 mmol) of triethylamine. Then 0.27 ml (3.5 mmol) of methanesulphonyl chloride are added dropwise at 2–5° C. After 2 hours at ambient temperature the precipitate formed is suction filtered and the filtrate is concentrated by evaporation. The crude product is further reacted without being purified.

Yield: 1.4 g (98% of theory).

h. 2-[4-(N-benzyl-methylamino)-3-nitro-phenyl]-2-methyl-3-methylamino-1-pyrrolidin-1-yl-propan-1-one A solution of 1.4 g (2.9 mmol) of 2-[4-(N-benzyl-methylamino)-3-nitro-phenyl]-2-methyl-3-methanesulphonyloxy-1-pyrrolidin-1-yl-propan-1-one in 10 ml dimethylformamide is combined with 20 ml of a 40% aqueous methylamine solution and heated to 100° C. for 70 minutes. After cooling the reaction mixture is combined with ice water and extracted with ethyl acetate. The organic phases are washed with water and with saline solution, dried over magnesium sulphate and concentrated by evaporation. The crude product is purified on silica gel, eluting with ethyl acetate/ethanol (10:1, 9:1, 4:1+1% conc. ammonia). The uniform fractions are combined and concentrated by evaporation.

Yield: 740 mg (61% of theory), $R_F$ value: 0.45 (silica gel; methylene chloride/ethanol=9:1+1% conc. ammonia).

i. 2-[4-(benzyl-methylamino)-3-nitro-phenyl]-2-methyl-3-(N-methoxycarbonylmethylcarbonyl-methylamino)-1-pyrrolidin-1-yl-propan-1-one Prepared analogously to Example 7d from 2-[4-(N-benzyl-methylamino)-3-nitro-phenyl]-2-methyl-3-methylamino-1-pyrrolidin-1-yl-propan-1-one and methyl malonate chloride.

Yield: 84% of theory, $R_F$ value: 0.65 (silica gel; ethyl acetate/ethanol=9:1+ammonia); $C_{27}H_{34}N_4O_6$ (510.60).

mass spectrum: $(M - H)^-$ = 509
$(M + Na)^+$ = 533 j. 2-(4-methylamino-3-amino-phenyl)-2-methyl-3-(N-methoxycarbonylmethylcarbonyl-methylamino)-1-pyrrolidin-1-yl-propan-1-one Prepared analogously to Example 1d from 2-[4-(N-benzyl-methyl-amino)-3-nitro-phenyl]-2-methyl-3-(N-methoxycarbonylmethylcarbonyl-methylamino)-1-pyrrolidin-1-yl-propan-1-one and hydrogen/palladium on activated charcoal.

Yield: 100% of theory, $R_F$ value: 0.40 (silica gel; ethyl acetate/ethanol=9:1+1% conc. ammonia) $C_{20}H_{30}N_4O_4$ (390.49); mass spectrum: M$^+$=390.

k. 4-[2-(3-(N-methoxycarbonylmethylcarbonyl-methylamino))-2-methyl-1-pyrrolidin-1-yl-propan-1-on-2-yl]-2-(4-cyanophenyl)-aminomethylcarbonylamino-N-methyl-aniline Prepared analogously to Example 1e from 2-(4-methylamino-3-amino-phenyl)-2-methyl-3-(N-methoxycarbonylmethylcarbonyl-methylamino)-1-pyrrolidin-1-yl-propan-1-one and O-(benzotriazol-1-yl)-N,N,N'N'-tetramethyluronium tetrafluoroborate, 4-cyanophenylglycine and triethylamine in dimethylformamide.

Yield: 95% of theory, $R_F$ value: 0.35 (silica gel; ethyl acetate/ethanol=9:1+1% conc. ammonia).

l. 2-(4-cyanophenylaminomethyl)-1-methyl-5-[1-(N-ethoxycarbonylmethylcarbonyl-methylamino)-2-(pyrrolidinocarbonyl)-prop-2-yl]-benzimidazole Prepared analogously to Example 1f from 4-[2-(3-(N-methoxycarbonylmethylcarbonyl-methylamino))-2-methyl-1-pyrrolidin-1-yl-propan-1-on-2-yl]-2-(4-cyanophenyl)-aminomethylcarbonylamino-N-methyl-aniline in glacial acetic acid.

Yield: 47% of theory, $R_f$ value: 0.20 (silica gel; ethyl acetate/ethanol=9:1); $C_{29}H_{34}N_6O_4$ (530.63).

mass spectrum: $(M + H)^+$ = 531
$(M + Na)^+$ = 553 m. 2-(4-amidinophenylaminomethyl)-1-methyl-5-[1-(N-ethoxycarbonylmethylcarbonyl-methylamino)-2-(pyrrolidinocarbonyl)-prop-2-yl]-benzimidazole-hydrochloride Prepared analogously to Example 1g from 2-(4-cyanophenylaminomethyl)-1-methyl-5-[1-(N-ethoxycarbonylmethylcarbonyl-methylamino)-2-(pyrrolidinocarbonyl)-prop-2-yl]-benzimidazole and hydrochloric acid/ammonium carbonate in ethanol.

Yield: 65% of theory, $R_f$ value: 0.30 (silica gel; methylene chloride/methanol=4:1+glacial acetic acid) $C_{30}H_{39}N_7O_4\times$ HCl (561.69/598.19).

mass spectrum: $(M + H)^+$ = 562
$(M + Cl)^-$ = 596/8 (Cl)

The following compounds are obtained analogously to Example 15:

(1) 2-(4-amidinophenylaminomethyl)-1-methyl-5-[1-(N-methoxycarbonylmethyl-methylamino)-2-(pyrrolidinocarbonyl)-prop-2-yl]-benzimidazole-hydrochloride Yield: 89% of theory, $R_f$ value: 0.35 (Reversed phase RP 8; methanol/5% saline solution=3:2); $C_{28}H_{37}N_7O_3 \times HCl$ (519.66/556.11).

mass spectrum: $(M+H)^+$ = 520

$(M-H+HCl)^-$ = 554/6 (Cl)

(2) 2-(4-amidinophenylaminomethyl)-1-methyl-5-[1-(N-ethoxycarbonylmethylcarbonylamino)-2-(pyrrolidinocarbonyl)-prop-2-yl]-benzimidazole-acetate Yield: 45% of theory, $R_f$ value: 0.20 (silica gel; methylene chloride/ethanol 8:2+1% ethyl acetate); $C_{29}H_{37}N_7O_4 \times CH_3COOH$ (547.66/607.71).

mass spectrum: $(M+H)^+$ = 548

$(M-H)^-$ = 546

$(M-H+CH_3COOH)^-$ = 606

(3) 2-(4-amidinophenylaminomethyl)-1-methyl-5-[1-(N-ethoxyarbonylmethylcarbonyl-methylamino)-2-(N-methyl-ethylaminocarbonyl)-prop-2-yl]-benzimidazole-hydrochloride.

(4) 2-(4-amidinophenylaminomethyl)-1-methyl-5-[1-(N-ethoxycarbonylmethyl-methylamino)-2-(N-methyl-N-ethylaminocarbonyl)-prop-2-yl]-benzimidazole-hydrochloride.

(5) 2-(4-amidinophenylaminomethyl)-1-methyl-5-[1-(N-ethoxycarbonylmethylcarbonyl-methylamino)-2-(piperidinocarbonyl)-prop-2-yl]-benzimidazole-hydrochloride.

(6) 2-(4-amidinophenylaminomethyl)-1-methyl-5-[1-(N-ethoxycarbonylmethylsulphonyl-methylamino)-2-(piperidinocarbonyl)-prop-2-yl]-benzimidazole-hydrochloride.

(7) 2-(4-amidinophenylaminomethyl)-1-methyl-5-[1-(N-methoxycarbonylmethylcarbonyl-methylamino)-2-(pyrrolidinocarbonyl)-prop-2-yl]-benzimidazole-acetate.

Yield: 72of theory, $R_f$ value: 0.20 (silica gel; methylene chloride/ethanol=8:2+1% glacial acetic acid); $C_{29}H_{37}N_7O_4 \times CH_3COOH$ (547.66/607.71).

mass spectrum: $(M+H)^+$ = 548

$(M-H)^-$ = 546

(8) 2-(4-amidinophenylaminomethyl)-1-methyl-5-[1-(2-ethoxycarbonyl-ethylcarbonylamino)-2-(pyrrolidinocarbonyl)-prop-2-yl]-benzimidazole-hydrochloride.

(9) 2-(4-amidinophenylaminomethyl)-1-methyl-5-[1-(ethoxycarbonylmethylsulphonylamino)-2-(pyrrolidinocarbonyl)-prop-2-yl]-benzimidazole-hydrochloride.

(10) 2-(4-amidinophenylaminomethyl)-1-methyl-5-[1-(1H-tetrazol-5-yl)-methylcarbonylamino)-2-(pyrrolidinocarbonyl)-prop-2-yl]-benzimidazole-hydrochloride.

(11) 2-(4-amidinophenylaminomethyl)-1-methyl-5-[1-(ethoxycarbonylmethylamino)-2-(:pyrrolidinocarbonyl)-prop-2-yl]-benzimidazole-dihydrochloride.

Yield: % of theory, $C_{28}H_{37}N_7O_3 \times 2$ HCl (519.65/592.56); mass spectrum:

EXAMPLE 16

2-(4-amidinophenylaminomethyl)-1-methyl-5-[1-(carboxymethylamino)-1-(isoxazolidin-1-yl-carbonyl)-ethyl]-benzimidazole-hydrochloride Prepared by hydrolysis of 2-(4-amidinophenylaminomethyl)-1-methyl-5-[1-(ethoxycarbonylmethylamino)-1-(isoxazolidin-1-yl-carbonyl)-ethyl]-benzimidazole-hydrochloride with sodium hydroxide solution in ethanol.

Yield: 90% of theory, $R_f$ value: 0.65 (Reversed phase RP 8; methanol/5% saline solution=3:2); $C_{24}H_{29}N_7O_4 \times HCl$ (479.54/515.99); mass spectrum: $(M+H)^+$=480.

The following compounds are prepared analogously to Example 16:

(1) 2-(4-amidinophenylaminomethyl)-1-methyl-5-[1-(2-carboxyethylamino)-1-(isoxazolidin-1-yl-carbonyl)-ethyl]-benzimidazole-hydrochloride.

(2) 2-(4-amidinophenylaminomethyl)-1-methyl-s-[1-(carboxymethylamino)-1-(N-methyl-N-ethylaminocarbonyl)-ethyl]-benzimidazole-hydrochloride.

Yield: 93% of theory, $R_f$ value: 0.40 (Reversed phase RP 8; methanol/5% saline solution=1:1); $C_{24}H_{31}N_7O_3 \times HCl$ (465.57/502.02).

mass spectrum: $(M+H)^+$ = 466

$(M+Cl-H)^-$ = 500/2 (Cl)

(3) 2-(4-amidinophenylaminomethyl)-1-methyl-5-[1-(N-carboxymethyl-methylamino)-2-(pyrrolidinocarbonyl)-prop-2-yl]-benzimidazole-dihydrochloride Yield: 89% of theory, $R_f$ value: 0.57 (Reversed phase RP 8; methanol/5% saline solution=4:3); $C_{27}H_{35}N_7O_3 \times 2$ HCl (505.63/578.54).

mass spectrum: $(M+H)^+$ = 506

$(M+2H)^{++}$ = 253

$(M+H+Na)^{++}$ = 264.5

(4) 2-(4-amidinophenylaminomethyl)-1-methyl-5-[1-(carboxymethylcarbonylamino)-2-(pyrrolidinocarbonyl)-prop-2-yl]-benzimidazole-hydrochloride.

Yield: 90% of theory, $R_f$ value: 0.55 (Reversed phase RP 8; methanol/5% saline solution=4:6); $C_{27}H_{33}N_7O_4 \times HCl$ (519.61/556.06).

mass spectrum: $(M+H)^+$ = 520

$(M-H)^-$ = 518

(5) 2-(4-amidinophenylaminomethyl)-1-methyl-5-[1-(N-carboxymethyl-methylamino)-2-(N-ethyl-methyl-aminocarbonyl)-prop-2-yl]-benzimidazole-hydrochloride.

(6) 2-(4-amidinophenylaminomethyl)-1-methyl-5-[1-(N-carboxyethylcarbonyl-methylamino)-2-(N-ethyl-methylaminocarbonyl)-prop-2-yl]-benzimidazole-hydrochloride.

(7) 2-(4-amidinophenylaminomethyl)-1-methyl-5-[1-(N-carboxymethylcarbonyl-methylamino)-2-(piperidinocarbonyl)-prop-2-yl]-benzimidazole-hydrochloride.

(8) 2-(4-amidinophenylaminomethyl)-1-methyl-5-[1-(N-carboxymethylsulphonyl-methylamino)-2-(piperidinocarbonyl)-prop-2-yl]-benzimidazole-hydrochloride.

(9) 2-(4-amidinophenylaminomethyl)-1-methyl-5-[1-(carboxymethylamino)-1-(piperidinocarbonyl)-ethyl]-benzimidazole-hydrochloride.

Yield: 81% of theory, $R_f$ value: 0.40 (Reversed phase RP 8; methanol/5% saline solution=1:1); $C_{26}H_{33}N_7O_3$ (491.60/

528.05).

mass spectrum: $(M + H)^+ = 492$
$(M - H)^- = 490$

(10) 2-(4-amidinophenylaminomethyl)-1-methyl-5-[1-(2-carboxyethylcarbonylamino)-2-(pyrrolidinocarbonyl)-prop-2-yl]-benzimidazole-hydrochloride.

(11) 2-(4-amidinophenylaminomethyl)-1-methyl-5-[1-(carboxymethylsulphonylamino))-2-(pyrrolidinocarbonyl)-prop-2-yl]-benzimidazole-hydrochloride.

(12) 2-(4-amidinophenylaminomethyl)-1-methyl-5-[1-(carboxymethylamino)-1-(diethylaminocarbonyl)-ethyl]-benzimidazole-hydrochloride.

Yield: 70% of theory, $R_f$ value: 0.50 (Reversed Phase RP 8; methanol/5% saline solution=1:1); $C_{25}H_{33}N_7O_3 \times HCl$ (479.59/516.05).

mass spectrum: $(M + H)^+ = 480$
$(M - H)^- = 478$
$(M - H + HCl)^- = 514/516$ (Cl)

(13) 2-(4-amidinophenylaminomethyl)-1-methyl-5-[1-(carboxymethylamino)-2-(pyrrolidinocarbonyl)-prop-2-yl]-benzimidazole-dihydrochloride.

Yield: % of theory, $C_{26}H_{33}N_7O_3 \times 2$ HCl (491.60/564.51); mass spectrum:

(14) 2-(4-amidinophenylaminomethyl)-1-methyl-5-[1-(carboxymethylamino)-1-(pyrrolinocarbonyl)-ethyl]-benzimidazole-dihydrochloride.

Yield: % of theory, $C_{25}H_{29}N_7O_3 \times 2$ HCl (475.55/548.46); mass spectrum:

(15) 2-(4-amidinophenylaminomethyl)-i-methyl-5-[1-(N-carboxymethyl-methylamino)-1-(pyrrolidinocarbonyl)-ethyl]-benzimidazole-dihydrochloride.

Yield: % of theory, $C_{26}H_{33}N_7O_3 \times 2$ HCl (491.60/564.51); mass spectrum:

(16) 2-(4-amidinophenylaminomethyl)-1-methyl-5-[1-(3-carboxypropylamino)-1-(pyrrolidinocarbonyl)-ethyl]-benzimidazole-dihydrochloride.

Yield: % of theory, $C_{27}H_{35}N_7O_3 \times 2$ HCl (505.63/578.54); mass spectrum:

EXAMPLE 17

2-[4-(N-phenylcarbonylamidino)-phenylaminomethyl]-1-methyl-5-[1-(ethoxycarbonylmethylamino)-1-(pyrrolidinocarbonyl)-ethyl]-benzimidazole A suspension of 1.4 g (2.4 mmol) of 2-(4-amidinophenylaminomethyl)-1-methyl-5-[1-(ethoxycarbonylmethylamino)-1-(pyrrolidinocarbonyl)-ethyl]-benzimidazole-dihydrochloride in 5 ml of N-ethyl-diisopropylamine and 2 ml dimethylformamide is combined with 1.5 g (6 mmol) of 4-nitrophenyl benzoate, whilst a clear solution is formed by heating. After 2 hours at 120° C. the solution is concentrated by evaporation in vacuo, after cooling the residue is dissolved in dichloromethane and purified on silica gel, eluting first with dichloromethane, later with dichloromethane/ethanol (50:1, 25:1, 18:1). The uniform fractions are combined, concentrated by evaporation, triturated with water, suction filtered and dried.

Yield: 0.7 g (49% of theory), $R_f$ value: 0.40 (silica gel; methylene chloride/ethanol=19:1); $C_{34}H_{39}N_7O_4$ (609.73).

mass spectrum: $(M + H)^+ = 610$
$(M + Na)^+ = 632$
$(M - H)^- = 608$

The following compounds are obtained analogously to Examples 14 and 17:

(1) 2-[4-(N-n-hexyloxycarbonylamidino)-phenylaminomethyl]-1-methyl-5-[1-(ethoxycarbonyl-methylamino)-1-(pyrrolidinocarbonyl)-ethyl]-benzimidazole.

Yield: 53% of theory, $R_f$ value: 0.35 (silica gel; methylene chloride/ethanol=9:1); $C_{34}H_{47}N_7O_5$ (633.79).

mass spectrum: $(M + Na)^+ = 656$
$(M - H)^- = 632$ (2) 2-[4-(N-n-octyloxycarbonylamidino)-phenylaminomethyl]-1-methyl-5-[1-(ethoxycarbonyl-methylamino)-1-(pyrrolidinocarbonyl)-ethyl]-benzimidazole.

Yield: 46% of theory, $R_f$ value: 0.43 (silica gel; methylene chloride/ethanol=9:1); $C_{36}H_{51}N_7O_5$ (661.84).

mass spectrum: $(M + Na)^+ = 684$
$(M - H)^- = 660$ (3) 2-[4-(N-n-hexyloxycarbonyl-amidino)-phenylaminomethyl)-1-methyl-5-[1-(methoxycarbonyl-methylamino)-1-(pyrrolidinocarbonyl)-ethyl]-benzimidazole.

(4) 2-[4-(N-n-octyloxycarbonylamidino)-phenylaminomethyl]-1-methyl-5-[1-(methoxycarbonyl-methylamino)-1-(pyrrolidinocarbonyl)ethyl]-benzimidazole.

Yield: 32% of theory, $R_f$ value: 0.27 (silica gel; methylene chloride/ethanol=9:1); $C_{35}H_{49}N_7O_5$ (647.82).

mass spectrum: $(M + Na)^+ = 670$
$(M - H)^- = 646$ (5) 2-[4-(N-n-hexyloxycarbonylamidino)-phenylaminomethyl]-1-methyl-5-[1-(N-ethoxycarbonyl-methylcarbonyl-methylamino)-2-(pyrrolidinocarbonyl)-prop-2-yl]-benzimidazole.

Yield: 52% of theory, $R_f$ value: 0.60 (silica gel; methylene chloride/ethanol=9:1); $C_{37}H_{51}N_7O_6$ (689.85).

mass spectrum: $(M + H)^+ = 690$
$(M - H)^- = 688$)
$(M + Na)^+ = 712$
$(M + HCl - H)^- = 724/726$ (Cl)

(6) 2-[4-(N-n-octyloxycarbonyl-amidino)-phenylaminomethyl)-1-methyl-5-[1-(N-ethoxycarbonylmethylcarbonyl-methylamino)-2-(pyrrolidinocarbonyl)-prop-2-yl]-benzimidazole.

(7) 2-[4-(N-n-hexyloxycarbonylamidino)-phenylaminomethyl]-1-methyl-5-[1-(N-methoxycarbonylmethylcarbonyl-methylamino)-2-(pyrrolidinocarbonyl)-prop-2-yl]-benzimidazole.

Yield: 21% of theory, $R_f$ value: 0.55 (silica gel; methylene chloride/ethanol=9:1); $C_6H_{49}N_7O_6$ (675.83).

mass spectrum: $(M+H)^+$ = 676
$(M+Na)^+$ = 698
$(M+HCl-H)^-$ = 724/26 (Cl)

(8) 2-[4-(N-n-octyloxycarbonyl-amidino)-phenylaminomethyl)-1-methyl-5-[1-(N-methoxycarbonylmethylcarbonyl-methylamino)-2-(pyrrolidinocarbonyl)-prop-2-yl]-benzimidazole.

(9) 2-[4-(N-phenylcarbonylamidino)-phenylaminomethyl]-1-methyl-5-[1-(methoxycarbonylmethylamino)-1-(pyrrolidinocarbonyl)-ethyl]-benzimidazole.

Yield: 34% of theory. $R_f$ value: 0.55 (silica gel; methylene chloride/ethanol=9:1+1% ammonia); $C_{33}H_{37}N_7O_4$ (595.70).

mass spectrum: $(M-H)^-$ = 594
$(M+Na)^+$ = 618

(10) 2-[4-(N-isopropyloxycarbonylamidino)-phenylaminomethyl]-1-methyl-5-[1-(N-ethoxycarbonylmethylcarbonyl-methylamino)-2-(pyrrolidinocarbonyl)-prop-2-yl]-benzimidazole.

Yield: 66% of theory, $R_f$ value: 0.45 (silica gel; methylene chloride/ethanol=9:1); $C_{34}H_{45}N_7O_6$ (647.77);

mass spectrum: $(M+H)^+$ = 648
$(M-H)^-$ = 646
$(M+Na)^+$ = 670

(11) 2-[4-(N-phenylcarbonylamidino)-phenylaminomethyl]-1-methyl-5-[1-(N-ethoxycarbonylmethylcarbonyl-methylamino)-2-(pyrrolidinocarbonyl)-prop-2-yl]-benzimidazole.

Yield: 23% of theory, $R_f$ value: 0.45 (silica gel; methylene chloride/ethanol 9:1) $C_{37}H_{43}N_7O_5$ (665.79).

mass spectrum: $(M+H)^+$ = 666
$(M-H)^-$ = 664
$(M+Na)^+$ = 688
$(M+H+Cl)^+$ = 700/2 (Cl)

(12) 2-[4-(N-phenylcarbonylamidino)-phenylaminomethyl]-1-methyl-5-[1-(N-methoxycarbonylmethylcarbonyl-methylamino)-2-(pyrrolidinocarbonyl)-prop-2-yl]-benzimidazole.

Yield: 67% of theory, $R_f$ value: 0.60 (silica gel; methylene chloride/ethanol=9:1); $C_{36}H_{41}N_7O_5$ (651.76).

mass spectrum: $(M+H)^+$ = 652
$(M-H)^-$ = 650
$(M+Na)^+$ = 674

(13) 2-[4-(N-n-butyloxycarbonylamidino)-phenylaminomethyl]-1-methyl-5-[1-(N-methoxycarbonylmethylcarbonyl-methylamino)-2-(pyrrolidinocarbonyl)-prop-2-yl]-benzimidazole.

Yield: 45% of theory, $R_f$ value: 0.50 (silica gel; methylene chloride/ethanol=9:1); $C_{34}H_{45}N_7O_6$ (647.77).

mass spectrum: $(M+H)^+$ = 648
$(M-H)^-$ = 646
$(M+Na)^+$ = 670
$(M-H+HCl)^-$ = 682/4 (Cl)

(14) 2-[4-(N-ethyloxycarbonylamidino)-phenylaminomethyl]-1-methyl-5-[1-(N-ethoxycarbonylmethylcarbonyl-methylamino)-2-(pyrrolidinocarbonyl)-prop-2-yl]-benzimidazole.

Yield: 54% of theory, $R_f$ value: 0.40 (silica gel; methylene chloride/ethanol=9:1); $C_{33}H_{43}N_7O_5$ (633.75).

mass spectrum: $(M+H)^+$ = 634
$(M-H)^-$ = 632
$(M+Na)^+$ = 656

(15) 2-[4-(N-ethyloxycarbonylamidino)-phenylaminomethyl]-1-methyl-5-[1-(N-methoxycarbonylmethylcarbonyl-methylamino)-2-(pyrrolidinocarbonyl)-prop-2-yl]-benzimidazole.

Yield: 53% of theory, $R_f$ value: 0.45 (silica gel; methylene chloride/ethanol=9:1); $C_{32}H_{41}N_7O_6$ (619.72).

mass spectrum: $(M+H)^+$ = 620
$(M-H)^-$ = 618
$(M+Na)^+$ = 642

(16) 2-[4-(N-pyridin-3-yl-carbonylamidino)-phenylaminomethyl]-1-methyl-5-[1-(N-ethoxycarbonylmethylcarbonyl-methylamino)-2-(pyrrolidinocarbonyl)-prop-2-yl]-benzimidazole.

Yield: 16% of theory, $R_f$ value: 0.45 (silica gel; methylene chloride/ethanol=9:1); $C_{36}H_{42}N_8O_5$ (666.78).

mass spectrum: $(M-H)^-$ = 665
$(M+Na)^+$ = 689

(17) 2-[4-(N-n-butyloxycarbonylamidino)-phenylaminomethyl]-1-methyl-5-[1-(ethoxycarbonylmethylamino)-1-(pyrrolidinocarbonyl)-ethyl]-benzimidazole.

Yield: 52% of theory, $R_f$ value: 0.42 (silica gel; methylene chloride/ethanol=9:1); $C_{32}H_{43}N_7O_5$ (605.74).

mass spectrum: $(M+H)^+ = 606$
$(M+Na)^+ = 628$
$(M-H)^- = 604$

(18) 2-[4-(N-ethyloxycarbonylamidino)-phenylaminomethyl]-1-methyl-5-[1-(ethoxycarbonylmethylamino)-1-(pyrrolidinocarbonyl)-ethyl]-benzimidazole.

Yield: 30% of theory, $R_f$ value: 0.44 (silica gel; methylene chloride/ethanol 9:1); $C_{30}H_{39}N_7O_5$ (577.68).

mass spectrum: $(M+H)^+ = 578$
$(M+Na)^+ = 600$
$(M-H)^- = 576$

(19) 2-[4-(N-benzyloxycarbonylamidino)-phenylaminomethyl]-1-methyl-5-[1-(ethoxycarbonylmethylamino)-1-(pyrrolidinocarbonyl)-ethyl]-benzimidazole.

Yield: 51% of theory, $R_f$ value: 0.50 (silica gel; methylene chloride/ethanol=9:1); $C_{35}H_{41}N_7O_5$ (639.75).

mass spectrum: $(M+Na)^+ = 662$
$(M-H)^- = 638$

(20) 2-[4-(N-pyridin-3-yl-carbonylamidino)-phenylaminomethyl]-1-methyl-5-[1-(ethoxycarbonylmethylamino)-1-(pyrrolidinocarbonyl)-ethyl]-benzimidazole.

(21) 2-[4-(N-acetoxymethyloxycarbonylamidino)-phenylaminomethyl]-1-methyl-5-[1-(ethoxycarbonylmethylamino)-1-(pyrrolidinocarbonyl)-ethyl]-benzimidazole.

Yield: 42% of theory, $R_f$ value: 0.44 (silica gel; methylene chloride/ethanol=9:1); $C_{31}H_{39}N_7O_7$ (621.09).

mass spectrum: $(M+Na)^+ = 644$
$(M-H)^- = 620$

(22) 2-[4-(N-(2,2,2-trichloroethyloxycarbonyl)-amidino)-phenylaminomethyl]-1-methyl-5-[1-(ethoxycarbonylmethylamino)-1-(pyrrolidinocarbonyl)-ethyl]-benzimidazole.

Yield: 73% of theory, $R_f$ value: 0.54 (silica gel; methylene chloride/ethanol=9:1); $C_{30}CH_{36}Cl_3N_7O_5$ (681).

mass spectrum: $M^+ = 679/81/3$ $(Cl_3)$
$(M+Na)^+ = 702/4/6$ $(Cl_3)$
$(M-H)^- = 678/80/2$ $(Cl_3)$

EXAMPLE 18

2-[4-(N-n-octyloxycarbonylamidino)-phenylaminomethyl]-1-methyl-5-[1-(carboxymethylamino)-1-(pyrrolidinocarbonyl)-ethyl]-benzimidazole A solution of 0.2 g (0.3 mmol) of 2-[4-(N-n-octyloxycarbonylamidino)-phenylaminomethyl]-1-methyl-5-[1-(ethoxycarbonylmethylamino)-1-(pyrrolidinocarbonyl)-ethyl]-benzimidazole in 3 ml tetrahydrofuran and 2.5 ml ethanol is mixed with 1.1 ml of 1N sodium hydroxide solution and stirred for 4 hours at ambient temperature. The reaction mixture is concentrated by evaporation and combined with 1 ml of 1N hydrochloric acid. After 12 hours at ambient temperature (pH 4) 2 drops of ammonia (33%) are added, whereupon a bright yellow precipitate is formed. After the solid formed has been suction filtered the filtrate is combined with 1 ml of 1 N hydrochloric acid and concentrated by evaporation with the addition of toluene. The residue is triturated with acetone, suction filtered, washed with diethylether and dried.

Yield: 0.1 g (50% of theory), $R_f$ value: 0.35 (Reversed phase RP 8; methanol/5% saline solution=2:1); $C_{34}H_{47}N_7O_5$ (633.79).

mass spectrum: $(M+H)^+ = 634$
$(M+H+Na)^{++} = 328.5$

EXAMPLE 19

2-[4-(N-hydroxyamidino)-phenylaminomethyl]-1-methyl-5-[1-(ethoxycarbonylmethylamino)-1-(pyrrolidinocarbonyl)-ethyl]-benzimidazole.

A suspension of 0.6 g (1.2 mmol) of 2-(4-cyanophenylaminomethyl)-1-methyl-5-[1-(ethoxycarbonylmethylamino)-1-(pyrrolidinocarbonyl)-ethyl]-benzimidazole in 50 ml ethanol is mixed with 0.47 g (7.8 mmol) of hydroxylamine hydrochloride and 0.35 g (3.5 mmol) of sodium carbonate and refluxed for 17 hours. After cooling, the residue is filtered off, the filtrate is concentrated by evaporation and taken up in water. After extracting twice with dichloromethane, the combined organic phases are dried and concentrated by evaporation. The crude product is purified on silica gel, eluting with dichloromethane/ethanol (19/1 and 7/1). The uniform fractions are combined, concentrated by evaporation, triturated with diisopropylether and dried.

Yield: 0.025 g (4% of theory), $R_f$ value: 0.68 (silica gel; methylene chloride/ethanol=4:1); $C_{27}H_{35}N_7O_4$ (521.62).

mass spectrum: $(M-H)^- = 520$
$(M+Na)^+ = 544$

EXAMPLE 20

2-[4-(N-phenylcarbonylamidino)-phenylaminomethyl]-1-methyl-5-[1-(isopropyloxycarbonylmethylamino)-1-(pyrrolidinocarbonyl)-ethyl]-benzimidazole.

a. Ethyl 4-(5-methyl-1,2,4-oxadiazol-3-yl)-phenylamino-acetate

Prepared analogously to Example 9a from 4-(5-methyl-1,2,4-oxadiazol-3-yl)-aniline and ethyl bromoacetate in N-ethyl-diisopropylamine.

Yield: 78% of theory, $R_f$ value: 0.60 (silica gel; ethyl acetate/petroleum ether=1:1).

b. 4-(5-methyl-1,2,4-oxadiazol-3-yl)-phenylamino-acetic Acid

Prepared analogously to Example 4 from ethyl 4-(5-methyl-1,2,4-oxadiazol-3-yl)-phenylamino-acetate and sodium hydroxide solution in ethanol.

Yield: 75% of theory, R$_f$ value: 0.15 (silica gel; methylene chloride/ethanol=9:1).

c. 2-[4-(5-methyl-1,2,4-oxadiazol-3-yl)-phenylaminomethyl]-1-methyl-5-[1-amino-(pyrrolidin-1-yl-carbonyl)-ethyl]-benzimidazole Prepared analogously to Example 1e/f from 2-(4-methylamino-3-amino-phenyl)-2-tert.butyloxycarbonyl-amino-1-pyrrolidin-1-yl-propanone, 4-(5-methyl-1,2,4-oxadiazol-3-yl)-phenylamino-acetic acid and carbonyldiimidazole in tetrahydrofuran and subsequent treatment with glacial acetic acid.

Yield: 34% of theory, R$_f$ value: 0.10 (silica gel; methylene chloride/ethanol=9:1).

d. 2-[4-(5-methyl-1,2,4-oxadiazol-3-yl)-phenylaminomethyl]-1-methyl-5-[1-(isopropyloxycarbonylmethylamino)-1-(pyrrolidinocarbonyl)-ethyl]-benzimidazole Prepared analogously to Example 11 from 2-[4-(5-methyl-1,2,4-oxadiazol-3-yl)-phenylaminomethyl]-1-methyl-5-[1-amino-1-(pyrrolidinocarbonyl)-ethyl]-benzimidazole, isopropyl bromoacetate and potassium carbonate in isopropanol/methylene chloride.

Yield: 42% of theory, R$_f$ value: 0.60 (silica gel; methylene chloride/ethanol=9:1).

e. 2-(4-amidinophenylaminomethyl)-1-methyl-5-[1-(isopropyloxycarbonylmethylamino)-1-(pyrrolidinocarbonyl)-ethyl]-benzimidazole-acetate Prepared analogously to Example 1d from 2-[4-(5-methyl-1,2,4-oxadiazol-3-yl)-phenylaminomethyl]-1-methyl-5-[1-(isopropyloxycarbonylmethylamino)-1-(pyrrolidinocarbonyl)-ethyl]-benzimidazole and hydrogen/palladium (10% on activated charcoal) in ethanol/glacial acetic acid.

Yield: 69% of theory, R$_f$ value: 0.30 (silica gel; methylene chloride/ethanol=7:3).

f. 2-[4-(N-phenylcarbonylamidino)-phenylaminomethyl]-1-methyl-5-[1-(isopropyloxycarbonylmethylamino)-1-(pyrrolidinocarbonyl)-ethyl]-benzimidazole Prepared analogously to Example 17 from 2-(4-amidinophenylaminomethyl)-1-methyl-5-[1-(isopropyloxycarbonylmethylamino)-1-(pyrrolidinocarbonyl)-ethyl]-benzimidazole-acetate and 4-nitrophenyl benzoate in N-ethyl-diisopropylamine/dimethylformamide.

Yield: 26% of theory, R$_f$ value: 0.50 (silica gel; methylene chloride/ethanol=9:1); C$_{35}$H$_{41}$N$_7$O$_4$ (623.75).

mass spectrum: (M+Na)$^+$ = 646
(M−H)$^−$ = 622

The following compounds are prepared analogously to Example 20:

(1) 2-[4-(N-phenylcarbonylamidino)-phenylaminomethyl]-1-methyl-5-[1-(n-butyloxycarbonylmethylamino)-1-(pyrrolidinocarbonyl)-ethyl]-benzimidazole.

(2) 2-[4-(N-phenylcarbonylamidino)-phenylaminomethyl]-1-methyl-5-[1-(2-phenylethyloxycarbonylmethylamino)-1-(pyrrolidinocarbonyl)-ethyl]-benzimidazole.

(3) 2-[4-(N-n-hexyloxycarbonylamidino)-phenylaminomethyl]-1-methyl-5-[1-(isopropyloxycarbonylmethylamino)-1-(pyrrolidinocarbonyl)-ethyl]-benzimidazole.

Yield: 40% of theory, R$_f$ value: 0.45 (silica gel; methylene chloride/ethanol=9:1); C$_{35}$H$_{49}$N$_7$O$_5$ (647.82).

mass spectrum: (M+H)$^+$ = 648
(M−H)$^−$ = 646
(M+Na)$^+$ = 670

(4) 2-[4-(N-n-octyloxycarbonylamidino)-phenylaminomethyl]-1-methyl-5-[1-(isopropyloxycarbonylmethylamino)-1-(pyrrolidinocarbonyl)-ethyl]-benzimidazole Yield: 31% of theory, R$_f$ value: 0.48 (silica gel; methylene chloride/ethanol=9:1); C$_{37}$H$_{53}$N$_7$O$_5$ (675.88).

mass spectrum: (M+H)$^+$ = 674
(M+Na)$^+$ = 698

(5) 2-[4-(N-(2,2,2-trichloroethyloxycarbonyl)-amidino)-phenylaminomethyl]-1-methyl-5-[1-(isopropyloxycarbonylmethylamino)-1-(pyrrolidinocarbonyl)-ethyl]-benzimidazole Yield: 43% of theory, R$_f$ value: 0.50 (silica gel; methylene chloride/ethanol=9:1); C$_{31}$H$_{38}$Cl$_3$N$_7$O$_5$ (695.05); mass spectrum: (M−H)$^−$=692/694/696/698 (Cl$_3$).

(6) 2-[4-(N-phenylcarbonylamidino)-phenylaminomethyl]-1-methyl-5-[1-(n-propyloxycarbonylmethylamino)-1-(pyrrolidinocarbonyl)-ethyl]-benzimidazole.

Yield: % of theory, R$_f$ value: (silica gel; methylene chloride/ethanol=9:1); C$_{35}$H$_{41}$N$_7$O$_4$ (623.76).

mass spectrum: (M+H)$^+$ =
(M+Na)$^+$ =

(7) 2-[4-(N-n-octyloxycarbonylamidino)-phenylaminomethyl]-1-methyl-5-[1-(n-propyloxycarbonylmethylamino)-1-(pyrrolidinocarbonyl)-ethyl]-benzimidazole.

Yield: % of theory, R$_f$ value: (silica gel; methylene chloride/ethanol=9:1); C$_{37}$H$_{53}$N$_7$O$_5$ (675.88).

mass spectrum: (M+H)$^+$ =
(M+Na)$^+$ =

EXAMPLE 21

(R)-2-(4-amidinophenylaminomethyl)-1-methyl-5-[1-(carboxymethylamino)-1-(pyrrolidinocarbonyl)-ethyl]-benzimidazole-hydrochloride.

a. Ethyl 2-amino-2-(4-chloro-3-nitro-phenyl)-propionate

A mixture of 28 g (0.11 mol) of 2-amino-2-(4-chloro-3-nitro-phenyl)-propionic acid in 200 ml of 5.6N ethanolic hydrochloric acid is refluxed for 36 hours. After evaporation of the solvent the residue is suspended in 300 ml of ethyl acetate and mixed with 300 ml of saturated sodium hydrogen carbonate solution. The organic phase is washed twice with saturated sodium hydrogen carbonate solution and once with water. The obtained organic phase is dried over sodium sulphate and evaporated.

Yield: 21.1 g (68% of theory) light brown oil.

b. Ethyl (R)-(+)-2-amino-2-(4-chloro-3-nitro-phenyl)-propionate 17.33 g (63.6 mmol) of ethyl 2-amino-2-(4-chloro-3-nitro-phenyl)-propionate are dissolved in 247 ml of isopropanol und 207 ml of methanol and mixed with 9.54 g (63.6 mMol) of L-(+)-tartaric acid. The reaction mixture is heated up to 100° C., whereby a clear solution is obtained. The solution is cooled within 3 hours up to 27° C. and the obtained precipitate is suction filtered, washed with ethanol and dried. The formed precipitate (21.5 g) is suspended in 400 ml of ethyl acetate and mixed with 400 ml of saturated sodium hydrogen carbonate solution. After extraction and separation of the phases the organic phase is washed with water, dried and evaporated.

Yield: 7.68 g (44.4% of theory) light yellow oil, $[\alpha]^{20}$=+4.38° (ethyl acetate); HPLC-analysis: ee value >98.6%.

c. (R)-(−)-2-amino-2-(4-chloro-3-nitro-phenyl)-propionic Acid

Prepared analogously to Example 4 from ethyl (R)-(+)-2-amino-2-(4-chloro-3-nitro-phenyl)-propionate and sodium hydroxide solution in tetrahydrofurane.

Yield: 63% of theory, $[\alpha]^{20}$=−59.6° (methanol/water=1:1).

d. (R)-2-tert.butyloxycarbonylamino-2-(4-chloro-3-nitro-phenyl)-propionic Acid

Prepared analogously to Example 5d from (R)-(−)-2-amino-2-(4-chloro-3-nitro-phenyl)-propionic acid and di-tert.butyl pyrocarbonate and triethylamine in dioxane.

Yield: 100% of theory, e. (R)-2-tert.butyloxycarbonylamino-2-(4-methylamino-3-nitro-phenyl)-propionic Acid Prepared analogously to Example 1b from (R)-2-tert.butyloxycarbonylamino-2-(4-chloro-3-nitro-phenyl)-propionic acid and methylamine.

Yield: 69i of theory.

f. (R)-2-(4-methylamino-3-nitro-phenyl)-2-tert.butyloxycarbonylamino-1-prrolidino-propanone Prepared analogously to Example 1c from (R)-2-tert.butyloxycarbonylamino-2-(4-methylamino-3-nitro-phenyl)-propionic acid, pyrrolidine and carbonyl diimidazole in tetrahydrofurane.

Yield: 96% of theory.

g. (R)-2-(4-methylamino-3-amino-phenyl)-2-tert.butyloxycarbonylamino-1-pvrrolidino-propanone Prepared analogously to Example 1c from (R)-2-(4-methylamino-3-nitro-phenyl)-2-tert.butyloxycarbonylamino-1-pyrrolidino-propanone and hydrogen/palladium on charcoal in methanol.

Yield: 99% of theory.

h. (R)-2-(4-cyanophenylaminomethyl)-1-methyl-5-[1-(N-tert.butyloxycarbonylamino)-1-(pyrrolidinocarbonyl)-ethyl]-benzimidazole Prepared analogously to Example 1c/1f from (R)-2-(4-methylamino-3-amino-phenyl)-2-tert.butyloxycarbonylamino-1-pyrrolidino-propanone, 4-cyano-phenylglycine, carbonyl diimidazole in tetrahydrofurane and subsequent cyclisation in glacial acetic acid.

Yield: 100% of theory.

i. (R)-2-(4-cyanophenylaminomethyl)-1-methyl-5-[1-amino-1-(pyrrolidinocarbonyl)-ethyl]-benzimidazole Prepared analogously to Example 6i from (R)-2-(4-cyanophenylaminomethyl)-1-methyl-5-[1-(N-tert.butyloxycarbonylamino)-1-(pyrrolidinocarbonyl)-ethyl]-benzimidazole and 6N hydrochloric acid in dioxane.

Yield: 76% of theory.

k. (R)-2-(cyanophenylaminomethyl)-1-methyl-5-[1-(ethoxycarbonylmethylamino)-1-(pyrrolidinocarbonyl)-ethyl]-benzimidazole Prepared analogously to Example 6k from (R)-2-(4-cyanophenylaminomethyl)-1-methyl-5-[1-amino-1-(pyrrolidinocarbonyl)-ethyl]-benzimidazole and ethyl jodoacetate/potassium carbonate in acetone.

Yield: 75% of theory.

l. (R)-2-(4-amidinophenylaminomethyl)-1-methyl-5-[1-(ethoxycarbonylmethylamino)-1-(pyrrolidinocarbonyl)-ethyl]-benzimidazole-hydrochloride.

Prepared analogously to Example 1g from (R)-2-(4-cyanophenylaminomethyl)-1-methyl-5-[1-(ethoxycarbonylmethylamino)-1-(pyrrolidinocarbonyl)-ethyl]-benzimidazole and hydrochloric acid/ammonium carbonate in ethanol.

Yield: 95% of theory.

m. (R)-2-(4-amidinophe:nylaminomethyl)-1-methyl-5-[1-(carboxymethylamino)-1-(pyrrolidinocarbonyl)-ethyl]-benzimidazole-hydrochlorid Prepared analogously to Example 4 from (R)-2-(4-amidinophenylaminomethyl)-1-methyl-5-[1-(ethoxycarbonylmethylamino)-1-(pyrrolidinocarbonyl)-ethyl]-benzimidazole and sodium hydroxide solution in ethanol.

Yield: 100% of theory. $C_{25}H_{31}N_7O_3 \times 2HCl$ (477.57/550.5);

mass spectrum: $(M+H)^+$ = 478
$(M-H+HCl)^-$ = 512/514 (Cl)
$(M-H+2HCl)^-$ = 448/550/552 (Cl$_2$)

EXAMPLE 22

Dry Ampoule Containing 75 mg of Active Substance Per 10 ml

Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

EXAMPLE 23

Dry Ampoule Containing 35 mg of Active Substance Per 2 ml

Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 24

Tablet Containing 50 mg of Active Substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE 25

Tablet Containing 350 mg of Active Substance

Preparation:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 26

Capsules Containing 50 mg of Active Substance

Composition:

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatin capsules in a capsule filling machine.

EXAMPLE 27

Capsules Containing 350 mg of Active Substance

Composition:

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatin capsules in a capsule filling machine.

EXAMPLE 27

Suppositories Containing 100 mg of Active Substance

| 1 suppository contains: | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Method:

The polyethyleneglycol is melted together with polyethylene sorbitan monostearate. At 40° C. the ground active substance is homogeneously dispersed in the melt. It is cooled to 38° C. and poured into slightly chilled suppository moulds.

What is claimed is:

1. A compound of the formula (I)

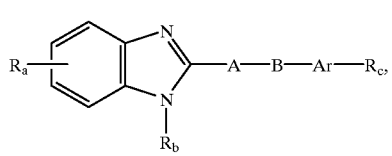

wherein

Ar is a phenylene or naphthylene group optionally substituted by a fluorine, chlorine, or bromine atom or by a trifloromethyl, $C_{1-3}$-alkyl, or $C_{1-3}$-alkoxy group, a thienylene, thiazolylene, pyridinylene, pyrimidinylene, pyrazinylene, or pyridazinylene group optionally substituted in the carbon skeleton by a $C_{1-3}$-alkyl group;

A is a $C_{1-3}$-alkylene group;

B is an oxygen or sulfur atom, or a methylene, carbonyl, sulfinyl, or sulfonyl group, or an imino group optionally substituted by a $C_{1-3}$-alkyl group wherein the alkyl moiety may be mono- or disubstituted by a carboxy group;

$R_a$ is an $R_1$-CO-$C_{3-5}$-cycloalkyl group, wherein
  $R_1$ is a $C_{1-3}$-alkoxy, amino, $C_{1-4}$-alkylamino, or di-($C_{1-4}$-alkyl)-amino group wherein each alkyl moiety may be substituted by a carboxy group,
  a 4- to 7-membered cycloalkyleneimino or cycloalkenyleneimino group which may be substituted by a hydroxy group or by one or two $C_{1-3}$-alkyl groups, wherein an alkyl substituent may simultaneously be substituted by a hydroxy, $C_{1-3}$-alkoxy, carboxy, carboxy-$C_{1-3}$-alkoxy, carboxy-$C_{1-3}$-alkylamino, N-($C_{1-3}$-alkyl)-N-(carboxy-$C_{1-3}$-alkyl)-amino, carboxy-$C_{1-3}$-alkylaminocarbonyl, N-($C_{1-3}$-alkyl)-N-(carboxy-$C_{1-3}$-alkyl)-aminocarbonyl, carboxy-$C_{1-3}$-alkylaminocarbonylamino, 1-($C_{1-3}$-alkyl)-3-(carboxy-$C_{1-3}$-alkyl)-aminocarbonylamino, 3-($C_{1-3}$-alkyl)-3-(carboxy-$C_{1-3}$-alkyl)-aminocarbonylamino, or 1,3-di-($C_{1-3}$-alkyl)-3-(carboxy-$C_{1-3}$-alkyl)-aminocarbonylamino,
  a 4- to 7-membered cycloalkenyleneimino group substituted by a hydroxy group,
  a 5- to 7-membered cycloalkyleneimino group to which a phenyl ring is fused via two adjacent carbon atoms, wherein the cycloalkyleneimino moiety is optionally substituted by a $C_{1-3}$-alkyl group,
  a morpholino, piperazino, N-($C_{1-3}$-alkyl)-piperazino, pyrrolino, 3,4-dehydropiperidino, or pyrrol-1-yl group,
an $R_2$-CX-$C_{3-5}$-cycloalkyl group, wherein
  $R_2$ is a phenyl, naphthyl or monocyclic 5- or 6-membered heteroaryl group optionally substituted by a $C_{1-3}$-alkyl group, wherein the 6-membered heteroaryl group contains one, two, or three nitrogen atoms and the 5-membered heteroaryl group contains an imino group optionally substituted by a $C_{1-3}$-alkyl group, an oxygen or sulfur atom, or an imino group optionally substituted by a $C_{1-3}$-alkyl group and an oxygen or sulfur atom or one or two nitrogen atoms and the abovementioned alkyl substituent may be substituted by a carboxy, carboxy-$C_{1-3}$-alkoxy, carboxy-$C_{1-3}$-alkylamino, or N-($C_{1-3}$-alkyl)-carboxy-$C_{1-3}$-alkylamino group, and
  X is an oxygen atom, a $C_{1-3}$-alkylimino, $C_{1-3}$-alkoxyimino, $C_{1-3}$-alkylhydrazino, di-($C_{1-3}$-alkyl)-hydrazino, $C_{2-4}$-alkanoylhydrazino, N-($C_{1-3}$-alkyl)-$C_{2-4}$-alkanoylhydrazino or $C_{1-3}$-alkylidene group each of which may be substituted in the alkyl or alkanoyl moiety or in the alkyl and alkanoyl moieties by a carboxy group,
a $C_{1-3}$-alkyl or $C_{3-5}$-cycloalkyl group substituted by an imidazole or irnidazolone group, wherein
  the imidazole ring may be substituted by a phenyl or carboxy group and by one or two $C_{1-3}$-alkyl groups or by one, two, or three $C_{1-3}$-alkyl groups, wherein the substituents may be identical or different and one of the abovementioned alkyl substituents may simultaneously be substituted by a carboxy group or may be substituted in the 2 or 3 position by an amino, $C_{2-4}$-alkanoylamino, $C_{1-3}$-alkylamino, N-($C_{2-4}$-alkanoyl)-$C_{1-3}$-alkylamino or di-($C_{1-3}$-alkyl)-amino group, and the imidazolone ring may be substituted by a $C_{1-3}$-alkyl group, wherein the alkyl substituent may be substituted by a carboxy group or in the 2 or 3 position by an
  amino, $C_{2-4}$-alkanoylamino, $C_{1-3}$-alkylamino, N-($C_{2-4}$-alkanoyl)-$C_{1-3}$-alkylamino, or di-($C_{1-3}$-alkyl)-amino group, and
  additionally a phenyl or pyridine ring may be fused to the abovementioned imidazole or imidazolone rings via two adjacent carbon atoms,
an imidazolidine-2,4-dion-5-yl group which may be substituted by one or two $C_{1-3}$-alkyl groups, wherein at the same time an alkyl substituent may be substituted by a carboxy group,
a $C_{1-4}$-alkyl group which is substituted
by a $C_{1-3}$-alkyl-$Y_1$-$C_{1-3}$-alkyl, HOOC-$C_{1-3}$-alkyl-$Y_1$-$C_{1-3}$-alkyl, tetrazolyl-$C_{1-3}$-alkyl-$Y_2$, $R_3NR_4$—, or $R_3NR_4$-$C_{1-3}$-alkyl group, and
by an isoxazolidinylcarbonyl group optionally substituted by a $C_{1-3}$-alkyl group, by a pyrrolino-carbonyl, 3,4-dehydro-piperidinocarbonyl, pyrrol-1-yl-carbonyl, carboxy, aminocarbonyl, $C_{1-3}$-alkylaminocarbonyl, di-($C_{1-3}$-alkyl)-aminocarbonyl, or 4- to 7-membere,d cycloalkyleneiminocarbonyl group, wherein in the abovementioned groups; the cycloalkyleneimino moiety may be substituted by one or two $C_{1-3}$-alkyl groups and at the same time each alkyl moiety or alkyl substituent in the abovementioned $C_{1-3}$-alkylaminocarbonyl, di-($C_{1-3}$-alkyl)-aminocarbonyl, or cycloalkyleneiminocarbonyl groups may be substituted by a carboxy group, and the remaining hydrogen atoms of the $C_{1-4}$-alkyl group may be wholly or partially replaced by fluorine atoms, wherein
  $R_3$ is a hydrogen atom or a $C_{1-3}$-alkyl group optionally substituted by a carboxy group, and
  $R_4$ is a hydrogen atom, a $C_{1-3}$-alkyl-$Y_1$-$C_{1-3}$-alkyl-$Y_2$, carboxy-$C_{1-3}$-alkyl-$Y_1$-$C_{1-3}$-alkyl-$Y_2$, $C_{1-3}$-alkyl-$Y_2$, or carboxy-$C_{1-3}$-alkyl-$Y_2$ group, or
  $R_3$ and $R_4$ together with the nitrogen atom between them are an 4- to 7-membered cycloalkyleneimino group optionally substituted by a carboxy, $C_{1-3}$-alkyl, or carboxy-$C_{1-3}$-alkyl group, wherein
    $Y_1$ is a carbon-carbon bond, an oxygen or sulfur atom, or a sulfinyl, sulfonyl, —NH—, —NH—CO—, or —NH—CO—NH— group, and
    $Y_2$ is a carbon—nitrogen bond or a carbonyl, sulfonyl, imino, or —NH—CO— group, wherein the carbonyl group of the —NH—CO— group is linked to the nitrogen atom of the $R_3NR_4$— group, and the imino groups occurring in the definition of the groups $Y_1$ and $Y_2$ may each additionally be substituted by a $C_{1-3}$-alkyl or carboxy-$C_{1-3}$-alkyl group,
a $C_{1-3}$-alkyl or $C_{3-5}$-cycloalkyl group substituted by a $R_5NR_6$— group, wherein
  $R_5$ is a hydrogen atom, a $C_{1-3}$-alkyl, $C_{5-7}$-cycloalkyl, phenylcarbonyl, phenylsulfonyl, or pyridinyl group, and
  $R_6$ is a $C_{1-3}$-alkyl, carboxy-$C_{1-3}$-alkyl, or carboxy-$C_{1-3}$-alkylcarbonyl group,
a $C_{1-3}$-alkyl group which is substituted by a $C_{2-4}$-alkanoyl or $C_{5-7}$-cycloalkanoyl group and by a $C_{1-3}$-alkyl group substituted by a chlorine, brouiine, or iodine atom;
$R_b$ is a hydrogen atom or a $C_{1-3}$-alkyl group; and
$R_c$ is a cyano group or an amidino group optionally substituted by one or two $C_{1-3}$-alkyl groups, wherein the carboxy, amino and imino groups mentioned in the definition of the abovementioned groups may also be substituted by a group which can be cleaved in vivo, or a tautomer thereof, or a compound thereof which contains, instead of a carboxy group, a group which is negatively charged under physiological conditions, or a salt thereof.

2. A compound of the formula (Ia)

$$R_a \text{—} \underset{R_b}{\text{[benzimidazole]}} \text{—} 2 \text{—} A \text{—} B \text{—} \text{[phenyl]} \text{—} R_c,$$

(Ia)

wherein

A is a $C_{1-3}$-alkylene group;

B is an oxygen or sulfur atom, or a methylene, carbonyl, sulfinyl, or sulfonyl group, or an imino group optionally substituted by a $C_{1-3}$-alkyl group wherein the alkyl moiety may be mono- or disubstituted by a carboxy group;

$R_a$ is an $R_1$-CO—$C_{3-5}$-cycloalkyl group, wherein $R_1$ is a $C_{1-3}$-alkoxy, amino, $C_{1-4}$-alkylamino, or di-($C_{1-4}$-alkyl)-amino group wherein each alkyl moiety may be substituted by a carboxy group, a 4- to 7-membered cycloalkyleneimino or cycloalkenyleneimino group which may be substituted by one or two $C_{1-3}$-alkyl groups, wherein an alkyl substituent may simultaneously be substituted by a hydroxy, $C_{1-3}$-alkoxy, carboxy, carboxy-$C_{1-3}$-alkoxy, carboxy-$C_{1-3}$-alkylamino, N-($C_{1-3}$-alkyl)-N-(carboxy-$C_{1-3}$-alkyl)-amino, carboxy-$C_{1-3}$-alkylaminocarbonyl, N-($C_{1-3}$-alkyl1)-N -(carboxy-$C_{1-3}$-alkyl)-aminocarbonyl, carboxy,-$C_{1-3}$-alkylaminocarbonylamino, 1-($C_{1-3}$-alkyl)-3-(carboxy-$C_{1-3}$-alkyl)-aminocarbonylamino, 3-($C_{1-3}$-alkyl)-3-(carboxy-$C_{1-3}$-alkyl)-aminocarbonylamino, or 1,3-di-($C_{1-3}$-alkyl)-3-(carboxy-$C_{1-3}$-alkyl)-aminocarbonylamino group, a 4- to 7-metnbered cycloalkenyleneimino group substituted by a hydroxy group, a 5- to 7-membered cycloalkyleneimino group to which a phenyl ring is fused via two adjacent carbon atoms, wherein the cycloalkyleneimino moiety is optionally substituted by a $C_{1-3}$-alkyl group, a morpholino, piperazino, N-($C_{1-3}$-alkyl)-piperazino, pyrrolino, 3,4-dehydropiperidino, or pyrrol-1-yl group, an $R_2$-CX-$C_{3-5}$-cycloalkyl group, wherein $R_2$ is a phenyl, naphthyl, or monocyclic 5- or 6-membered heteroaryl group optionally substituted by a $C_{1-3}$-alkyl group, wherein the 6-membered heteroaryl group contains one, two, or three nitrogen atoms and the 5-membered heteroaryl group contains an imino group optionally substituted by a $C_{1-3}$-alkyl group, an oxygen or sulfur atom, or an imino group optionally substituted by a $C_{1-3}$-alkyl group and an oxygen or sulfur atom or one or two nitrogen atoms and the abovementioned alkyl substituent may be substituted by a carboxy, carboxy-$C_{1-3}$-alkoxy, carboxy-$C_{1-3}$-alkylamino, or N-($C_{1-3}$-alkyl)-carboxy-$C_{1-3}$-alkylamino group, and X is an oxygen atom, a $C_{1-3}$-alkylimino, $C_{1-3}$-alkoxyimino, $C_{1-3}$-alkylhydrazino, di-($C_{1-3}$-alkyl)-hydrazino, $C_{2-4}$-alkanoylhydrazino, N-($C_{1-3}$-alkyl)-$C_{2-4}$-alkanoylhydrazino, or $C_{1-3}$-alkylidene group each of which may be substituted in the alkyl or alkanoyl moiety or in the alkyl and alkanoyl moieties by a carboxy group, a $C_{1-3}$-alkyl or $C_{3-5}$-cycloalkyl group substituted by an imidazole or imidazolone group wherein the imidazole ring may be substituted by a phenyl or carboxy group and by one or two $C_{1-3}$-alkyl groups or by one, two, or three $C_{1-3}$-alkyl groups, wherein the substituents may be identical or different and one of the abovementioned alkyl substituents may simultaneously be substituted by a carboxy group or may be substituted in the 2 or 3 position by an amino, $C_{2-4}$-alkanoylamino, $C_{1-3}$-alkylamino, N-($C_{2-4}$-alkanoyl)-$C_{1-3}$-alkylamino, or di-($C_{1-3}$-alkyl)-amino group, and the imidazolone ring may be substituted by a $C_{1-3}$-alkyl group, wherein the alkyl substituent may be substituted by a carboxy group or in the 2 or 3 position by an amino, $C_{2-4}$-alkanoylamino, $C_{1-3}$-alkylamino, N-($C_{2-4}$-alkanoyl)-$C_{1-3}$-alkylamino, or di-($C_{1-3}$-alkyl)-amino group, and additionally a phenyl or pyridine ring may be fused to the abovementioned imidazole or imidazolone rings via two adjacent carbon atoms, an imidazolidine-2,4-dion-5-yl group which may be substituted by one or two $C_{1-3}$-alkyl groups, wherein at the same time an alkyl substituent may be substituted by a carboxy group, a $C_{1-4}$-alkyl group which is substituted by a $C_{1-3}$-alkyl-$Y_1$-$C_{1-3}$-alkyl, HOOC-$C_{1-3}$-alkyl-$Y_1$-$C_{1-3}$-alkyl, tetrazolyl-$C_{1-3}$-alkyl-$Y_2$, $R_3NR_4$—, or $R_3NR_4$-$C_{1-3}$-alkyl group and by an isoxazolidinylcarbonyl group optionally substituted by a $C_{1-3}$-alkyl group, by a pyrrolinocarbonyl, 3,4-dehydro-piperidinocarbonyl, pyrrol-1-yl-carbonyl, carboxy, aminocarbonyl, $C_{1-3}$-alkylaminocarbonyl, di-($C_{1-3}$-alkyl)-aminocarbonyl, or 4- to 7-membered cycloalkyleneiminocarbonyl group, wherein in the abovementioned groups the cycloalkyleneimino moiety may be substituted by one or two $C_{1-3}$-alkyl groups and at the same time each alkyl moiety or alkyl substituent in the abovementioned $C_{1-3}$-alkylaminocarbonyl, di-($C_{1-3}$-alkyl)-aminocarbonyl or cycloalkyleneiminocarbonyl groups may be substituted by a carboxy group, and the remaining hydrogen atoms of the $C_{1-4}$-alkyl group may be wholly or partially replaced by fluorine atoms, wherein $R_3$ is a hydrogen atom or a $C_{1-3}$-alkyl group optionally substituted by a carboxy group, and $R_4$ is a hydrogen atom, a $C_{1-3}$-alkyl-$Y_1$-$C_{1-3}$-alkyl-$Y_2$, carboxy-$C_{1-3}$-alkyl-$Y_1$-$C_{1-3}$-alkyl-$Y_2$, $C_{1-3}$-alkyl-$Y_2$. or carboxy-$C_{1-3}$-alkyl-$Y_2$ group or $R_3$ and $R_4$ together with the nitrogen atom between them are an 4- to 7-membered cycloalkyleneimino group optionally substituted by a carboxy, $C_{1-3}$-alkyl, or carboxy-$C_{1-3}$-alkyl group, wherein $Y_1$ is a carbon-carbon bond, an oxygen or sulfur atom, or a sulfinyl, sulfonyl, —NH—, —NH—CO—, or —NH—CO—NH— group, and $Y_2$ is a carbon—nitrogen bond or a carbonyl, sulfonyl, imino, or —NH—CO— group, wherein the carbonyl group of the —NH—CO— group is linked to the nitrogen atom of the $R_3NR_4$— group, and the imino groups occurring in the definition of the groups $Y_1$ and $Y_2$ may each additionally be substituted by a $C_{1-3}$-alkyl or carboxy-$C_{1-3}$-alkyl group, a $C_{1-3}$-alkyl or $C_{3-5}$-cycloalkyl group substituted by a $R_5NR_6$— group, wherein $R_5$ is a hydrogen atom, a $C_{1-3}$-alkyl, $C_{5-7}$-cycloalkyl, phenylcarbonyl, phenylsulfonyl or pyridinyl group, and $R_6$ is a $C_{1-3}$-alkyl, carboxy-$C_{1-3}$-alkyl, or carboxy-$C_{1-3}$-alkylcarbonyl group, a $C_{1-3}$-alkyl group which is substituted by a $C_{2-4}$-alkanoyl or $C_{5-7}$-cycloalkanoyl group and by a $C_{1-3}$-alkyl group substituted by a chlorine, bromine, or iodine atom;

$R_b$ is a hydrogen atom or a $C_{1-3}$-alkyl group; and $R_c$ is a cyano group or an amidino group which may be substituted by a hydroxy group, by one or two $C_{1-3}$-alkyl groups, or by one or two $C_{1-8}$-alkoxycarbonyl groups, wherein the carboxy, amino and imino groups mentioned in the definition of the abovementioned groups may also be substituted by a group which can be cleaved in vivo, or a tautomer or salt thereof.

3. The compound of the formula Ia according to claim 2, wherein

A is a $C_{1-3}$-alkylene group,

B is an oxygen atom, a methylene, imino, or N-($C_{1-3}$-alkyl)-imino group wherein the alkyl moiety may be substituted by a carboxy group, $R_a$ is an $C_{3-5}$-cycloalkyl group substituted by the $R_1$-CO group in the 1 position wherein $R_1$ is a $C_{1-3}$-alkoxy, amino, $C_{1-4}$-alkylamino, or di-($C_{1-4}$-alkyl)-amino group wherein each alkyl moiety may be substituted by a carboxy group, a 4- to 7-membered cycloalkyleneimino group which may be substituted by a hydroxy group or by one or two, $C_{1-3}$-alkyl groups, wherein an alkyl substituent may simultaneously be substituted by a hydroxy, $C_{1-3}$-alkoxy, carboxy, carboxy-$C_{1-3}$-alkoxy, carboxy-$C_{1-3}$-alkylamino, N-($C_{1-3}$-alky)-N-(carboxy-$C_{1-3}$-alkyl)-amino, carboxy-$C_{1-3}$-alkylaminocarbonyl, N-($C_{1-3}$-alkyl)-N-(carboxy-$C_{1-3}$-alkyl)-aminocarbonyl, carboxy-$C_{1-3}$-alkyl-aminocarbonylamino, 1-($C_{1-3}$-alkyl)-3-(carboxy-$C_{1-3}$-alkyl)-aminocarbonylamino, 3-($C_{1-3}$-alkyl)-3-(carboxy-$C_{1-3}$-alkyl)-aminocarbonylamino, or 1,3-di-($C_{1-3}$-alkyl)-3-(carboxy-$C_{1-3}$-alkyl)-aminocarbonylamino group, a 5- to 7-membered cycloalkyleneimino group to which a phenyl ring is fused via two adjacent carbon atoms, wherein the cycloalkyleneiemino moiety is optionally substituted by a $C_{1-3}$-alkyl group, a morpholino, piperazino, N-($C_{1-3}$-alkyl)-piperazino, pyrrolino, 3,4-dehydropiperidino, or pyrrol-1-yl group, a $C_{3-5}$-cycloalkyl group substituted in the 1 position by the $R_2$-CX— group, wherein $R_2$ is a phenyl, naphtllyl, or monocyclic 5- or 6-membered heteroaryl group optionally substituted by a $C_{1-3}$-alkyl group, wherein the 6-membered heteroaryl group contains one, two, or three nitrogen atoms and the 5-membered heteroaryl group contains an imirno group optionally substituted by a $C_{1-3}$-alkyl group, an oxygen or sulfur atom, or an imino group optionally substituted by a $C_{1-3}$-alkyl group and an oxygen or sulfur atom or one or two nitrogen atoms and the abovementioned alkyl substituent may be substituted by a carboxy, carboxy-C1-3alkoxy, carboxy-$C_{1-3}$-alkylamino, or N-($C_{1-3}$-alkyl)-carboxy-$C_{1-3}$-alkylamino group, and X is an oxygen atom, a $C_{1-3}$-alkylimino, $C_{1-3}$-alkoxyimino, or $C_{1-3}$-alkylidene group, each of which may be substituted in the alkyl or alkanoyl moiety by a carboxy group, a $C_{1-3}$-alkyl group substituted in the 1 position by an imidazole or imidazolone group, wherein the irnidazole ring may be substituted by a phenyl or carboxy group and by one or two $C_{1-3}$-alkyl groups or by one, two, or three $C_{1-3}$-alkyl groups, wherein the substituents may be identical or different and one of the abovementioned alkyl substituents may simultaneously be substituted by a carboxy group or may be substituted in the 2 or 3 position by an amino, $C_2$-alkanoylamino, $C_{1-3}$-alkylamino, N-($C_{2-4}$-alkanoyl)-$C_{1-3}$-alkylamino, or di-($C_{1-3}$-alkyl)-amino group, and the imidazoloxne ring may be substituted by a $C_{1-3}$-alkyl group, wherein the alkyl substituent may be substituted by a carboxy group or in the 2 or 3 position by an amino, $C_{2-4}$-alkanoylamino, $C_{1-3}$-alkylamino, N-($C_{2-4}$-alkanoyl)-$C_{1-3}$-alkylamino, or di-($C_{1-3}$-alkyl)-amino group, and additionally a phenyl or pyridinc ring may be fused to the abovementioned imidazole or imidazolone rings via two adjacent carbon atoms, an imidazolidine-2,4-dion-5-yl group which may be substituted by one or two $C_{1-3}$-alkyl groups, wherein at the same time an alkyl substituent may be substituted by a carboxy group, a $C_{1-4}$-alkyl group which is substituted in the 1 position by an $R_3NR_4$— or $R_3NR_4$-$C_{1-3}$-alkyl group, and by a pyrrolinocarbonyl, 2,3-dehydro-piperidinocarbonyl, imidazol-1-yl-carbonyl, carboxy, aminocarbonyl, $C_{1-3}$-alkylaminocarbonyl, di-($C_{1-3}$-alkyl)-aminocarbonyl, isoxazolidin-1-ylcarbonyl, or 4- to 7-membered cycloalkyleneiminocarbonyl group, wherein in the abovementioned groups the cycloalkyleneimino moiety may be substituted by one or two $C_{1-3}$-alkyl groups and at the same timne each alkyl moiety or alkyl substituent in the abovementioned $C_{1-3}$-alkylaninocarbonyl, di-($C_{1-3}$-alkyl)-aminocarbonyl, or cycloalkyleneiminocarbonyl groups may be substituted by a carboxy group, and the remaining hydrogen atoms of the $C_{1-4}$-alkyl group may be wholly or partially replaced by fluorine atoms, wherein $R_3$ is a hydrogen atom or a $C_{1-3}$-alkyl group optionally substituted by a carboxy group, and $R_4$ is a hydrogen atom, a $C_{1-3}$-alkyl-$Y_2$, or carboxy-$C_{1-3}$-alkyl-$Y_2$ group or $R_3$ and $R_4$ together with the nitrogen atom between them are a 4- to 7-membered cycloalkyleneimino group optionally substituted in the 1 position by a carboxy, $C_{1-3}$-alkyl, or carboxy-$C_{1-3}$-alkyl group, wherein $Y_2$ is a carbon—nitrogen bond or a carbonyl, imino, or —NH—CO— group, wherein the carbonyl group of the —NH—CO— group is linked to the nitrogen atom of the $R_3NR_4$— group, and the itnino group occurring in the definition of the group $Y_2$ may additionally be substituted by a $C_{1-3}$-alkyl or carboxy-$C_{1-3}$-alkyl group, a $C_{1-3}$-alkyl or $C_{3-5}$-cycloalkyl group substituted in the 1 position by an $R_5NR_6$— group, wherein $R_5$ is a hydrogen atom, a $C_{1-3}$-alkyl, $C_{5-7}$-cycloalkyl, phenylcarbonyl, phenylsulfonyl, or pyridinyl group, and $R_6$ a $C_{1-3}$-alkyl, carboxy-$C_{1-3}$-alkyl, or carboxy-$C_{1-3}$-alkylcarbonyl group, a $C_{1-3}$-alkyl group which is substituted by a $C_{2-4}$-alkanoyl or $C_{5-7}$-cycloalkanoyl group and by a $C_{1-3}$-alkyl group substituted by a chlorine, bromine, or iodine atom, $R_b$ is a $C_{1-3}$-alkyl group; and $R_c$ is an amidino group which may optionally be substituted by a 2,2,2-trichloroethoxycarbonyl, $C_{1-8}$-alkoxycarbonyl, acetoxymethyloxycarbonyl, benzyloxycarbonyl, or benzoyl group, wherein the benzoyl moiety may be mono- or disubstituted by fluorine, chlorine, bromine, or iodine atoms, by $C_{1-3}$-alkyl or $C_{1-3}$-alkoxy groups, and the substituents may be identical or different, wherein the carboxy, amino, and imino groups mentioned in the definition of the abovementioned groups may also be substituted by a group which can be cleaved in vivo, or a $C_{1-3}$-alkanol ester, a tautomer, or a salt thereof.

4. The compound of the formula Ia according to claim 2, wherein

A is a methylene group;

B is an oxygen atom or an imino group;

$R_a$ is a cyclopropyl group substituted by the $R_1$-CO— group in the 1 position, wherein $R_1$ is a pyrrolidino or piperidino group optionally substituted by a methyl or ethyl group wherein each methyl or ethyl moiety may be substituted by a carboxy, carboxy-$C_{1-3}$-alkoxy, carboxy-$C_{1-3}$-alkylamino or N-($C_{1-3}$-alkyl)-carboxy-$C_{1-3}$-alkylamino group, a cyclopropyl group substituted in the 1 position by the $R_2$-CX— group, wherein $R_2$ is a phenyl, pyridyl, pyrazolyl group optionally substituted by a $C_{1-3}$-alkyl group, and X is an oxygen atom or a $C_{1-3}$-alkoxyimino or $C_{1-3}$-alkylidene group, each of which is substituted in the alkyl or alkoxy moiety by a carboxy group, a $C_{1-2}$-alkyl group substituted in the 1 position by an imidazole group, wherein the imidazole ring may be substituted by a phenyl or carboxy group and by one or two $C_{1-3}$-alkyl groups or by one, two, or three $C_{1-3}$-alkyl groups, wherein the substituents may be identical or different and one of the abovementioned alkyl substituents may simultaneously be substituted by a carboxy group or may be substituted in the 2 or 3 position by an amino, $C_{2-4}$-alkanoylamino, $C_{1-3}$-alkylamino, N-($C_{2-4}$-alkanoyl)-$C_{1-3}$-alkylamino, or di-($C_{1-3}$-alkyl)-amino group, wherein additionally a phenyl or pyridine ring may be fused to the abovementioned imidazole rings via two adjacent carbon atoms, a $C_{1-2}$-alkyl substituted in the 1 position by a benzimidazolon-1-yl group, wherein the imidazolone ring may be substituted by a methyl or ethyl group optionally substituted by a carboxy group, a methyl or ethyl group which is substituted in the 1 position by an $R_3NR_4$ or $R_3NR_4$-$C_{1-3}$-alkyl group, and by a di-($C_{1-3}$-alkyl)-aminocarbonyl group, by a isoxazolidin-1-yl-carbonyl group, by a pyrrolidinocarbonyl or piperidinocarbonyl group substituted by a $C_{1-3}$-alkyl group, wherein in the abovementioned groups each alkyl moiety or alkyl substituent in the abovementioned groups may be substituted by a carboxy group, wherein $R_3$ is a hydrogen atom or a $C_{1-3}$-alkyl group optionally substituted by a carboxy group, and $R_4$ is a hydrogen atom or a $C_{1-3}$-alkyl-$Y_2$ or carboxy-$C_{1-3}$-alkyl-$Y_2$ group, or $R_3$ and $R_4$ together with the nitrogen atom between them are a 4- to 7-membered cycloalkyleneimino group optionally substituted by a carboxy group, wherein $Y_2$ is a carbon—nitrogen bond, a carbonyl group or an imino group optionally substituted by a $C_{1-3}$-alkyl group, a $C_{1-2}$-alkyl group substituted in the 1 position by an $R_5NR_6$— group, wherein $R_5$ is a pyridinyl, phenylcarbonyl, or phenylsulfonyl group, and $R_6$ is a $C_{1-3}$-alkyl or carboxy-$C_{1-3}$-alkyl group, an n-propyl group substituted in the 3 position by a chlorine atom, which is substituted in the 1 position by a cyclopentylcarbonyl group, a cyclopropyl group substituted in the 1 position by a cyclopentylamino group, which is substituted at the nitrogen atom by a carboxy-$C_{1-3}$-alkylcarbonyl group;

$R_b$ is a methyl group; and $R_c$ is an amidino group which may optionally be substituted by a $C_{1-8}$-alkoxycarbonyl, acetoxymethytoxycarbonyl, 2,2,2-trichloroethoxycarbonyl, benzyloxycarbonyl, or benzoyl group, wherein the carboxy, amino, and imino groups mentioned in the definition of the abovementioned groups may also be substituted by a group which can be cleaved in vivo, or a $C_{1-3}$-alkanol ester thereof, a tautorner, or a salt thereof.

5. The compound of the formula Ia according to claim 2, wherein

A is a methylene group;

B is an imino group;

$R_a$ is a cyclopropyl group substituted by the $R_1$-CO— group in the 1 position, wherein R is a pyrrolidino or piperidino group optionally substituted by a methyl or ethyl group wherein each methyl or ethyl rnoicty may be substituted by a carboxy, carboxy-$C_{1-3}$-alkoxy, carboxy-$C_{1-3}$-alkylamino, or N-($C_{1-3}$-alkyl)-carboxy-$C_{1-3}$-alkylamino group, a cyclopropyl group substituted in the 1 position by the $R_2$-CX group, wherein $R_2$ is a phenyl, pyridyl, or pyrazolyl group optionally substituted by a $C_{1-3}$-alkyl group and X is an oxygen atom or a $C_{1-3}$-alkoxyimino or $C_{1-3}$-alkylidene group, each of which is substituted in the alkyl or alkoxy moiety by a carboxy group, a $C_{1-2}$-alkyl group substituted in the 1 position by an imidazole group wherein the imidazole ring may be substituted by one to three methyl groups or by two methyl groups and an ethyl group, wherein additionally one of the abovementioned methyl or ethyl substituents may simultaneously be substituted by a carboxy group, a methyl or ethyl group which is substituted in the 1 position by an $R_3NR_4$— or $R_3NR_4$-$CH_2$— group and by a di-($C_{1-3}$-alkyl)-aminocarbonyl, by a pyrrolidinocarbonyl or piperidinocarbonyl group optionally substituted by a $C_{1-3}$-alkyl group, wherein in the abovementioned groups each alkyl moiety or alkyl substituent may be substituted by a carboxy group, wherein $R_3$ is a hydrogen atom or a $C_{1-3}$-alkyl group optionally substituted by a carboxy group, and $R_4$ is a $C_{1-3}$-alkyl-$Y_2$ or carboxy-$C_{1-3}$-alkyl-$Y_2$ group, wherein $Y_2$ is a carbon—nitrogen bond, a carbonyl group or an imino group optionally substituted by a $C_{1-3}$-alkyl group, $R_b$ is a methyl group; and $R_c$ is an arnidino group which may optionally be substituted by a $C_{1-8}$-alkoxycarbonyl, acetoxymethytoxycarbonyl, 2,2,2-trichloroethoxycarbonyl, benzyloxycarbonyl, or benzoyl group, wherein the carboxy, amino, and imino groups mentioned in the definition of the abovementioned groups may be substituted by a group which can be cleaved in vivo, or a $C_{1-3}$-alkanol ester, a tautomer, or a salt thereof.

6. The compound of the formula I according to claim 1, wherein the group $R_a$ is in the 5 position, or a tautomer or salt thereof.

7. A compound selected from the group consisting of:
   (a) 2-(4-amidinophenylaminomethyl)-1-methyl-5-[1-(pyrrolidin-1-yl-carbonyl)cyclopropyl]-benzimidazole;
   (b) (E/Z)-2-(4-amidinophenylaminomethyl)-1-methyl-5-[1-[(pyridin-2-yl)-(carboxymethyloxyimino)methylene]-cyclopropyl]-benzimidazole;
   (c) 2-(4-amidinophenylaminomethyl)-1-methyl-5-[1-(2-carboxyethylamino)-1-(pyrrolidin-1-yl-carbonyl)-ethyl]-benzimidazole;
   (d) 2-(4-amidinophenylaminomethyl)-1-methyl-5-[1-[2-(2-carboxyethyl)-pyrrolidin-1-yl-carbonyl]cyclopropyl]-benzimidazole;
   (e) 2-(4-arnidinophenylaxinomethyl)-1-methyl-5-[2-(2-carboxyethyl)-4,5-dimethylimidazol-1-yl-methyl]-benzimidazole;
   (f) 2-(4-amidinophenylaminomethyl)-1-methyl-5-[1-(carboxymethylamino)-1-(pyrrolidin-1-yl-carbonyl)-ethyl]-benzimidazole; and
   (g) 2-(4-amidinophenylaminomethyl)-1-methyl-5-[1-(N-methylcarboxymethylcarbonylaminomethyl)-1-methyl-1-(pyrrolidin-1-yl-carbonyl)-ethyl]-benzimidazole, wherein the carboxy, amino, and imino groups thereof may also be substituted by a group which can be cleaved in vivo, or a $C_{1-3}$-alkanolester thereof, or an N-($C_{1-8}$-alkoxycarbonyl), N-benzyloxycarbonyl, or N-benzoyl-amidinc thereof, or a tautomer or salt thereof.

8. 2-(4-amidinophenylaminomethyl)-1-methyl-5-[1-(carboxymethylamino)-1-(pyrrolidin-1-yl-carbonyl)-ethyl]-benzimidazole, wherein the carboxy, amino and imino groups thereof may also be substituted by a group which can be cleaved in viyo, or a $C_{1-3}$-alkanolester thereof, or an N-($C_{1-8}$-alkoxy-carbonyl), N-benzyloxycarbonyl, or N-benzoyl-amidine thereof, or a tautomer or salt thereof.

9. The physiologically acceptable salt of a compound according to one of claims 1, 2, 3, 4, 5, 6, 7, or 8, wherein $R_c$ is one of the amidino groups mentioned in claim 1, 2, 3, 4, 5, 6, 7, or 8.

10. A pharmaceutical composition containing a compound according to one of claims 1, 2, 3, 4, 5, 6, 7, or 8, wherein $R_c$ is one of the amidino groups mentioned in claim 1, 2, 3, 4, 5, 6, 7, or 8, or a pharmaceutically acceptable salt thereof.

11. A method for treatment or prophylaxis of thrombus formation in a host in need of such treatment or prophylaxis, which method comprises administering an antithrombotic amount of a compound according to one of claims 1, 2, 3, 4, 5, 6, 7, or 8, wherein $R_c$ is one of the amidino groups mentioned in claim 1, 2, 3, 4, 5, 6, 7, or 8, or a pharmaceutically acceptable salt thereof.

* * * * *

UNITED STATES PATENT AND TRADEMARK OFFICE
CERTIFICATE OF CORRECTION

PATENT NO.    : 6,248,770 B1
DATED         : June 19, 2001
INVENTOR(S)   : Ries, U., Kauffmann, I., Hauel, N., Priepke, H., Nar, H., Stassen, J-M. and Wienen, W.

It is certified that error appears in the above-identified patent and that said Letters Patent is hereby corrected as shown below:

Column 9,
Line 30, "irnidazole" should read -- imidazole --.

Column 13,
Line 34, "amiaino" should read -- amidino --.

Column 17,
Line 39, "alkyLation" should read -- alkylation --.

Column 19,
Line 47, "racernates" should read -- racemates --.

Column 20,
Line 44, "amidiLnophenylaminomethyl" should read -- amidinophenylaminomethyl --.
Line 50, "amidinophe:nylaminomethyl" should read -- amidinophenylaminomethyl --.
Line 58, "benzimidazol-ehydrochloride" should read -- benzimidazole-hydrochloride --.

Column 22,
Line 12, "(0.21 moi)" should read -- (0.21 mol) --.

Column 23,
Line 32, "cyclolpropyl" should read -- cyclopropyl --.

Column 24,
Line 40, "cyclopropy" should read -- cyclopropyl --.

Column 25,
Line 29,"cyclyproyl" should read -- cyclopropyl --.

Column 27,
Line 9, "glaciaL" should read -- glacial --.
Line 64, "benzimi-dazole" should read -- benzimidazole --.

Column 28,
Line 8, "ethanol/-glacial" should read -- ethanol/glacial --

UNITED STATES PATENT AND TRADEMARK OFFICE
CERTIFICATE OF CORRECTION

PATENT NO.   : 6,248,770 B1
DATED        : June 19, 2001
INVENTOR(S)  : Ries, U., Kauffmann, I., Hauel, N., Priepke, H., Nar, H., Stassen, J-M. and Wienen, W.

It is certified that error appears in the above-identified patent and that said Letters Patent is hereby corrected as shown below:

Column 33,
Line 5, "benzimida-zole" should read -- benzimidazole --.

Column 34,
Line 19, "pro-panone" should read -- propanone --.
Line 59, "concentra-ted" should read -- concentrated --.

Column 38,
Line 20, "elhanolic" should read -- ethanolic --.

Column 40,
Line 28, "tetrafluoro-roborate" should read -- tetrafluoroborate --.

Column 44,
Line 27, "(4.0 mraol)" should read -- (4.0 mol) --.
Line 36, "so-dium" should read -- sodium --.
Line 39, "dichlo-romethane" should read -- dichloromethane --.
Line 40, "con-centrated" should read -- concentrated --.

Column 59,
Line 18, "tetrahydrofurane" should read -- tetrahydrofuran --.
Line 38, "tetrahydrofurane" should read -- tetrahydrofuran --.
Line 53, "tetrahydrofurane" should read -- tetrahydrofuran --.

Column 60,
Line 2, "jodoacetate/potassium" should read -- iodoacetate/potassium --.
Line 21, "amidinophe:nylaminomethyl" should read -- amidinophenylaminomethyl --.
Line 23, "hydrochlorid" should read -- hydrochloride --.

Column 62,
Line 67, "trifloromethyl" should read -- trifluoromethyl --.

UNITED STATES PATENT AND TRADEMARK OFFICE
CERTIFICATE OF CORRECTION

PATENT NO.    : 6,248,770 B1
DATED         : June 19, 2001
INVENTOR(S)   : Ries, U., Kauffmann, I., Hauel, N., Priepke, H., Nar, H., Stassen, J-M. and Wienen, W.

It is certified that error appears in the above-identified patent and that said Letters Patent is hereby corrected as shown below:

Column 63,
Line 5, "sulfuir atom" should read -- sulfur atom --.
Line 53, "rnoiety" should read -- moiety --.
Line 57, "irnidazolone" should read -- imidazolone --.

Column 64,
Line 20, "isoxazolidinylcarboniyl" should read -- isoxazolidinylcarbonyl --.
Line 24, "7-membere,d" should read -- 7-membered --.
Line 64, "brouiine" should read -- bromine --.

Column 67,
Line 51, "cycloalkyleneiemino" should read -- cycloalkyleneimino --.
Line 58, "naphtllyl" should read -- naphthyl --.
Line 63, "imirno" should read -- imino --.

Column 68,
Line 1, "abovernentioned" should read -- abovementioned --
Line 2, "C1-3alkoxy" should read -- $C_{1-3}$alkoxy --
Line 11, "irnidazole" should read -- imidazole --.
Line 21, "imidazoloxne" should read -- imidazolone --.
Line 27, "pyridinc" should read -- pyridine --
Line 43, "timne" should read -- time --.
Line 63, "itnino" should read -- imino --.

Column 69,
Line 45, "irnidazole" should read -- imidazole --.

Column 70,
Line 3, "abovemeritioned" should read -- abovementioned --.
Line 30, "methytoxycarbonyl" should read -- methyltoxycarbonyl --.
Line 37, "tautorner" should read -- tautomer --.
Line 48, "rnoicty" should read -- moiety --.

Column 71,
Line 16, "arnidino" should read -- amidino --.
Line 18, "methytoxycarbonyl" should read -- methyltoxycarbonyl --.

UNITED STATES PATENT AND TRADEMARK OFFICE
CERTIFICATE OF CORRECTION

PATENT NO. : 6,248,770 B1
DATED : June 19, 2001
INVENTOR(S) : Ries, U., Kauffmann, I., Hauel, N., Priepke, H., Nar, H., Stassen, J-M. and Wienen, W.

It is certified that error appears in the above-identified patent and that said Letters Patent is hereby corrected as shown below:

Column 72,
Line 1, "arnidinophenylaxinomethyl" should read -- amidinophenylaxinomethyl --.
Line 16, "amidinc" should read -- amidino --.
Line 21, "in viyo" should read -- in vivo --.

Signed and Sealed this

Fifth Day of November, 2002

Attest:

JAMES E. ROGAN
Attesting Officer  Director of the United States Patent and Trademark Office